US010739357B2

(12) United States Patent
Van Agthoven et al.

(10) Patent No.: US 10,739,357 B2
(45) Date of Patent: Aug. 11, 2020

(54) SYSTEMS AND METHODS TO DETERMINE THE AGE OF CELLS

(71) Applicant: Beckman Coulter, Inc., Brea, CA (US)

(72) Inventors: Andreas Van Agthoven, Marseilles (FR); Fabrice Malergue, Marseilles (FR); Christophe Godefroy, Miramar, FL (US); Enrique Rabellino, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 200 days.

(21) Appl. No.: 15/510,612

(22) PCT Filed: Sep. 11, 2015

(86) PCT No.: PCT/US2015/049797
§ 371 (c)(1),
(2) Date: Mar. 10, 2017

(87) PCT Pub. No.: WO2016/040870
PCT Pub. Date: Mar. 17, 2016

(65) Prior Publication Data
US 2018/0231573 A1 Aug. 16, 2018

Related U.S. Application Data

(60) Provisional application No. 62/059,684, filed on Oct. 3, 2014, provisional application No. 62/049,970, filed on Sep. 12, 2014.

(51) Int. Cl.
*G01N 33/80* (2006.01)
*G01N 33/72* (2006.01)
(Continued)

(52) U.S. Cl.
CPC ....... *G01N 33/723* (2013.01); *G01N 15/1459* (2013.01); *G01N 33/492* (2013.01);
(Continued)

(58) Field of Classification Search
CPC .. G01N 33/723; G01N 33/492; G01N 33/582; G01N 33/721; G01N 33/726;
(Continued)

(56) References Cited

U.S. PATENT DOCUMENTS

2007/0020612 A1* 1/2007 Van Agthoven ..... G01N 33/726 435/4
2007/0267361 A1* 11/2007 Tyvoll ............... B01L 3/502753 210/787

FOREIGN PATENT DOCUMENTS

| WO | 92/17107 A2 | 10/1992 |
| WO | 2010/019372 A1 | 2/2010 |
| WO | 2010/135574 A2 | 11/2010 |

OTHER PUBLICATIONS

Lasch et al. Separation of Erythrocytes into Age-Related Fractions by Density or Size? Counterflow Centrifugation. Clin Chem. Lab 38 (7): 629-632 (2000).*
(Continued)

*Primary Examiner* — Gailene Gabel
(74) *Attorney, Agent, or Firm* — Merchant & Gould P.C.

(57) ABSTRACT

Systems and methods are provided for determining the age of cellular hemoglobin in individual red blood cells in a blood sample by determining the percentage of HbA1c. In embodiments, a method includes measuring side scatter and fluorescence of the individual red blood cells and identifying immature red blood cells and mature red blood cells from the side scatter and fluorescence measurement. In embodiments, data collected includes the exact number of red blood cells, the fraction limits in fluorescence and side scatter units, the mean value of each fraction in fluorescence and side scatter units, the mean FL1 values per fraction in arbitrary units and the mean side scatter values per fraction in arbitrary units. In embodiments, a method also includes deriving a HbA1c content from the measured mean fluorescence of the indi-
(Continued)

vidual red blood cells and determining the percentage of HbA1c from the HbA1c content and the hemoglobin content of the red blood cells.

20 Claims, 26 Drawing Sheets

(51) Int. Cl.
    *G01N 15/14*     (2006.01)
    *G01N 33/49*     (2006.01)
    *G01N 33/58*     (2006.01)
    *G01N 15/00*     (2006.01)

(52) U.S. Cl.
    CPC ......... *G01N 33/582* (2013.01); *G01N 33/721* (2013.01); *G01N 33/726* (2013.01); *G01N 33/80* (2013.01); *G01N 2015/0076* (2013.01); *G01N 2015/1402* (2013.01); *G01N 2015/1477* (2013.01); *G01N 2015/1488* (2013.01); *G01N 2333/805* (2013.01)

(58) Field of Classification Search
    CPC ............... G01N 33/80; G01N 15/1459; G01N 2015/1402; G01N 2015/1477; G01N 2015/1488; G01N 2333/805; G01N 2015/0076
See application file for complete search history.

(56) References Cited

OTHER PUBLICATIONS

Virtue et al. Relationship Between GHb Concentration and Erythrocyte Survival Determined from Breath Carbon Monoxide (Diabetes Care 27 (4): 931-935 (Apr. 2004).*
R. M. Cohen et al., "Red cell life span heterogeneity in hematologically normal people is sufficient to alter HbA1c", Blood, 112(10): 4284-4291 (2008).
S. Gray et al., "The Tagging of Red Cells and Plasma Proteins With Radioactive Chromium", The Journal of Clinical Investigation, 29: 1604-1613 (1950).
Lewis et al., "Dade and Lewis Practical Haematology", Ninth Edition, Chapter 15: 315-337 (2001).
M.A. Virtue et al., "Relationship Between GHb Concentration and Erythrocyte Survival Determined From Breath Carbon Monoxide Concentration", Emerging Treatment and Technologies, 2004, Diabetes Care, 27(4): 931-935 (2004).
E.R. Borun et al., "The Distribution of FE59 Tagged Human Erythrocytes in Centrifuged Specimens as a Function of Cell Age", The Journal of Clinical Investigation, 36(5): 676-679 (1957).
E. Lach-Trifilieff et al., "Complement Receptor 1 (CD35) on Human Reticulocytes: Normal Expression in Systemic Lupus Erythematosus and HIV-Infected Patients", The Journal of Immunology, 162(12): 7549-7554 (1999).
International Search Report and Written Opinion for PCT/US2015/049797, dated Oct 30, 2015.

* cited by examiner

Uncorrected FL4/SS or HbA1c percentage values (arbitrary units)

HbA1c percentage derived time axis

Blood glucose compared to adapted derived HbA1c percentage in 26 patients

Blood glucose compared to adapted derived HbA1c percentage in 26 patients

Blood glucose compared to adapted derived HbA1c percentage in 26 patients

Age dependent representation of cells in the blood circulation.

Age dependent representation of cells in the blood circulation.

Age dependent representation of cells in the blood circulation.

Age dependent representation of cells in the blood circulation.

Mean cellular hemoglobin content as a function of the age of cells.

Mean cellular hemoglobin content as a function of the age of cells.

Mean cellular hemoglobin content as a function of the age of cells.

Mean cellular hemoglobin content as a function of the age of cells.

SYSTEMS AND METHODS TO DETERMINE THE AGE OF CELLS

CROSS-REFERENCE TO RELATED APPLICATIONS

This application is a U.S. National Stage application of PCT/US2015/049797, filed Sep. 11, 2015, which claims priority to U.S. Patent Application Ser. No. 62/059,684 filed on Oct. 3, 2014, and claims priority to U.S. Patent Application Ser. No. 62/049,970 filed on Sep. 12, 2014, and which applications are hereby incorporated by reference in their entireties. To the extent appropriate, a claim of priority is made to each of the above disclosed applications.

FIELD OF THE DISCLOSURE

The present disclosure relates to systems and methods for the determination of the age of cellular hemoglobin in cells and/or the mean age of red cells.

BACKGROUND OF THE DISCLOSURE

The life span of red blood cells has been derived from the measurement of the clearance of Chromium 51 labelled red cells in vivo (Gray, S. J. and Stirling, K. 1950, J. Clin. Invest. 29: 1604-1613, for a review; Dacie and Lewis; Practical Haematology, Ninth Edition, 2001, Ed.; S. M. Lewis, B. J. Bain and I. Bates, Publ. Churchill Livingstone). This procedure is invasive and cumbersome and is not widely used. Other techniques have been developed to measure the life span of erythrocytes non-invasively, including the measurement of carbon monoxide in breath (M. A. Virtue et al. 2004, Diabetes Care; vol. 27 No 4 pp 931-935), density centrifugation of red cells (Borun E R, et al. J Clin Invest 36:676, 1957) and flow cytometric measurement of CD35 on the cell surface of red cells (Lach-Trifilieff et al. 1999, Journal. Immunol. 162, (12): 7549). However, none of these techniques have been shown to consistently provide for the determination of life-span or mean age of red cells.

It is therefore desirable to develop systems and methods to determine the age of cellular hemoglobin and/or the mean age of red blood cells.

SUMMARY OF THE DISCLOSURE

The systems, methods, kits, and compositions described herein provide for the ability to determine the percentage of HbA1c on a cell by cell basis, provide for a determination of the age profile of a population or subpopulation of red blood cells, provide for determination of the mean age of the red blood cells, provide for determination of the life span of the red blood cells, and provide for determination of estimated glucose content. Analysis of a single blood sample can provide information from the previous 100 to about 120 days. A determination of the age profile of a population or subpopulation of cells is useful in the monitoring of diabetes and other disorders involving blood glucose. A determination of the age profile of a population or subpopulation of cells is useful in the monitoring of anemia and other disorders involving hemoglobin content of red blood cells. In embodiments, blood transfusions conducted with the past 100 to about 120 days can be detected. See FIG. 13.

In one aspect, the present disclosure relates to systems and methods for determining age of cellular hemoglobin in individual red blood cells in a blood sample by determining the percentage of HbA1c. Another aspect involves determining the mean age of red blood cells in a sample. The methods and systems are useful in methods of monitoring of diabetes or anemia, the presence of a transfusion, and/or the presence of a bleeding event in a subject. The systems and methods are also useful in monitoring the progression or improvement in diabetes or anemia.

In one aspect, the present disclosure provides kits, and reagents for determining the age of red blood cells in a sample. In embodiments, a kit for determining the age profile of a population of red blood cells in a sample comprises: a) an antibody or antigen binding fragment thereof that specifically binds HbA1C or a variant thereof; b) a dye that specifically binds to RNA; and c) a red blood cell reference control sample. In some embodiments, the red blood cell reference control cell has known percentage of HbA1C. In other embodiments, the reference control cell is a normal control sample such as from a subject not having diabetes or anemia. In other embodiments, the reference control cell is from a subject having diabetes with a known HbA1C value. In embodiments, the antibody or antigen binding fragment is detectably labelled. In embodiments, the dye that specifically binds to RNA is acridine orange. In embodiments, the kit can further comprise a reagent for permeabilizing red blood cells. In other embodiments, a kit further comprises a computer readable medium containing instructions for determining the age and/or density of the red blood cells in the sample as described herein.

In another aspect, the present disclosure provides systems for determining the age and/or density of red blood cells in a sample. In embodiments, a system for determining the age of a red blood cell population comprises a detector of side scatter and fluorescence of the individual red blood cells; a calculator of a percentage HbA1c content from the measured fluorescence at at least one wavelength, and measured side scatter of the individual red blood cells; a divider of the red blood cell population into a plurality of fractions using the mean percentage of HbA1c for reticulocytes, each fraction comprising a substantially equal number of red blood cells; a calculator of a life span factor for each sample; and a calculator of the age of the fractions of the sample. In other embodiments, the system further comprises a calculator of the mean age of the sample and comparing the mean age of the sample to the mean age of a normal control sample. In yet other embodiments, the system further comprises a calculator of the mean cellular hemoglobin of cells of a certain age, and determining whether the mean cellular hemoglobin changes depending on the age of the cells.

In other embodiments, the present disclosure provides a system comprising a nontransitory computer readable medium with the instructions for implementing steps of a method comprising determining the hemoglobin, HbA1c, and RNA content of each of the individual red blood cells in a sample; determining the percentage of HbA1c in each of the individual cells from the HbA1c content and the hemoglobin content of each of the individual red blood cells; fractionating the red blood cell population into a plurality of fractions by comparing the percentage of HbA1c in the individual cells to the mean percentage of HbA1c of a reference cell fraction of the sample, each fraction comprising a substantially equal number of red blood cells; determining the mean percentage of HbA1c in each fraction, and identifying the age of the red blood cells in the fraction by comparing the mean percentage of HbA1c to a mean percentage of HbA1c for a reference control cell or reference control fraction. In embodiments, the system further comprises determining the density of the red blood cells in the sample belonging to a fraction of a certain HbA1c percentage as compared to the same fraction of the reference control cells. In embodiments, the reference control cells have a mean age of at least 28 days.

Another aspect of the present disclosure provides methods of determining the age and/or density of red blood cells in a sample. In embodiments, a method for determining age profile of a population of red blood cells in a blood sample comprises: measuring hemoglobin and HbA1c content of each of the individual red blood cells in the population; determining the percentage of HbA1c in each of the individual cells from the HbA1c content and the hemoglobin content of each of the individual red blood cells; fractionating the red blood cell population into a plurality of fractions by comparing the percentage of HbA1c in the individual cells to the mean percentage of HbA1c of a reference cell fraction, each fraction comprising a substantially equal number of red blood cells; determining the mean percentage of HbA1c in each fraction, and identifying the age of the red blood cells in the fraction by comparing the mean percentage of HbA1c to a mean percentage of HbA1c for a reference control fraction or reference control cells.

In yet other embodiments, the method further comprises determining the density of the red blood cells in the sample belonging to a fraction of a certain HbA1c percentage as compared to the same fraction of the reference control cells. In yet other embodiments, the method further comprises collecting data from each fraction, the data comprising the exact number of red blood cells, the mean HbA1c of the reticulocyte fraction, and the value of each fraction in fluorescence and side scatter units for each individual red blood cell in the sample.

In embodiments, in the methods described herein, the hemoglobin of each individual red blood cell is measured by side scatter. In embodiments, the HbA1c is measured using a detectably labelled antibody specific for HbA1c or variant thereof. For example, the label is a fluorescent moiety. In embodiments, the methods further comprise measuring the RNA content of in the individual cells, wherein the presence of RNA identifies the cell as a reticulocyte. In an embodiment, RNA is measured by binding to a dye, such as acridine orange. In embodiments, the reference cell fraction or control cells are cells with a known percentage of HbA1c, such as reticulocytes. In embodiments, the reference control fraction is an internal cell type in the sample that is being analysed. In embodiments, the reference control cells have a mean age of at least 28 days.

In other embodiments, the method further comprises determining whether the age profile of the population of red blood cells includes a greater number of older cells as compared to a an age profile of the reference cell population as indicative of a disease state or status of a disease state. In an embodiment, the disease state is diabetes. In embodiments, the method further comprises determining a mean age of cells in the sample and comparing the mean age to a mean age of a normal control sample, wherein a difference in the mean age is indicative of or status of a disease. In an embodiment, the disease state is diabetes.

In yet other embodiments, the method further comprises determining the mean cellular hemoglobin content of a fraction of the sample having a certain age, and determining whether there is a difference in the mean cellular hemoglobin content in fractions of different ages. In embodiments, the difference is indicative of anemia, a bleed, or a transfusion.

BRIEF DESCRIPTION OF THE DRAWINGS

FIG. 1 (B) is a representation of the data obtained in the analysis shown in FIG. 1A, region C. The cellular events are plotted on abscissas, representing arbitrary values of FL4/SS or HbA1c percentage. Using the program, the cell population is divided in ten fractions containing approximately equal amounts of cells. Mean values of the fractions are indicated on the HbA1c percentage axis.

FIG. 1 (C) is a representation of analysis of the reticulocyte population as obtained in FIG. 1A, region B. The reticulocytes were represented in an FL4 diagram. Cells with relatively high levels of HbA1c were excluded from the population.

FIG. 2 (B) is a standard curve of cytometric HbA1c percentage determination showing the correlation of HbA1c percentage to FL4/SS values; abscissa; expected IFCC HbA1c percentage values from 120 samples; ordinate; Cytometric FL4/SS values of the same 120 samples. FL4 values were corrected for background and compensation and divided by the side scatter. FL4/SS values were normalized using internal control values.

FIG. 2 (C) is a standard curve of cytometric HbA1c percentage determination after data transformation with formula I. Normalized FL4/SS values were transformed using formula I as described in example 2. The transformed data of 120 samples are represented as in FIG. 2B.

FIG. 3 (B) is a graphical representation of the change of IFCC HbA1c percentage on a time axis. The transformation of the fraction limit values into time is shown in Table 1.

FIG. 3 (C) is a graphical representation of IFCC HbA1c percentage on an age axis. The age is expressed in days in negative values.

FIG. 3 (D) is a graphical representation of the derived IFCC percentage HbA1c values versus age. The derivative of FIG. 3C yields a constant value (see Table 1). This value has been normalized to the measured mean IFCC HbA1c percentage of the reference samples.

FIG. 3 (E) is a graphical representation of fraction size per fraction. The fraction sizes expressed in IFCC HbA1c percentage units were calculated as shown in Table 1.

FIG. 3 (F) is a graphical representation of the percentage of cells represented in the blood circulation on an age axis. The calculation of the percentages is presented in Table 1.

FIG. 5 (B) is a scatterplot representation of the relationship of derived HbA1c percentage values of the fractions of the patient samples and the mean glucose concentration measured during the period of the age of the corresponding fractions. The data have been obtained as described in example 4. The mean glucose values and the derived HbA1c percentage value have been aligned as described in example 9.

FIGS. 12 A-C show % HbA1C measurements on 120 blood samples using three other tests including the Tosoh, Primus, and Roche test strategies.

FIGS. 13 A-E show the information that can be obtained from a single blood sample including percentage HbA1c per age of red blood cell population, estimated glucose per age of red blood cells, mean cellular hemoglobin per age of cells, percentage of cells of a certain age in a sample.

DETAILED DESCRIPTION OF THE DISCLOSURE

Definitions

Figure 1A:
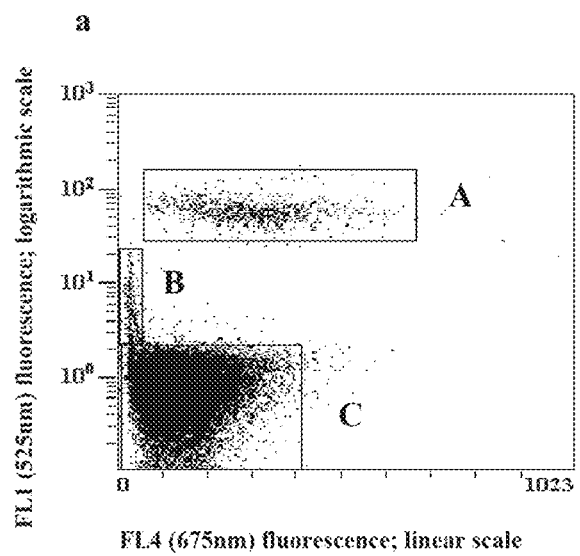
FIG. 1 (A) shows a graphic representation of flow cytometric data obtained from a human blood sample from a normal subject; FL4 (675 nm) fluorescence linear scale vs. FL1 (525 nm) fluorescence logarithmic scale; Region A; control cells. Region B; Red blood cell reticulocytes. Region C; mature red blood cells. The red blood cells were labelled with Fluor Alexa 647 conjugated anti-HbA1c antibody and acridin orange. Included in the assay were control cells previously labelled with carboxyfluoresceinsuccimidylester. The control cells originated from a diabetic patient. Fluorescence FL1 (525 nm) and FL4 (675 nm) was measured on a FC500 Cytometer.

Unless defined otherwise, all technical and scientific terms used herein have the same meaning as commonly understood by one of ordinary skill in the art to which the disclosure pertains.

"About" as used herein when referring to a measurable value is meant to encompass variations of ±20% or ±10%, more preferably ±5%, even more preferably ±1%, and still more preferably ±0.1% from the specified value.

On hematology analyzers, "mean corpuscular hemoglobin (MCH)" of a blood sample is the average mass of hemoglobin per red blood cell and is derived from the red blood cell count (RBC) and total hemoglobin (Hgb) of the blood sample. The latter is obtained by a spectrophotometric measurement of hemoglobin concentration of a lysed blood sample. MCH is an average measurement of all red blood cells; it does not represent hemoglobin content of individual red blood cells. It is calculated by dividing the total mass of hemoglobin by the number of red blood cells in a volume of blood:

$$MCH=(Hgb*10)/RBC.$$

On a flow cytometer, a "reference control" is commonly used to calibrate the instrument. The reference control is typically made of fluorescent particles with known hemoglobin concentration, or equivalent hemoglobin concentration, known side scatter and fluorescence intensities. These typically include, but are not limited to, synthetic particles, human or animal blood cells, and processed human or animal blood cells. Upon calibration, quantitative measurement of cellular HbA1c, i.e., the absolute amount of this hemoglobin variant in the individual red blood cell can be achieved on the flow cytometer.

The term "reference cell fraction" as used herein refers to a fraction of cells of the blood sample that have characteristics that differ from the other fractions of red blood cells. In embodiments those characteristics include the presence of RNA and a lower HbA1c content. In embodiments, the reference cell fraction is the reticulocyte fraction.

The term "normal cell control" refers to cells derived from a subject not known to have the disease or condition. In embodiments, the normal cell control is from a nondiabetic or a nonanemic individual. In embodiments, normal cell controls are used to compare, for example, mean age of red blood cells to the mean age of red blood cells in a diabetic subject.

The term "side scatter", as known in flow cytometry, refers to the light scatter signal at about 90 degrees or at the right angle from the incident light, generated by a particle or a blood cell passing through the aperture of a flow cell. The forward scatter signal refers to the light scatter signal measured less than 10 degrees from the incident light. Side scatter measurement refers to the measurement of the side scatter signals by an optical detector. All commercially available flow cytometers are equipped with a detection system which enables measurement of the forward scatter and side scatter signals.

The term "HbA1c" as used herein refers to a glycated form of hemoglobin. This glycated hemoglobin found in red blood cells is the reaction product of plasma glucose with hemoglobin. The amount of HbA1c increases as a function of plasma glucose.

The term "reticulocytes" as used herein refers to immature red blood cells having a reticular network of ribosomal RNA.

The term "percentage of represented cells in a fraction" is equal to 1/(time represented on the HbA1c percentage scale).

Formulas

This disclosure includes a number of formulas useful in the methods and systems described here. Formulas included herein are:

(I) $y=c*e^{0157*x}$, where c is a constant, y is the HbA1c reference value and x is the cytometric FL4/SS values (II) $y=c*(e^{a*x}-e^{b*x})*(d+e^{-f*x})$, where the values of the constants were empirically determined by comparison with glucose values as shown below; a=0.03, b=−0.01, c=15.1, d=1.8, e=2.71828 (Euler's constant), f=1.8. x, y as in formula I (III) $y=15.1*(e^{0.03*x}-e^{-0.01*x})*(1.8+e^{-1.8*x})$ where x, y as in formula I (IV) $y=c_1*x^{1.3}$, where x are the former age values and y are the new age values. The constant $c_1$ has been given a value as to keep the age of the last fraction at 115 days.

(V) mean value (m) is given by $$\frac{2}{(a-b)*(0.5+a2+0.5*b2)^{0.5}}$$

in which a and b are the respective cut-off values (VI) LOG $10(c_1*RNA)*$LOG $10(c_2*29.8*Hb)$, where $c_1$ is a constant having a value of 3.33 and $c_2$ is a constant having a value of 0.028

(VII) Antibody binding kinetics;

$$x = \frac{\{\ln(y+c1) - \ln(c1)\}}{c2}$$

reverse; $y=c_1*(e^{x*c2}-1)$ where y is the HbA1c percentage given by the reference laboratory in IFCC units, x is the cytometric HbA1c percentage determined in the presence of an internal reference and $c_1$ and $c_2$ are constants.

(VIII) $(d)=4.54*(e^{0.157*(c)}-1)$, where fraction limit values are expressed in IFCC percentage HbA1c in Table 1. The values of column d (d) were obtained from the values of column c, using Formula (VIII).

(IX) NGSP=(0.915*IFCC)+2.15

(X) IFCC HbA1c percentage=$4.54*(e^{0.157*cytometric\ arbitrary\ HbA1c\ percentage}-1)$ (XI) $w=e^{0.157*(v)}-1$ Systems In embodiments, a system is provided for determining the age of a red blood cell population comprising: a detector of side scatter and fluorescence of the individual red blood cells; a calculator of a percentage HbA1c content from the measured fluorescence at at least one wavelength, and measured side scatter of the individual red blood cells; a divider of the red blood cell population into a plurality of fractions using the mean percentage of HbA1c for a reference cell fraction, each fraction comprising a substantially equal number of red blood cells; a calculator of a life span factor for each sample; and a calculator of the age of the fractions of the sample. In embodiments, the reference cell fraction is the reticulocyte fraction.

In other embodiments, a system is provided for determining the mean hemoglobin content per age of a red blood cell population comprising: a detector of side scatter and fluorescence of the individual red blood cells; a calculator of a percentage HbA1c content from the measured fluorescence and measured side scatter of the individual red blood cells; a divider of the red blood cell population into a plurality of fractions using the mean percentage of HbA1c for a reference cell fraction, each fraction comprising a substantially equal number of red blood cells; a calculator of a life span factor for each sample; a calculator of the age of the fractions of the sample; and a calculator of the mean cellular hemoglobin content per age of cells in the sample. In embodiments, the reference cell fraction is the reticulocyte fraction.

In other embodiments, a system further comprises a calculator of the mean age of cells in a sample and comparing the mean age of the cells in the sample with the mean age of cells in a normal control sample, where a difference in the mean age of the cells is indicative of a disease or status of the disease, such as diabetes. In other embodiments, a system further comprises a calculator of the mean cellular hemoglobin of different ages of cells in a sample and comparing the mean cellular hemoglobin of different ages of cells to one another to identify a change in the mean cellular hemoglobin with the age of the cell, where a change is indicative of a disease or status of the disease, such as anemia or an event such as a bleed or a transfusion.

In embodiments, a calculator of the age of a fraction of the sample comprises calculating the position of the mean percentage HbA1c in each fraction as compared to the position of the mean percentage HbA1c of the reference control fraction, calculating the position of the mean HbA1c within the fraction, calculating the derived NGPS HbA1c percentage per fraction, calculating the age of the fraction by multiplying the mean percentage of the fraction with a constant such as 3.44 (an exemplary value for the IFCC percentage HbA1c for reference sample). The product is then input into formula XI as shown in Table 2D:

$$w=e^{0.157*(v)}-1$$

and the difference between each fraction is calculated to provide value x. Value x is divided by the position of the mean of a fraction, which is then divided by the percentage of total events in the fraction. The dividend is then multiplied with a life span factor and cumulative values of the product are determined. In embodiments, a reference control fraction is an internal control with a known amount of HbA1c, such as the reticulocyte fraction.

Optionally any of the systems described herein can include a calculator of the derived HbA1c percentage of a fraction, a calculator of the IFCC percentage of HbA1c using the formulas provided herein and/or a calculator of the percentage HbA1c corrected for background.

In embodiments, the system comprises one or more computer readable media storing data instructions, which when executed by a computing device cause the computing device to implement one or more of the steps, functions, or operations of the methods as described herein. The system can also include electronics configured to perform any one or more of the steps, functions, or operations disclosed herein. The computing device and the electronics can include software or firmware instructions, for example. Electronics can also include other electronic hardware devices which are specially designed or configured to perform the steps, functions, or operations described herein, which may not utilize any additional software or firmware instructions. The modules or calculators described herein, used for determining one or more aspects of the present disclosure, can be implemented as hardware (such as electronic hardware devices), hardware and software (such as a computing device), software, or computer readable media storing instructions that are executable by a processing device.

For example, a method includes measuring hemoglobin, and HbA1c of each of the individual red blood cells in the population; determining the percentage of HbA1c in each of the individual cells from the HbA1c content and the hemoglobin content of each of the individual red blood cells; fractionating the red blood cell population into a plurality of fractions by comparing the percentage of HbA1c in the individual cells to the mean percentage of HbA1c of a reference cell fraction, each fraction comprising a substantially equal number of red blood cells; determining the mean percentage of HbA1c in each fraction, and identifying the age of the red blood cells in the fraction by comparing the mean percentage of HbA1c to a mean percentage of HbA1c for a reference control cell fraction.

In embodiments, the method further comprises determining the density of the red blood cells in the sample belonging to a fraction of a certain HbA1c percentage as compared to the same fraction of control cells. In embodiments, the control cells have a mean age of at least 28 days. In embodiments, the method further comprises measuring RNA in the individual cells in the sample. In embodiments, the reference cell fraction is the reticulocyte fraction. In embodiments, the reference cell fraction is a an internal control cell population having a known HbA1c content as described in U.S. Pat. No. 7,968,279, which is hereby incorporated by reference in its entirety.

In embodiments, cells in the sample are permeabilized with an agent that allows antibodies and/or antigen binding fragments thereof to penetrate the cells. In embodiments, the cells being analysed are labelled with a reagent that binds to DNA or RNA and/or an agent that specifically binds to HbA1c labelled with a detectable reagent. The reagent that binds DNA/RNA allows identification of cells as reticulocytes. In embodiments, the detectable reagent is a fluorescent label. In embodiments, the agent that specifically binds to HbA1c is an antibody specific for HbA1c or variant thereof. In embodiments, the detectable reagent for RNA/DNA is detected at a different wavelength than that of the detectable label on the antibody. In embodiments, the side scatter of each of the individual cells is determined.

The percentage of HbA1c for each cell is determined by dividing the fluorescence of the detectable agent (FL4) with the side scatter (SS). In embodiments, the normalized FL4/SS data were transformed using the formula (I):

$$y = c \ast e^{0.157 \ast x}$$

in which y is the transformed data, x is the normalized FL4/SS data and c is a constant (e.g. 2.74). This function however does not go through the origin. Although useful for correction of HbA1c percentage values, approximately varying between 5% and 15%, it was replaced for the purpose of the fractions in our analysis varying from approximately 0% to 25%. For the replacing the function, a general form of (II) was chosen;

$$y = c \ast (e^{a \ast x} - e^{b \ast x}) \ast (d + e^{-f \ast x})$$

The values of the constants were empirically determined by comparison with glucose values as shown below. Exemplary constant values are a=0.03, b=−0.01, c=15.1, d=1.8, e=2.71828 (Euler's constant or the base of natural logarithms), f=1.8. The first part of the replacing formula makes the curve go through the origin; the second part introduces a slight reverse sigmoid curve in the section of the lower values of the curve.

In embodiments, the raw data from each of the cells in the sample is divided into fractions. Fractions are based on the number of cellular events and the rank order of events based on the data from samples from normal nondiabetic samples. In embodiments, the mean percentage of HbA1c of the reticulocytes present in the blood stream is taken as the fraction limit value. In embodiments, the data from the cells are divided into ten fractions, each fraction containing about the same number of cells. The fraction limit of the last fraction 10 is estimated to be the mean fluorescence value of the last fraction 10 plus half of the difference between the fraction limit values of fractions 8 and 9. The values are corrected for background and compensation of fluorescence.

In embodiments, the percentage of HbA1c is converted to IFCC HbA1c percentage using a linear correlation curve between the internal reference control sample and the measured HbA1c values. In embodiments, the percentage IFCC HbA1c is determined using the following equation:

$$\text{IFCC HbA1c percentage} = 4.54 \ast (e^{0.157 \ast \textit{cytometric arbitrary HbA1c percentage}} - 1) \quad \text{(Formula X)}.$$

In embodiments, a life span factor is determined for each sample. The life span factor is related to the reticulocyte hemoglobin and RNA content. In embodiments, a life span factor is calculated for each sample. Acridine orange RNA staining; FL1 (488 nm) fluorescence values (side scatter values) are determined for reticulocytes of each sample. A best correlation ($R_2$=0.8) was found with the product of the logarithm of the FL1 values (RNA content) of the reticulocytes and the logarithm of side scatter values of the reticulocytes (Hemoglobin content). To obtain stable RNA values, the value of the RNA is determined by subtracting the FL1 value of the first fraction from the FL1 value of the reticulocytes and dividing the difference by the FL1 value of the third fraction, which will not contain any RNA. The mean hemoglobin content of the reticulocytes (Hb) was determined using the hemoglobin content of the internal control cells. The formula and the constants are:

$$\text{LOG } 10(c_1 * RNA) * \text{LOG } 10(c_2 * 29.8 * Hb)$$

in which RNA and Hb are as described above, $c_1$ is a constant having a value, for example, of 3.33 and $c_2$ is a constant having an exemplary value of 0.028 in the present disclosure. The 29.8 value is an example of the mean hemoglobin content of the internal control cells.

In embodiments, a life span factor for a sample from a subject suspected of having a disease such as diabetes is determined by subtracting acridine orange RNA staining FL1 (488 nm) fluorescence values of the total cells from the values of reticulocytes in the subject's sample to yield value af. The fluorescence values of FL1 background value (e.g. 0.17) is subtracted from the value of the total cells to yield value ag. Value af is divided by value ag to yield value ah, which is then raised to a power of 1.3 to yield value ai. The values of hemoglobin content of the reticulocytes determined by side scatter is divided by that of the total cells, which is then raised to a power of 1.7, to yield value al. To calculate the life span factor value ai is multiplied by value al.

In other embodiments, a life span factor can be calculated by dividing the percentage of HbA1c of 10% of the oldest cells by the mean percentage of the HbA1c of the total cells.

In embodiments, the age of the fractions is calculated using the total number of cellular events in a fraction compared to the mean of the percentage of corrected HbA1c of each fraction. In embodiments, cellular age of each fraction is calculated by dividing the fraction limit value of each fraction (Fraction limit values on a FL4/SS scale) by the mean of the fractions. This value for each fraction is multiplied with the IFCC HbA1c percentage of the reference sample (e.g. 3.44%) to obtain value v. Values v for each fraction are transformed with formula XI:

$$w = e^{0.157*(v)} - 1$$

Differences between the fractions are determined by $x = w_n - w_{n-1}$. Values of (x) are divided by the position of the mean of a fraction, relative to the position of the mean of a corresponding fraction of the reference control to provide value y. The total number of cellular events in each fraction is divided by the number of cellular events of the ten fractions and multiplied with 10 to provide value aa. Value y is multiplied by value aa. This value is then multiplied by the life-span factor as determined by best fit or calculated as presented in Table 2E. The result of this calculation is value ac. Cumulative values of (ac) are determined by $ac_n + ac_{n-1}$, representing the age of the fractions in days. In embodiments, the reference control is an internal control cell population having a known HbA1c content as described in U.S. Pat. No. 7,968,279, which is hereby incorporated by reference in its entirety.

In embodiments, the determination of the age of the cells in the fractions of the analysis provides application of a time axis to red blood cell parameters of choice. Mean cellular hemoglobin of a fraction of a cellular age is determined as described in U.S. Pat. No. 7,541,190, which is hereby incorporated by reference in its entirety.

In embodiments, a mean age of the red blood cells is also calculated. In some embodiments, the mean age is calculated by multiplying the number of cells in each fraction with the age of the fraction. The sum of these multiplications is divided by the total number of red cells of the sample.

Figure 14:
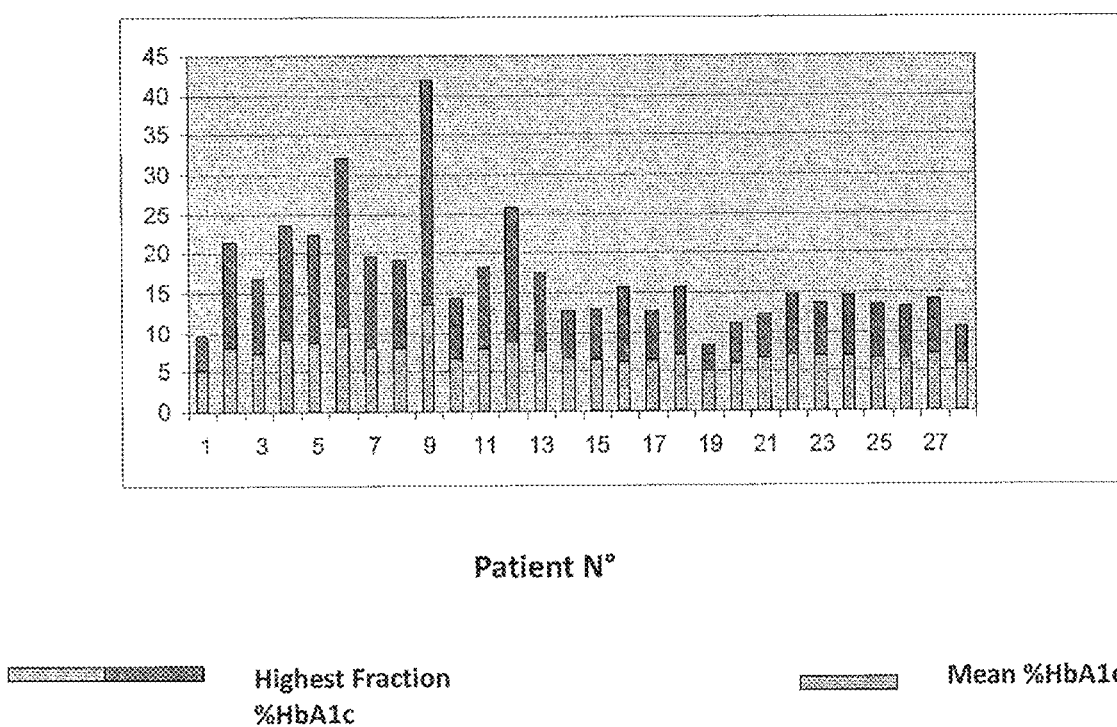
FIG. 14 shows a comparison of mean HbA1c and highest fraction HbA1c of 28 diabetic patients.

The age of each fraction in days can be used to determine a mean age for the blood sample. A mean age of the blood sample from a subject suspected or known to have a disease can be compared to mean age of control sample from a subject not having the disease. In embodiments, the disease is diabetes. The sample can be taken at initial diagnosis or after treatment to monitor effectiveness of treatment. Determining the percentage of HbA1c in each fraction and the percentage of cells in each fraction allows a determination of the subject's history over about 100 to about 120 days (life span of the red blood cell). The data from each sample allows a determination of the effectiveness of treatment and is more accurate than written logs reported by subjects' over time. See FIG. 14. In embodiments, an increase in the mean age of the cell population is indicative of the presence of or the status of diabetes.

In embodiments, the mean cellular hemoglobin content as a function of the age of the cells in a sample can be determined. A change in the cellular hemoglobin content is indicative of the presence of or the status of a disease such as anemia. In embodiments, a decrease in cellular hemoglobin content is indicative of anemia. In other embodiments, a change in cellular hemoglobin content at a particular age of the cells is indicative of a bleed or a transfusion event within the last 100 to about 120 days. In embodiments, for a transfusion event, the mean cellular hemoglobin can be increased. In embodiments, a decrease in cellular hemoglobin content is indicative of a bleed.

In embodiments, the systems and/or computer readable media can be contained within a flow cytometer or as a stand alone product. In embodiments, the systems and/or computer readable media can be contained in a kit for measuring HbA1c of a cell sample. Computer readable media is non-transitory media, and does not include transitory signals.

Figure 10:
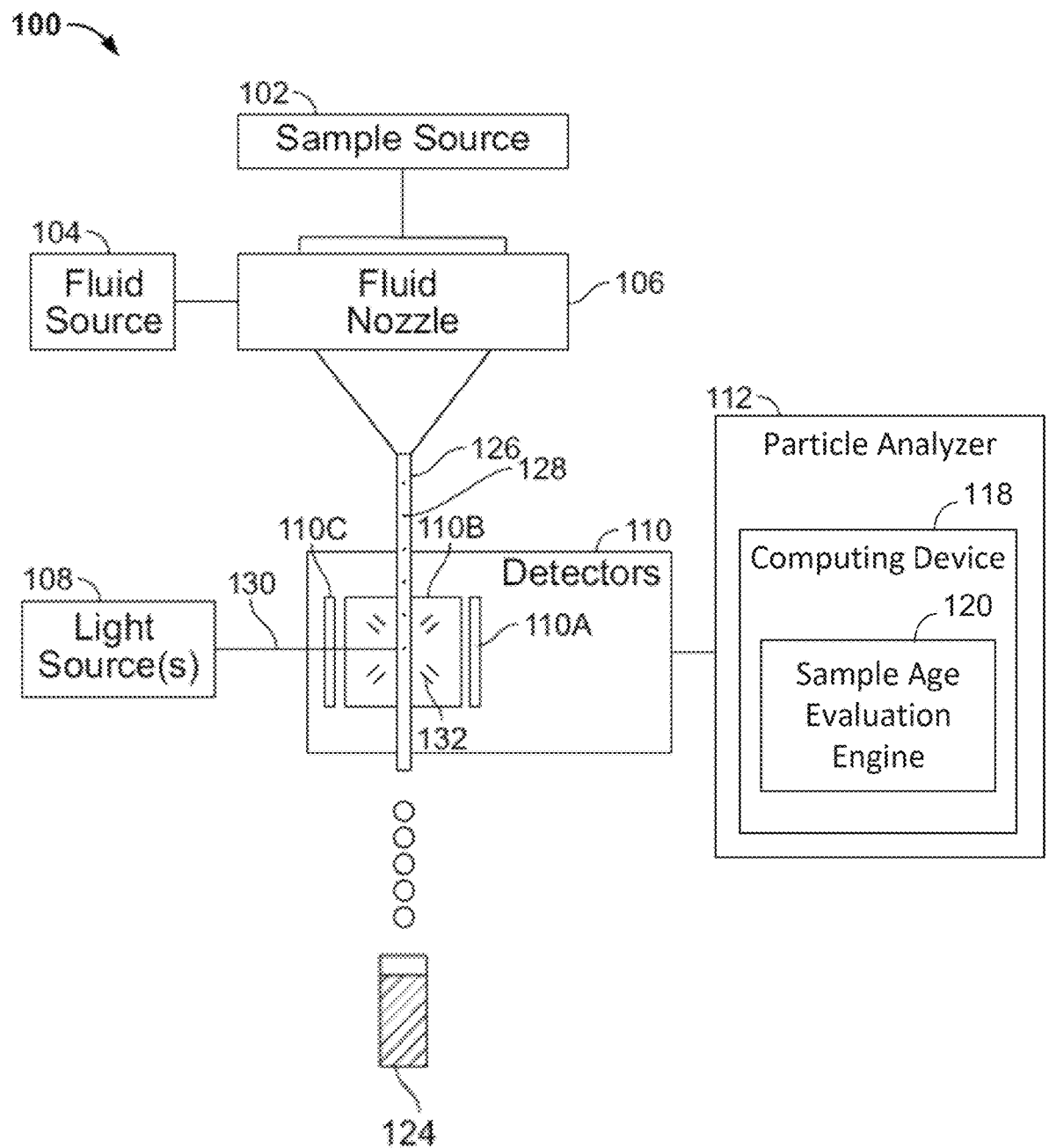
FIG. 10 is a schematic block diagram illustrating an example of a flow cytometer.
Figure 11:
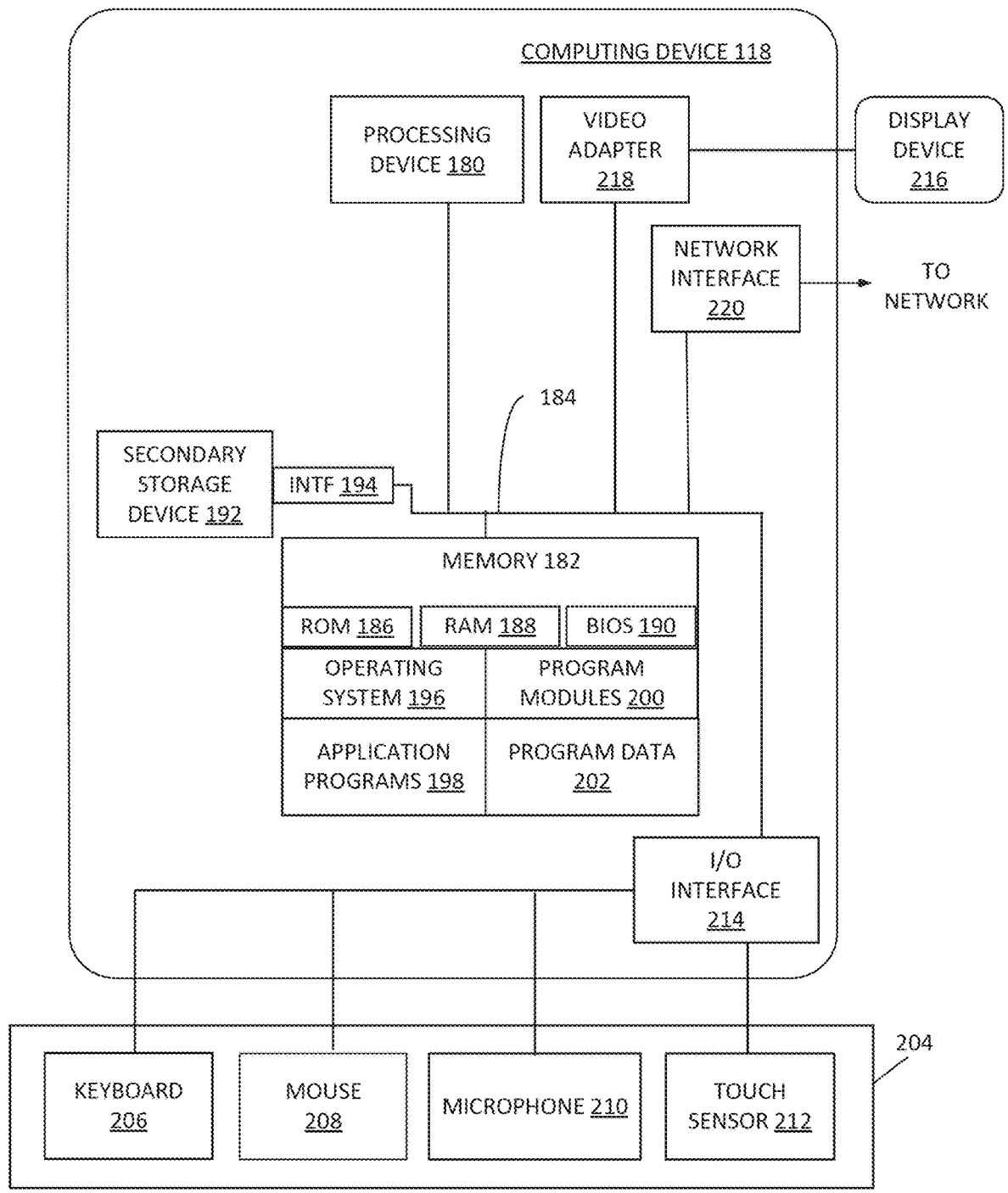
FIG. 11 is illustrates an exemplary architecture of a computing device that can be used to implement aspects of a sorting flow cytometer.
Figure 15:
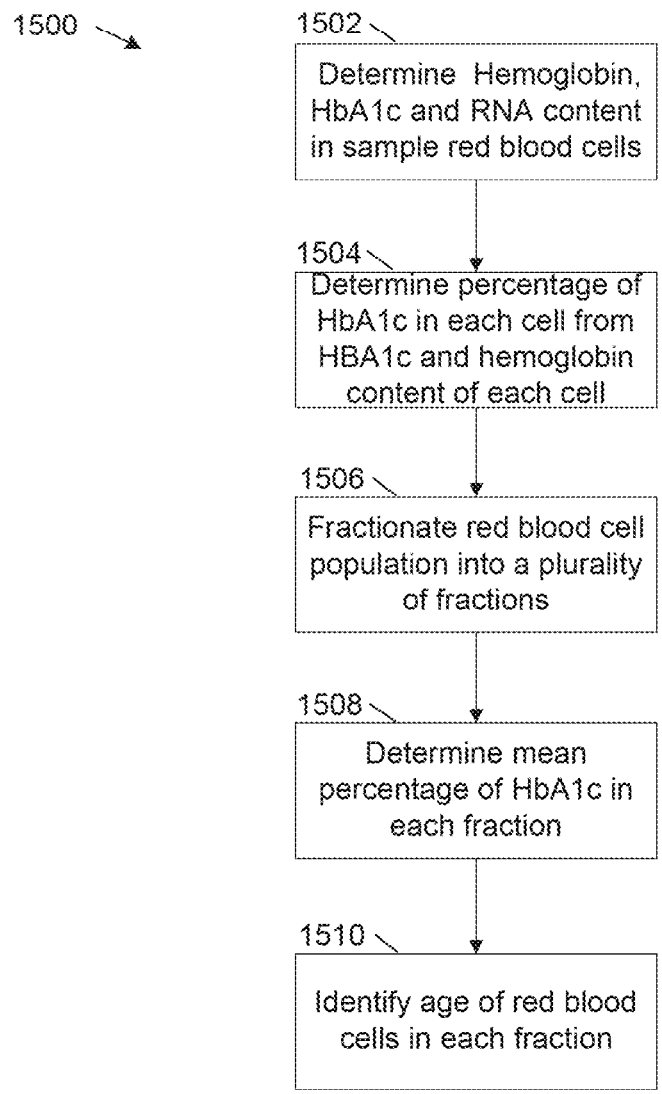
FIG. 15 illustrates a flowchart of an exemplary method as described herein for determining the age of red blood cells in a sample.

Reference is made to FIGS. 10, 11, and 15 as exemplary embodiments of systems for implementing the methods as described herein.

FIG. 10 is a schematic block diagram illustrating an example of a flow cytometer 100. In this example, the flow cytometer includes a sample source 102, a fluid source 104, a fluid nozzle 106, a light source 108, detectors 110 (such as including detectors 110A, 110B, and 110C), a particle analyzer 112 including a computing device 118 and sample age evaluation engine 120, and a container 124. The fluid nozzle 106 generates a fluid stream 126 containing particles 128 therein, and the light source 108 generates a light beam 130. Radiated light 132 is generated when the light beam 130 intersects the fluid stream 126 and particles 128 contained therein. Other embodiments of the flow cytometer 100 include more, fewer, or different components than the example illustrated in FIG. 10.

The sample source 102 is the source of the sample that is provided to the flow cytometer for analysis. The sample includes the individual particles 128 that are illuminated by the light beam 130 and analyzed by the particle analyzer. As an example, the sample may be blood and the particles may be blood cells. The sample may be in the form of a prepared sample, such as a fluid containing permeated red blood cells, achieved by performing protocols described herein. The sample source 102 can include one or more containers, such as test tubes, that hold the sample to be analyzed. A fluid transfer system is provided in some embodiments, such as to aspirate the sample from the container and deliver the sample to the fluid nozzle 106.

The sample is typically injected into a sheath fluid within the flow cytometer, which is provided by a fluid source 104. An example of a sheath fluid is saline. An example of the fluid source 104 is a container storing saline therein, and a fluid transfer system operable to deliver the sheath fluid from the fluid source 104 to the fluid nozzle 106.

In some embodiments a fluid nozzle 106 is provided to generate the fluid stream 126 and to inject the particles 128 of the sample into the fluid stream. An example of a fluid nozzle 106 is a flow cell. The fluid nozzle 106 typically includes an aperture having a size selected to at least be larger than the sizes of particles of interest in the sample, but small enough to arrange the particles into a narrow stream. Ideally the particles are arranged in a single file or near single file arrangement so that a single particle, or a small number of particles (e.g., 1-3), can be passed through the light beam 130 at a time. In some embodiments the particles are focused using hydrodynamic, acoustic, or magnetic forces.

A light source 108 (which, as discussed herein, can include one or more light sources) generates at least one light beam that is directed toward the fluid stream 126. Examples of light sources 108 include a laser and an arc lamp. In some embodiments the light beam 130 passes through an optics assembly, such as to focus the light beam onto the fluid stream 126. In some embodiments the light beam is a laser beam.

The light beam 130 from the light source 108 intersects the fluid stream 126. The particles 128 contained in the light beam 130 disturb the light beam 130 and generate radiated light 132. The type and pattern of radiated light 132 depends upon the type and size of the particles 128, but the radiated light 132 can include forward scattered light, side scattered light, back scattered light, as well as fluorescent light (which occurs when light rays are absorbed and reemitted by the particle, which is detectable by the corresponding change in wavelength (i.e., color) of the light rays).

One or more detectors 110 are provided to detect radiated light 132. In this example, the detectors 110 include a detector 110A arranged to detect forward scatter and fluorescence, a detector 110B arranged to detect side scatter and fluorescence, and detector 110C arranged to detect back scatter and fluorescence. One example of a detector 110 is a photomultiplier.

The particle analyzer 112 operates to receive signals from the one or more detectors 110 to perform various operations to characterize the particles 128. In some embodiments the particle analyzer 112 includes the computing device 118 and the sample age evaluation engine 120. Examples of the computing device are described herein, including in FIG. 11. The sample age evaluation engine 120 operates to determine the age of cellular hemoglobin in a sample as described herein. In some embodiments the particle analyzer 112 also includes an analog to digital converter.

In some embodiments the flow cytometer 100 is a sorting flow cytometer, which operates to use the characterizations of the particles generated by the particle analyzer 112 to sort the particles 128. A sorting flow cytometer may include a sorting system comprising a sort controller, at least one sorting plate, and multiple containers. The sorting flow cytometer may operate to sort the particles of sample based on properties of the particles (such as the maturity of or hemoglobin content of red blood cells). As one example, the sort controller applies a positive, negative, or neutral charge to drops formed from the fluid stream based on the characterizations of the particles. In some embodiments the fluid nozzle is electrically coupled to charge generating electrical circuitry, which is controlled by the sort controller. When the drops pass through the charged sorting plates, the drops are deflected based on their respective charges toward one of the containers. A sorting flow cytometer will typically have at least two containers, and may have more than three containers as well. Typically one container is a waste container for unwanted particles or for fluid drops found to be contaminated with one or more particles.

FIG. 11 illustrates an exemplary architecture of a computing device that can be used to implement aspects of the present disclosure, including any of the one or more computing devices 118 that can be used within the flow cytometer 100. The computing device illustrated in FIG. 11 can be used to execute, with the processing device 180, the operating system, application programs, and software modules (including the software engines) described herein.

The computing device 118 includes, in some embodiments, at least one processing device 180, such as a central processing unit (CPU). A variety of processing devices are available from a variety of manufacturers, for example, Intel or Advanced Micro Devices. In this example, the computing device 118 also includes a system memory 182, and a system bus 184 that couples various system components including the system memory 182 to the processing device 180. The system bus 184 is one of any number of types of bus structures including a memory bus, or memory controller; a peripheral bus; and a local bus using any of a variety of bus architectures.

Examples of computing devices suitable for the computing device 118 include a desktop computer, a laptop computer, a tablet computer, a mobile computing device (such as a smart phone, an iPod® or iPad® (registered trademarks of Apple Inc.) mobile digital device, or other mobile devices), or other devices configured to process digital instructions.

The computing device illustrated in FIG. 11 is also an example of programmable electronics, which may include one or more such computing devices, and when multiple computing devices are included, such computing devices can be coupled together with a suitable data communication network so as to collectively perform the various functions, methods, or operations disclosed herein.

FIG. 15 illustrates an exemplary flow chart of a method of the disclosure that can be implemented on a computing device, including any of the one or more computing devices 118 that can be used within the flow cytometer 100. In embodiments, a computing device contains instructions for implementing a method that comprises determining hemoglobin, HbA1c, and RNA content of a blood sample (1502), determining percentage of HbA1c in each cell from HBA1c and hemoglobin content of each cell (1504), fractionating red blood cell population into a plurality of fractions (1506), determining mean percentage of HbA1c in each fraction (1508), and determining the age of red blood cells in each fraction (1510).

Methods

In one aspect of the disclosure, a relationship between the life-span of red blood cells, RNA parameters, and hemoglobin parameters owing to the reticulocytes provides for characterization of the age of the red blood cells in a sample from a subject. During the maturation of the reticulocytes, the RNA content gradually disappears, while the hemoglobin content rises to obtain a maximum. In a function of the product of RNA content and hemoglobin content, the decreasing RNA and the increasing hemoglobin will equilibrate each other and the value of the function will remain constant during the maturation of the reticulocytes. If both RNA and hemoglobin are low however, it means that the reticulocytes cannot reach a normal hemoglobin level at the time that the blood sample has been drawn. A link between the breakdown of red cells in the reticuloendothelial system and the synthesis of hemoglobin in the reticulocytes is established herein.

In one aspect of the present disclosure, cell by cell flow analysis permits the fractionation of cells into subpopulations with respect to at least one marker. In embodiments, the marker is HbA1c, hemoglobin, and/or RNA. The red cell population is suitable for fractionation into subpopulations of different ages. Other cells having an active nucleus are subject to proliferation or to renewal of their constituents. The red cell however loses its nucleus and its RNA and enters into a life-span of a determined length. Recently, techniques were developed to apply antibody staining into the interior of the red cells without destroying the entity of the cells. Staining with an anti-HbA1c antibody and measuring the amount of cellular hemoglobin, it is possible to determine the percentage of HbA1c per cell.

Since glucose is freely accessible to cells, is always present in the blood and the formation of HbA1c is irreversible (Amadori M., *Atti Accad. naz. Lincei,* 1925, 2, 337; 1929, 9, 68, 226; 1931, 13, 72, 195), the percentage of HbA1c is always rising and can be used as a measure of the age of the cells. Using HbA1c as an age marker, a zero point is defined as the point at which the immature red cell has produced half of its hemoglobin. Developing into a reticulocyte and into a mature red cell, the cells at the end of their life-span are finally cleared by the reticuloendothelial system in the liver, bone marrow and spleen. The life-span of the red cells is defined as the age of the longest living cells.

In another aspect of the disclosure, the HbA1c percentage of individual red cells is measured and the red cell events as obtained in a cytometer are reorganized on a scale of percentage HbA1c. Because of the relationship between percentage HbA1c and the age of the red cells, such a scale also represents the age of the cells. The maximum value of the scale on which cellular events are still found, corresponds to the life-span of the oldest red cells. In a first approach, a life-span value of 120 days is applied, which is generally used as the mean life-span of human red cells. However, in one of the embodiments of the disclosure, a life-span factor is measured using the hemoglobin content and the RNA content of immature circulating red blood cells (reticulocytes). It is shown that using these parameters a measure of the life-span of the red cells of an individual can be obtained.

The red cell events on the scale of cellular HbA1c percentage or age permit the placements of cursors to divide the cell population. The cellular events between the cursors are referred to as fractions. There are a defined number of cellular events in the fractions. The limits of these fractions are set depending on two factors; the rank order of the events on the axis and the numbers of cellular events on the axis. In this way, the HbA1c percentage of the different fractions is an independent parameter and can be used for the age calculation of the cells in the fractions. Corresponding fractions can be compared between different individuals of whom the red cells have been exposed to different glucose concentrations.

In embodiments, the fractions contain similar numbers of cells. The HbA1c percentage values are based on the position of the fraction limits. In embodiments, the age values are calculated using the mean values of the fractions. For the calculation of the age of the cells in a fraction it is of importance to first determine whether cells might be lacking from a fraction, due to mortality or to absence due to immobilization in a solid organ.

In one aspect of the disclosure, the differences between the HbA1c percentages of the fractions are divided by the differences of the mean of the fractions leading to a derived HbA1c value. Such a derived HbA1c percentage value is the change of the percentage of HbA1c percentage over a period of time and is a measure of the blood glucose concentration in an individual during such a period of time. From blood samples from non-diabetic individuals, the derived HbA1c percentage values of the fractions are constant.

In embodiments, the measurement and the calculation of age of the hemoglobin and of the derived HbA1c parameter of individual red cells or groups of red cells is completed in the context of the measurement and the calculation of all the other red cells of the blood sample. In the case of blood samples from diabetic individuals, the measurement and the calculation is completed in comparison of normal reference blood samples.

In another aspect of the embodiment, a comparison is made between the mean values and of the limit values of corresponding fractions from normal individuals and from diabetic individuals. This allows the measurement of the derived percentage of HbA1c of the fractions of the diabetic individuals. Comparing the derived HbA1c percentage values of fractions of different ages of diabetic subjects with the self-measured blood glucose concentrations over time of the same subjects, there is a similarity of the two patterns. Comparing the blood glucose concentrations registered by diabetic subjects over time, with the derived HbA1c percentage of the age fractions of a blood sample of the same subjects, validates the age measurement of the fractions.

In another aspect of the disclosure, life-span values of the red blood cells in a sample from each patient are determined providing a reflection of the blood glucose concentration over time and the derived HbA1c values of the age fractions. These individual life-span values show a correlation with parameters of the reticulocytes, notably a function of the hemoglobin content and the RNA content of these cells. Taking in account the life-span of the red cells calculated as a function of the parameters of the reticulocytes and the calculation of the relative age of the blood cell fractions with respect to the life-span, the age of the cellular hemoglobin of individual cells or groups of cells in a blood sample can be measured.

In another embodiment, the quotient of the HbA1c percentage of the oldest 10% fraction of the red cells of an individual and of the mean HbA1c percentage of the totality of its red cells can be taken as a function of the life span of the red cells. In another embodiment, the HbA1c percentage of the oldest fraction is of clinical interest (Zoungas S et al. Diabetologia. 2012 March; 55(3):636-43. doi: 10.1007/s00125-011-2404-1. Epub 2011 Dec. 21). The cells with highest HbA1c percentage are responsible for vascular complications.

In another aspect of the disclosure, the calculated age of individual red cells or groups of red cells can be combined with the derived HbA1c percentage of these cells or groups of cells from a blood sample and the combined data can be used to reconstruct the blood glucose concentration on a time scale undergone by a subject in the past.

Examples are provided of the application of combining the calculated age of groups of cells with the derived HbA1c percentage, with the cellular hemoglobin content and with the representation of red cells in the blood stream allowing a determination of whether cells are lacking from the blood stream due to absence in other organs or due to elimination or mortality. The application is however not limited to these examples, and the combination of the calculated age of individual cells or groups of cells with other parameters of these individual cells or groups of cells are an integral part of the disclosure.

In the different embodiments of the disclosure, the treatment of cytometric data is useful in methods to attribute an age of the hemoglobin of individual red cells or groups of red cells from a blood sample, to determine the length of the life-span of red cells from an individual, to determine the mean age of the red cells from a blood sample, to attribute an HbA1c percentage and the derived HbA1c percentage to groups of red cells from a blood sample, to attribute cellular hemoglobin content or mean cellular hemoglobin content to one or groups of red cells from a blood sample, to determine the representation of groups of red cells of hemoglobin of a certain age in the blood circulation as a percentage of the full representation of cells, which is 100% if no cells are absent due to mortality, elimination or absence of cells from the blood stream and if no temporary fluctuations in the production of red cells occur, or a combination of any of the above mentioned embodiments or of any of the above mentioned embodiments with any other parameter of the red cells.

Systems and methods to determine the age-time scale of red cells are useful in diagnosis and monitoring of diabetes and/or anemia. The system detects changes in blood that are rather sudden and can remember these changes on a time scale for a period of about 3-4 months. As the system detects a change of glucose that has occurred months ago, the system could also detect changes of the density of red cells after a certain time point. Similarly, changes of hemoglobin content can be detected at a time point.

In other embodiments, methods as described herein are useful in detecting bleeding or blood transfusion. In the case that a bleeding event has occurred two months ago, there would a breaking point in hemoglobin content at the two month time point. In the case of transfusion, transfused blood is detectable if a difference in hemoglobin content exists between donor and receiver blood. A breakpoint at the time of reception of the transfusion would be detectable.

Referring now to FIG. 15, in embodiments, a method comprises measuring HbA1c and hemoglobin of the individual red blood cells (operation 1502); determining the percentage of HbA1c from the HbA1c content and the hemoglobin content of the individual red blood cells (operation 1504); fractionating the red blood cell population into a plurality of fractions using the percentage of HbA1c for each individual red blood cell as compared to the mean HbA1c of a reference cell fraction, each fraction comprising a substantially equal number of red blood cells (operation 1506); determining the mean percentage of HbA1c in each fraction (operation 1508); and identifying the age of the individual blood cell by comparing the mean percentage of HbA1c to a mean percentage of HbA1c for a reference control fraction (operation 1510).

In embodiments, a method comprises measuring HbA1c and hemoglobin of the individual red blood cells; determining the percentage of HbA1c from the HbA1c content and the hemoglobin content of the individual red blood cells; fractionating the red blood cell population into a plurality of fractions using the percentage of HbA1c for each individual red blood cell as compared to the mean HbA1c of a reference cell fraction, each fraction comprising a substantially equal number of red blood cells; determining the mean percentage of HbA1c in each fraction; and identifying the age of the individual blood cell by comparing the mean percentage of HbA1c to a mean percentage of HbA1c for a reference control fraction. In embodiments, HbA1c and/or hemoglobin of the red blood cells is measured in a flow cytometer. In other embodiments, a method further comprises determining the density of the red blood cells in the sample belonging to a fraction of a certain HbA1c percentage as compared to the fraction of the reference control cells. In embodiments, the reference control cells have a mean age of at least 28 days.

In embodiments, the method further comprises measuring RNA content of the individual cells in a sample. In embodiments, the reference cell fraction is the reticulocyte fraction. In embodiments, the proportion of cells that are reticulocytes is determined by staining with a dye that binds RNA, such as acridine orange.

In embodiments, the HbA1c in the individual cells can be determined by binding with a detectably labelled antibody that binds to an HbA1c or variant thereof. In embodiments, the detectable label is a fluorescent moiety that is detectable at a different wavelength than the side scatter and/or the dye that binds RNA.

In embodiments, cellular hemoglobin can be measured by side scatter as described in U.S. Pat. No. 7,541,190, which is hereby incorporated by reference.

In embodiments, the percentage HbA1c in individual cells is determined by dividing the HbA1c fluorescence by the side scatter (e.g. FL4/SS). In various embodiments, corrections to the percentage HbA1c are made in order to account for back ground. In other embodiments, the percentage HbA1c is converted to the percentage IFCC HbA1c using formula II.

In embodiments, the value of the percentage HbA1c for individual cells is fractionated into fractions. In embodiments, the fractions are determined by reference to the mean percentage of HbA1c of the reticulocyte fraction. In embodiments, the sample is divided into at least 10 fractions, each fraction having about the same number of cells.

In embodiments, the mean percentage of HbA1c in each fraction is determined, the age of the blood cell in the fraction is determined by comparing the mean percentage of HbA1c to a mean percentage of the fraction to HbA1c for a reference control fraction as corrected by a life span factor. In embodiments, the reference control fraction is an internal control cell population having a known HbA1c content.

In one embodiment of the present disclosure a method is described to relate the increase of the percentage of HbA1c in individual red cells, measured by flow cytometry, with the age of the hemoglobin in these red cells. Instead of measuring the time needed for an increase of percentage of HbA1c in individual cells, the method provides rearrangement of the cellular events, measured by the flow cytometer, on a scale of raising HbA1c percentage. The raise of HbA1c percentage can be related to a time scale. In embodiments, the total length of the time scale is about the life-span of the red cells. In embodiments, the life span is about 1 to 200 days, about 10-200 days, about 50-200 days, and about 100-200 days.

In another embodiment, the rearrangement of the cellular events on a scale of increasing time is independent from the speed of the raise of HbA1c percentage in these cells. A method of the disclosure provides expression of an increase or decrease of percentage HbA1c as a relationship to time independent from the percentage HbA1c value of an individual cell and provides an expression of HbA1c percentage as a function of time. This independence from variations in HbA1c formation or glucose concentration and the independence from variations in the hemoglobin content of the cells provides for analysis of sample suspected of or having a pathology or disease state.

In one embodiment of the present disclosure, a method is described to detect or monitor the progression of diabetes comprising measuring HbA1c, hemoglobin and optionally, RNA of the individual red blood cells from a subject with diabetes; determining the percentage of HbA1c from the HbA1c content and the hemoglobin content of the individual red blood cells; fractionating a red blood cell population into a plurality of fractions using the percentage of HbA1c of each individual red blood cell as compared to the mean percentage of HbA1c of the reticulocyte fraction, each fraction comprising a substantially equal number of red blood cells; determining the mean percentage of HbA1c in each fraction, identifying the age of the red blood cells in the fraction by comparing the mean percentage of HbA1c to a mean percentage of HbA1c for a reference control fraction, determining the mean age of the red blood cells in the sample from the subject with diabetes or suspected to have diabetes and comparing the mean age of red blood cells of the sample to mean age of the red blood cells of a sample from a normal subject. In embodiments, the control cell population is red blood cells obtained from subjects without the disease or condition, such as without diabetes. In embodiments, the reference control fraction has a known percentage of HbA1c as described in U.S. Pat. No. 7,968,279.

In one embodiment of the present disclosure, a method is described to detect and/or monitor the progression of anemia comprising measuring HbA1c, hemoglobin and optionally, RNA of the individual red blood cells from a subject with anemia; determining the percentage of HbA1c from the HbA1c content and the hemoglobin content of the individual red blood cells; fractionating a red blood cell population into a plurality of fractions using the percentage of HbA1c of each individual red blood cell as compared to the mean percentage of HbA1c of the reticulocyte fraction, each fraction comprising a substantially equal number of red blood cells; determining the mean percentage of HbA1c in each fraction, identifying the age of the red blood cells in the fraction by comparing the mean percentage of HbA1c to a mean percentage of HbA1c for a reference control fraction, determining the mean cellular hemoglobin for each age fraction of the sample from the subject with anemia and determining whether there is a difference in the mean cellular hemoglobin in different age fractions. In embodiments, the reference control fraction has a known percentage of HbA1c as described in U.S. Pat. No. 7,968,279.

In embodiments, the mean cellular hemoglobin content as a function of the age of the cells in a sample can be determined. A change in the cellular hemoglobin content is indicative of a disease such as anemia. In embodiments, a decrease in cellular hemoglobin content is indicative of anemia. In other embodiments, a change in cellular hemoglobin content at a particular age of the cells is indicative of a bleed or a transfusion event within the last 100 to about 120 days. In embodiments, for a transfusion event, the mean cellular hemoglobin can be increased. In embodiments a decrease in cellular hemoglobin content is indicative of a bleed.

In another embodiment the disclosure includes a modification of the function that provides a correlation between HbA1c percentage values obtained by flow cytometry technique on the total of the red cells and reference laboratory techniques. The modified function provides a similar correlation, but implies an extension of the range of measurement from the range of about 5 percent to 15 percent which is suitable for whole blood values of about 0 percent to 25 percent which is expressed by individual cells in the different samples.

In another embodiment of the disclosure, instead of measuring HbA1c percentage values of individual cells, the mean HbA1c percentage values of fractions of the total cell population are calculated. These fractions or subpopulations of cells are selected on the basis of a raise in HbA1c percentage. The disclosure provides transformation of the mean HbA1c percentage of the fractions into time values of the fractions.

In another embodiment a reference is created to determine a basic time scale. The reference includes the data of blood samples from a number of normal subjects, of which it can be assumed that they have stable blood glucose levels and a normal regular raise of HbA1c percentage. Applying a constant increase of HbA1c percentage a basic time template is constructed which can be used as a reference to calculate time scales from other subject samples.

In another embodiment the basic time template obtained from the normal samples is applied to other samples from subjects. In embodiments, a number of corrections were needed. The corrections include: 1) a calculation of the correct position of an HbA1c percentage mean value of a subpopulation of cells on a time scale, and/or 2) a correction based on the condition of the reticulocytes and/or the lifespan of the red cells. In embodiments, after the application of the corrections, time scales are constructed applicable to other patients or normal subjects.

In another embodiment, once a time scale has been constructed, the raise of HbA1c percentage (derivative of HbA1c percentage values) between the respective fractions or subpopulations can be plotted against the time points on the curve. In this way the speed of formation of HbA1c is visualized. Since in an in vivo situation, the speed of HbA1c formation depends on the concentration of blood glucose, there is a relationship between these differential HbA1c percentage curves and blood glucose curves.

In another embodiment of the disclosure involves the determination of red blood cell age in diabetic subjects. Upon the drawing of the blood, these subjects have presented the results of blood glucose measurements one or several times per day. The results of several months of monitoring are expressed on a glucose/time curve and compared to a curve representing the differential percentage HbA1c values/time obtained from the cytometric data of the blood samples of the same subjects. Comparison of the data provides a method to measure the age of cellular hemoglobin.

In another embodiment of the disclosure, time data is used to express cellular hemoglobin content as a function of time. In another embodiment of the disclosure, the methods described herein are useful in a method to determine the mean age and the life-span of red blood cells of a subject. In another embodiment of the disclosure, the percentage of cells represented in the blood sample is a measure of the absence of cells being immobilized in organs or the mortality of the red cells of a subject by natural clearing or by pathologic processes.

Cell Processing

In one embodiment, according to the method described herein, whole blood red cells are stabilized and permeated and stained with a fluorescence-labelled anti-HbA1c antibody emitting at a certain wavelength (e.g 675 nm, FL4) and with a RNA marker emitting at another wavelength (e.g. 525 nm, FL1). The cells are analysed in a flow cytometer equipped with a side scatter (SS) multiplier tube and are presented on an axis representing FL4/SS (FIG. 1b), which is a measure for the percentage of HbA1c, for example as described in U.S. Pat. No. 7,968,279. The reticulocytes are separated by RNA staining (FL1) and on the basis of a low HbA1c content.

In embodiments, to calculate the correct HbA1c percentages and cellular hemoglobin content, reference control cells with a known HbA1c percentage value were added to the samples as described in U.S. Pat. No. 7,968,279. The reference control is typically made of fluorescent particles with known hemoglobin concentration, or equivalent hemoglobin concentration, known side scatter and fluorescence intensities. These typically include, but are not limited to, synthetic particles, human or animal blood cells, and processed human or animal blood cells. Upon calibration, quantitative measurement of cellular HbA1c, i.e., the absolute amount of this hemoglobin variant in the individual red blood cell can be achieved on the flow cytometer.

Background values of HbA1c antibody were measured for reticulocytes and mature red cells using an isotypic control antibody or by adding in the assay a glycated HbA1c peptide, blocking the HbA1c reactivity of the antibody. Antibodies specific for HbA1c are known or commercially available. Such antibodies can be readily labelled using detectable labels, in particular those labels detectable by flow cytometry.

In embodiments, cells are permeable to the marker, (e.g. detectably labelled antibodies specific for HbA1c). The blood sample is treated with a cell permeabilization and stabilization reagent capable of permeating the cellular membrane of red blood cells, which enables the penetration of intracellular markers into the red blood cell for cellular analysis. The cell permeabilization and stabilization reagent also induces precipitation and/or aggregation of intracellular proteins within the cellular membrane but preserves the cellular constituents, such as intracellular and cell surface antigen sites, DNA and RNA molecules, and cytoskeleton elements.

The term "cellular constituent" includes cellular components inside the cellular membrane, and on the surface of the cellular membrane such as cell surface antigen sites. The term "intracellular constituent" refers to a cellular component inside the cellular membrane, which includes, but is not limited to, intracellular proteins, such as hemoglobin and hemoglobin variants inside erythrocytes, cytoskeleton elements, and DNA and RNA. The cytoskeleton elements include, but are not limited to, tubulin and spectrin.

In embodiments, the cell permeabilization and stabilization reagent comprises:

N-acyl sarcosine or a salt thereof represented by the following molecular structure: $R_1$—CO—N(CH$_3$)CH$_2$COOX$_1$, wherein $R_1$ is an alkyl or alkylene group having 8 to 18 carbon atoms, and $X_1$ is H, Na$^+$, or K$^+$;

a pH adjusting agent to adjust pH of the reagent less than 7; and an aqueous medium.

N-acyl sarcosine, in a free acid form, and the salt thereof are commercially available. It is preferred to use the free acid form, which does not introduce metal ions into the reagent. N-acyl sarcosine in a free acid form is not water soluble. It can be pre-dissolved in an ethanol solution, and then added into the aqueous solution. As the pH of the reagent is adjusted between 4 and 6 by the pH adjusting agent, the N-acyl sarcosine is in the form of anion in the solution.

Suitable examples of N-acyl sarcosine include N-oleoyl sarcosine, N-stearoyl sarcosine, N-lauroyl sarcosine, N-myristoyl sarcosine, N-cocoyl sarcosine, and salts thereof. In embodiments, the alkyl or alkylene group of $R_1$ has 12 carbon atoms. In one preferred embodiment, N-lauroyl sarcosine is used.

In embodiments, once the cells are labelled they are analysed on a flow cytometer for the presence of one or more markers such as HbA1c and/or RNA using gating at particular wavelengths.

In embodiments, a kit is provided for determining the age profile of a population of red blood cells in a sample comprises: a) an antibody or antigen binding fragment thereof that specifically binds HbA1C or a variant thereof; b) a dye that specifically binds to RNA; and c) a red blood cell reference control sample. In some embodiments, the red blood cell reference control fraction has known percentage of HbA1C. In other embodiments, the reference control cell is a normal control sample such as from a subject not having diabetes or anemia. In other embodiments, the reference control cell is from a subject having diabetes with a known HbA1C value. In embodiments, the antibody or antigen binding fragment is detectably labelled. In embodiments, the dye that specifically binds to RNA is acridine orange. In embodiments, the kit can further comprise a reagent for permeabilizing red blood cells. In embodiments, a kit further comprises a computer readable medium providing for a determination of the age and/or density of red blood cells in a sample.

Data Analysis

In embodiments, a method comprises measuring side scatter and fluorescence of the individual red blood cells with a flow cytometer; determining the hemoglobin content of the individual red blood cells by the side scatter; deriving an HbA1c content from the measured fluorescence of the individual red blood cells; and determining the percentage of HbA1c from the HbA1c content and the hemoglobin content of the red blood cells; fractionating the red blood cell population into a plurality of fractions using the percentage of HbA1c of the individual cells as compared to a reference cell fraction (e.g. reticulocytes), each fraction comprising a substantially equal number of red blood cells; determining the mean percentage of HbA1c in each fraction, and identifying the age of the red blood cell by comparing the mean percentage of HbA1c to a mean percentage of HbA1c for a reference control fraction.

In embodiments, mean corpuscular hemoglobin (MCH) is calculated using the internal control cells, for example including the following steps: (a) mixing an aliquot of a blood sample with a permeation reagent to form a first sample mixture; and incubating the first sample mixture for a first period of time sufficient to permeate cellular membrane of red blood cells and to cause hemoglobin aggregation within the cells; (b) adding a neutralization reagent to the first sample mixture to form a second sample mixture, and incubating the second sample mixture for a second period of time sufficient to inhibit further reactions of the permeation reagent with the red blood cells; and (c) performing a cell-by-cell measurement of side scatter signals of the red blood cells in the second sample mixture on a flow cytometer; and (d) obtaining cellular hemoglobin (Hgb$_{cell}$) of the red blood cells using the side scatter signals obtained from the measurement. In embodiments, the mean corpuscular hemoglobin (MCH) was obtained for each of the blood samples from the red cell index reported by the analyzer. It is noted that on the hematology analyzer, MCH (picogram) was calculated from the total hemoglobin concentration (Hgb, gram/deciliter) of a lysed blood sample and the red blood cell count (RBC, number/liter) of the blood sample.

In embodiments, the correlations of the obtained mean side scatter values from both aliquots of the samples to the MCH obtained on the hematology analyzer were analyzed separately. Upon obtaining cellular hemoglobin, the total hemoglobin concentration of the blood sample can be obtained by multiplying $Hgb_{cell}$ by the red blood cell count. The latter can be obtained either independently, or together with the measurement described above if the flow cytometric instrument has a fluid volume measuring device to facilitate the counting.

In embodiments, determining the percentage of HbA1c from the HbA1c content and the hemoglobin content of each of the individual red blood cells is determined by dividing the HbA1c content and the hemoglobin content (e.g. FL4/SS). In embodiments one or more corrections may be applied to correct the percentage of HbA1c. In embodiments, the normalized FL4/SS data were transformed using the formula $$y = c * e^{0.157 * x}$$

in which y are the transformed data, x are the normalized FL4/SS data and c is a constant (e.g. 2.74). This function however does not go through the origin. Although useful for correction of HbA1c percentage values, approximately varying between 5% and 15%, it was replaced for the purpose of the fractions in our analysis varying from approximately 0% to 25%. For the replacing function, a general form was chosen;

$$y = c * (e^{a*x} - e^{b*x}) * (d + e^{-f*x})$$

The values of the constants were empirically determined by comparison with glucose values as shown below. Exemplary values of the constants are a=0.03, b=−0.01, c=15.1, d=1.8, e=2.71828 (Euler's constant or the base of natural logarithms), f=1.8. The first part of the replacing formula makes the curve go through the origin; the second part introduces a slight reverse sigmoid curve in the section of the lower values of the curve. This type of standard curve has been observed frequently in solid phase immune assays (c.f. Ekins, R. P. Radioimmunoassay and Related Procedures in Medicine IAEA, Vienna, 1974, STI/PUB/350, pp 91-121). The replacing formula (2) is as corrective as (1) in the correlation, having $R^2$ values of 0.95 and 0.94 respectively.

In embodiments, to calculate the age and the percentage of HbA1c of each individual cell in a blood sample, in embodiments, the following factors are preferably known:
(1) The kinetics of the binding of an HbA1c marker to the HbA1c molecule
(2) The glucose concentration during the life-span of the cell
(3) The length of the life-span of the cells.
(4) The kinetics of HbA1c formation.

In embodiments, reference HbA1c percentage values are converted from the current NGPS values into the new IFCC values according to published instructions (David B. Sacks for the ADA/EASD/IDF working group of the HbA1c assay; Clinical Chemistry. 2005; 51: 681-683.). The new IFCC values differ from the NGSP values by having no intercept with respect to a zero value and are therefore more suitable in which low values of the young cells are included. Considering the binding of the antibody as a first order reaction responding to a logarithmic function, the reverse, an exponential formula was applied to the cytometric data, resulting in a linear correlation with a regression line passing through the origin of the diagram.

Antibody Binding Kinetics;

$$x = \frac{\{\ln(y + c1) - \ln(c1)\}}{c2}$$

reverse; $y = c_1 * (e^{x*c2} - 1)$

In which y is the HbA1c percentage given by the reference laboratory in IFCC units, x is the cytometric HbA1c percentage determined in the presence of an internal reference and $c_1$ and $c_2$ are constants.

In other embodiments, the red cell events on the scale of cellular HbA1c percentage or age permit the placements of cursors to divide the cell population. The cellular events between the cursors are referred to as fractions. There are a defined number of cellular events in the fractions. In embodiments, the fractions contain similar numbers of cells. The HbA1c percentage values are based on the position of the fraction limits. In embodiments, the age values are calculated using the mean values of the fractions. For the calculation of the age of the cells in a fraction it is of primary importance to first determine whether cells might be lacking from a fraction, due to mortality or to absence due to immobilization in a solid organ.

In embodiments, fractionation of the cells involves using the mean value of the percentage of HbA1c of reticulocytes present in the sample as the fraction limit value. In embodiments the cells are divided into at least 10 fractions. In an embodiment, the fraction limit of the last fraction 10 was estimated to be the mean fluorescence value of the last fraction 10 plus half of the difference between the fraction limit values of fractions 8 and 9. The values were corrected for background and compensation of fluorescence.

In one aspect of the disclosure, the differences between the HbA1c percentages of the fractions are divided by the differences of the mean of the fractions leading to a derived HbA1c value. Such a derived HbA1c percentage value is the change of the percentage of HbA1c percentage over a period of time and is a measure of the blood glucose concentration in an individual during such a period of time. From blood samples from non-diabetic individuals, the derived HbA1c percentage values of the fractions are constant.

In some embodiments, fraction limit values are expressed in preliminary IFCC percentage HbA1c as shown in Table 1. Each fraction limit value in column b was divided by the mean value of column b. The resulting value was multiplied with the mean IFCC HbA1c percentage value of 3.44 of the samples. Fraction limit values expressed in IFCC percentage HbA1c. The values of column d were obtained from the values of column c, using Formula (VIII);

$$(d) = 4.54 * (e^{0.157 * (c)} - 1)$$

Fraction size in HbA1c percentage=fraction (n)−fraction (n−1) from column d.

In embodiments, on the basis of the establishment of the above mentioned factors, and using a reference consisting of six normal blood samples, a time axis was constructed. The HbA1c percentage limit values of the fractions were used as arbitrary age or time units and a reaction curve was constructed. The derivative of the reaction curve is a horizontal line representing the constant rate of HbA1c formation as expected at a constant glucose concentration and under the assumptions described above (FIG. 3D). As can be observed from FIG. 3E, the sizes of the fractions on the time scale are irregular and differ substantially between each other. This is likely due to the fact that red cells of certain ages are absent from the circulation for different reasons.

Figure 1B:
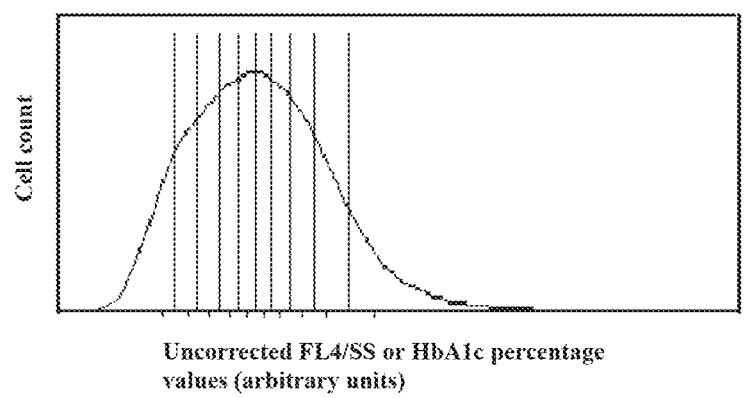

The strategy used in one aspect of the disclosure is to compare groups (fractions) of red cells from the blood sample that belong to different age segments to determine if there are fluctuations in the representation of cells of such groups. These fluctuations can occur for reasons of mortality, elimination or for being away from the circulation in organs like bone marrow, spleen etc, of for fluctuations in the number of produced cells during a certain period. In an ideal model, red blood cells are in an environment of constant glucose concentration, HbA1c is formed at a constant rate, the cells are formed at a constant rate, all cells are destroyed after the same life-span and no further mortality or hiding of cells outside of the blood circulation occurs. In such situation, the representation of cells in the fractions is referred to as 100%. In such a sample, fractions analyzed as shown in FIG. 1B, having equal amounts of cells in them will show a constant raise of HbA1c percentage per fraction and all fractions will have a constant size. When, with respect to the ideal model, cells are missing from a given fraction, the fraction size will augment with a factor that is 100% of cells in a fraction from an ideal sample divided by the percentage of represented cells in a given fraction from a sample.

Using the formula VIII above, and maintaining the assumptions of constant glucose concentration and linear kinetics of HbA1c formation, the percentage of representing cells in a fraction can be calculated. The fractions in the beginning of the age axis, where cells are young, are large, presumably because cells are hiding in bone marrow or spleen before being released in the blood stream. At the end of the axis, the fractions are large presumably because the old cells are subjected to elimination. In (FIG. 3F), the percentages of represented cells are plotted on the age axis. The value of the smallest fraction was taken to be 100%. The pattern responds to the general expectation that at least during a considerable time the red cells are fully represented in the blood stream and not yet subjected to elimination.

In embodiments, the approach was taken to analyze the representation of cells in the blood samples. Using these conditions the fluctuation of cell numbers appeared to be as one that is generally accepted as normal in a normal individual, providing a strong indication that the chosen conditions are correct (see Example 3, FIG. 3F).

In the calculation of the time axis as described above, a constant glucose concentration undergone by the blood was a condition. In the case of a diabetic blood sample, variations of glucose concentration have to be taken into account. The division of the cellular events into ten fractions as described is not dependent on glucose concentration or cellular hemoglobin, so corresponding fractions from normal and diabetic samples can be compared.

The values of the fraction limits can change when changes in glucose concentration or changes in percentage of representing cells occur. Changes in glucose concentration can have a different effect on the HbA1c percentage versus time plot than changes in percentage of representing cells. The time axis is derived from the HbA1c percentage axis as described in, for example, Example 3.

Figure 4A:
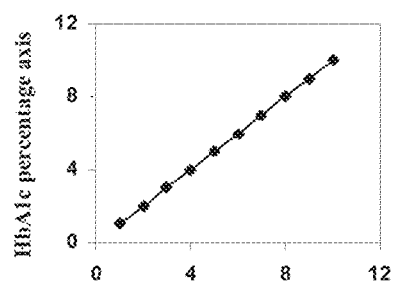
FIG. 4 provides graphical representations of simulation of the effect of a temporary rise in blood glucose concentration of an otherwise normal subject; (A); HbA1c curve of a normal subject as presented in FIG. 3B and determined as in example 3 and Table 1; (B); as in (A), but with a temporary rise in blood glucose concentration; (C); as in (B), but determined as described in example 5 and Table 3.
Figure 4B:
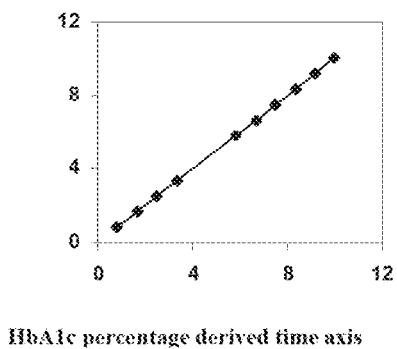

As illustrated in the simulation of FIGS. 4 and 4b, a change in HbA1c percentage or in percentage of representing cells in a fraction both produce a similar effect. The above described analysis shows that without introduction of new parameters it cannot be decided whether a change in a fraction limit value can be attributed to the time axis as should be done in case of a variation in percentage of representing cells or to the HbA1c percentage axis as should be done in case of a variation in glucose concentration.

The position of the mean value within a fraction is an indicator of the concentration of glucose undergone by the cells. Since the fractions and the rank order of the cells in the fractions are independent from the glucose concentration, a variation of the glucose concentration will shift the cells to the lower end of the fraction or to the higher end of the fraction in case of a decrease or an increase of the glucose concentration respectively. This variation affects the calculated mean HbA1c percentage value of the cellular events in the fraction. To compare the patient fractions with the reference fractions in view of the position of the mean, the reference fractions and the positions of their fraction limit values were adapted to the fractions of the patient (Example 5). Comparing the sizes of the fractions on the HbA1c percentage axis from samples from normal individuals with those from diabetic individuals and comparing also the mean HbA1c values with the adapted mean values of the reference within the fractions it is possible to calculate variations in the derived HbA1c percentage or the glucose concentrations.

Figure 4C:
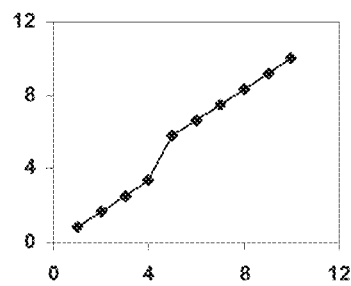

In the case of a patient fraction mean value being compared to the corresponding fraction mean value of the normal reference, a factor representing the ratio of the respective mean values was multiplied with the total cell mean HbA1c percentage of the patient. To compensate for the effect that a different HbA1c percentage has on the age calculation, the time segment represented by the fraction was divided by the same factor (Example 6). The result of such double correction is shown in FIG. 4c. The differences between the position of the mean values between fraction of normal samples and diabetic samples are small. A relationship to calculate the differential HbA1c values is presented in example 5.

To compare the mean blood glucose concentrations and the HbA1c percentage values in the time/age plots, a factor was introduced different for each patient to align the mean of the glucose concentration values with the adapted mean HbA1c percentage value (Example 7). Comparing the HbA1c percentage/age plots with the patient glucose/real time plots revealed a similarity. This similarity could be further improved by adapting the total range on the time axis of the HbA1c percentage plots (Example 8, FIG. 6). This adapted total range reflects the length of the life-span of the red cells of the different patients.

Figure 7:
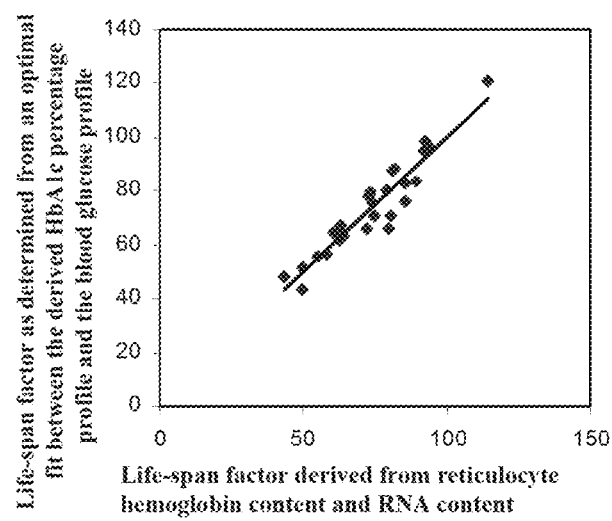
FIG. 7 is a graphical representation of the relationship of life-span factors. Ordinate; Life-span factor as determined from an optimal fit between the determined HbA1c percentage profile and the blood glucose profile. Abscissa; Life-span factor derived from reticulocyte hemoglobin content and RNA content. The determination of the life-span factor from hemoglobin and RNA content of the reticulocytes is shown in example 7 and table 2.

In embodiments, a correlation is found between the life-span of the red blood cells and the RNA parameters and hemoglobin parameters owing to the reticulocytes (Example 8, FIG. 7). Initially these parameters were sought in the older fractions of the samples. During the maturation of the reticulocytes, the RNA content gradually disappears, while the hemoglobin content rises to obtain a maximum. In a function of the product of RNA content and hemoglobin content, the decreasing RNA and the increasing hemoglobin will equilibrate each other and the value of the function remains constant during the maturation of the reticulocytes. If both RNA and hemoglobin are low however, the reticulocytes cannot reach a normal hemoglobin level at the time that the blood sample has been drawn. From the observations in example 8, there is a link between the breakdown of red cells in the reticuloendothelial system and the synthesis of hemoglobin in the reticulocytes. The recycling of iron can also play a major role in such a feedback mechanism.

The calculated age of the oldest fraction of a number of samples gave a mean value of approximately 100 days, which is shorter than the 120 days obtained with the chromium labelling technique. The cellular events on the HbA1c percentage scale extend into higher values, indicating that there are rare cells that obtain a very advanced age. The very sensitive chromium labelling technique might have taken into account these rare events. In embodiments, to estimate a life-span comparable to the life-span obtained with the chromium labelling technique, an extrapolation was applied to the curve of represented red blood cells in the blood circulation. The mean age of the red cells in individual samples was calculated as described in Example 10.

Figure 9:
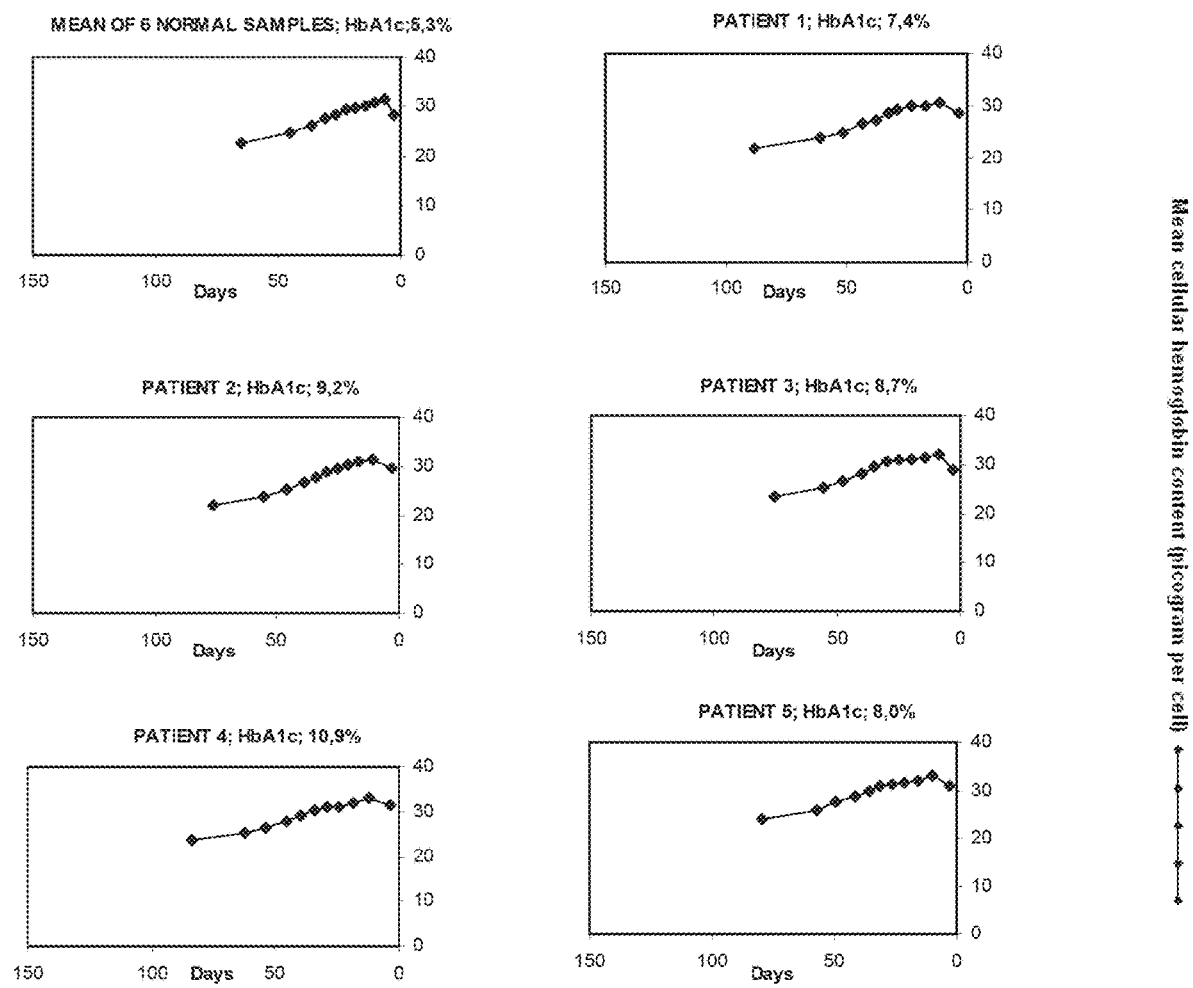
FIG. 9 shows graphical representations of time diagrams containing mean cellular hemoglobin content (MCH) of cells in the different age fractions of 26 subjects having diabetes and 6 normal subjects. The MCH was determined using the internal control cells. The age of the fractions was determined as shown in in example 6 and in table 2D column ad.
Figure 9:
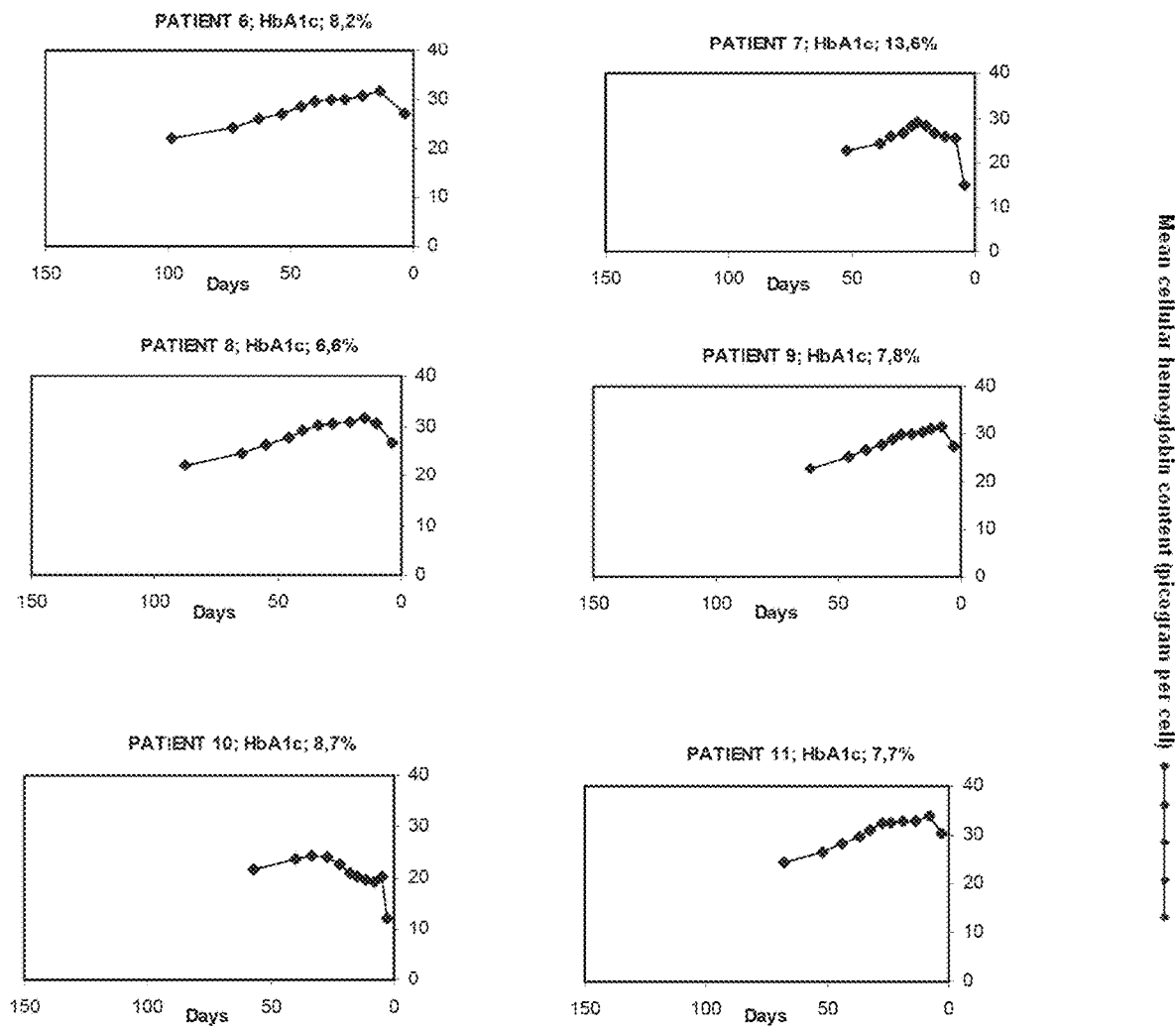
Figure 9:
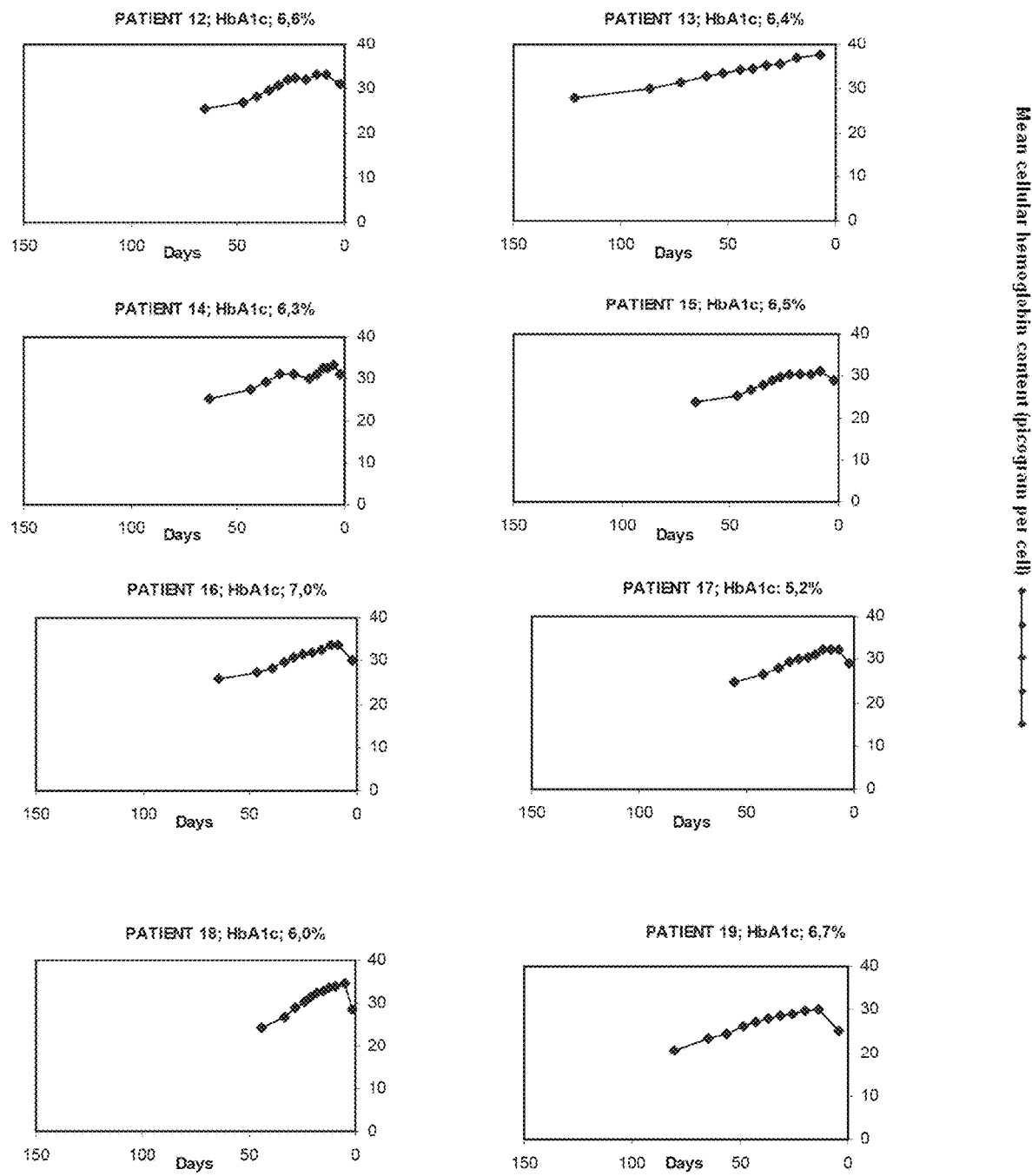
Figure 9:
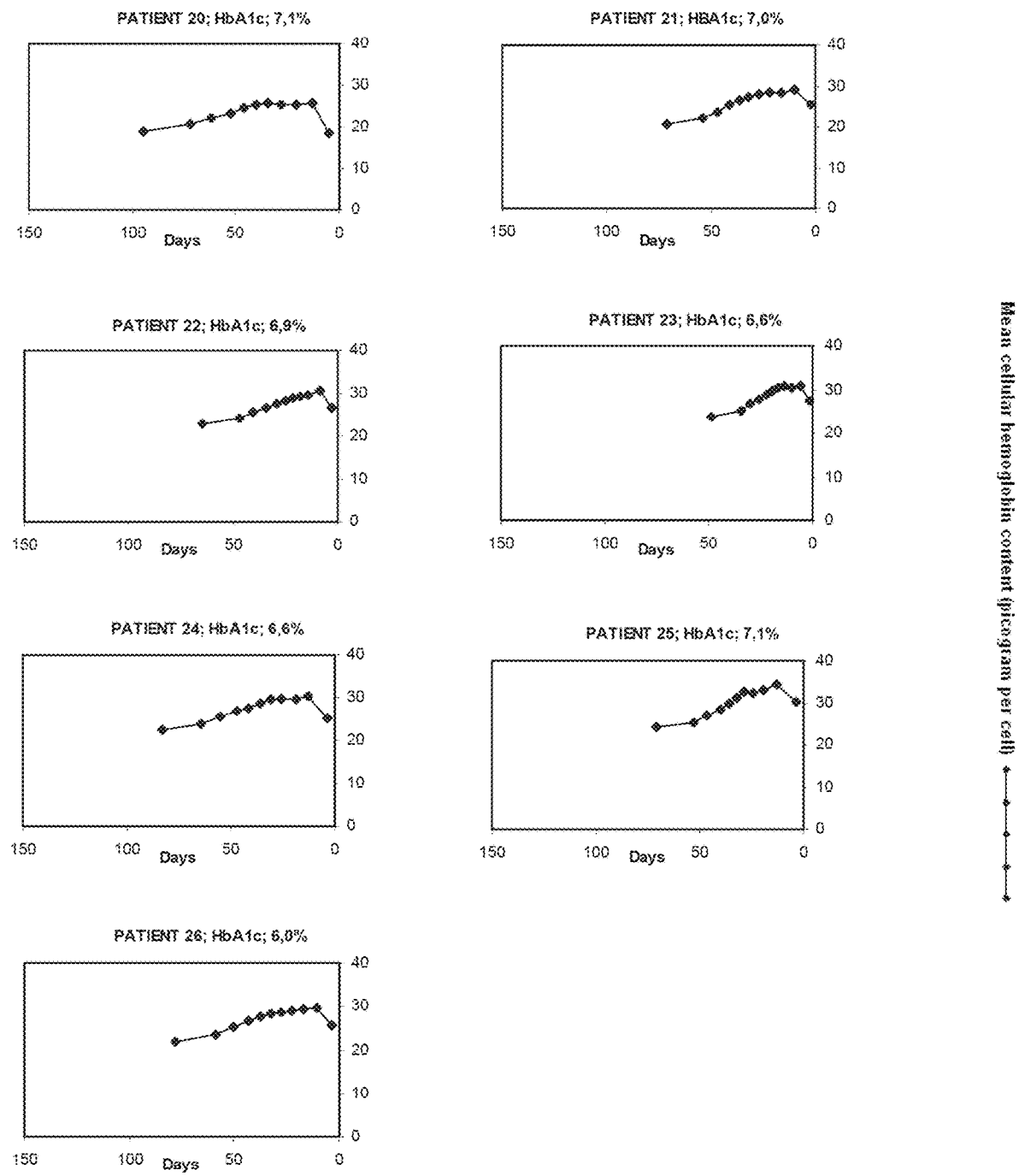

The determination of the age of the cells in the fractions of the analysis provides for application of a time axis to red blood cell parameters of choice. In the above analysis, mean cellular hemoglobin of the cellular age fractions was currently determined. In FIG. 9, these mean cellular hemoglobin curves are shown. Typically, hemoglobin reaches a maximum level in cells of 5 or 6 days of age. Aging further, the cells lose hemoglobin as reported (Gifford S C, Derganc J, Shevkoplyas S S, Yoshida T, Bitensky M W. Br J Haematol. 2006 November; 135(3): 395-404).

In embodiments, a method comprises a step of determining the age of the red blood cell fraction by comparing the mean percentage HbA1c of the fraction to a table providing the relationship between mean percentage HbA1c of the fraction and the age of the red blood cell. In embodiments, the method further comprises whether the sample contains a large fraction of cells older than a reference cell population, which is indicative of a disease state. In embodiments, the disease state is diabetes or anemia.

Example 1

An assay measuring cellular hemoglobin and the percentage of HbA1c of a blood sample and the fractionation of the cells into reticulocytes and ten fractions of mature red cells is described. Glucose and Hemoglobin react together irreversibly to form HbA1c (Amadori product). This reaction is a continuous phenomenon as a function of time and of glucose concentration. The formation of HbA1c is an element of control of the glycemic equilibrium of a diabetic patient. Normal value of HbA1c: 5% of total hemoglobin.
Materials and Methods.

The following materials were used in the assay:
1. A blood sample treated with 0.7 mM ethylenediamine tetraacetic acid (EDTA) as anticoagulant and stored for not more than ten days at 4° C.
2. Sphering reagent; an aqueous solution of 0.137M sodium chloride, 0.005M HEPES, 0.0005M (D+) trehalose, 0.083M formaldehyde, 0.04 mM n-dodecyl beta-D-maltoside, 0.5 ml/l of Proclin-300, 0.5 mg/l of acridine orange and a quantity of sodium hydroxide to obtain a pH of 7.5
3. Permeation reagent; an aqueous solution of 2.03 mM of N-lauroyl sarcosine, 10 mM of succinic acid, 0.22M of sucrose, 0.015 mM bovine serum albumin, 0.5 ml/l of Proclin-300 and a quantity of pyrrolidine to adjust the pH to 5.4.
4. Neutralization reagent; an aqueous solution of 40 mM of HEPES, 0.5M of sodium chloride, 0.91 mM of bovine serum albumin, 0.03M of sodium azide, a quantity of sodium hydroxide to adjust the pH at 7.25, and a monoclonal anti-HbA1c antibody (IgG1) covalently conjugated to fluorescence dye Alexa Fluor® (Life Technologies) 647 at a concentration of 5 mg/l.
5. Fixation reagent; an aqueous solution of 0.155M of sodium chloride, 0.04M of sodium phosphate, 0.18M of boric acid, 0.01M of EGTA, 0.016 μM of dextran sulphate (MW 500,000), 0.62M of formaldehyde and a quantity of sodium hydroxide or hydrochloric acid to adjust the pH at 7.1.
6. A thawed sample of labelled reference control cells.

An exemplary method involves placing a blood sample in a single tube. The blood sample was diluted with acridine orange. The cells were fixed and incubated with a permeation agent. Control cells were then added to the tube. Fluorescently labelled anti HbA1c antibody (antibody as described in U.S. Pat. No. 7,541,190) was added to the tube. Fluorescent antibody/cells were fixed and then measured by cytometry.
Labelling and Analysis Volumes of 4 μl of different blood samples were each suspended in 200 μl of sphering reagent. After 1 minute of incubation, 3 μl of the suspension was subsequently mixed with 60 μl of the permeation reagent. After 1.5 minutes of incubation, 5 μl of labelled reference control cells were added and mixed and after 1 minute of incubation, 100 μl of neutralization reagent was added and mixed. After another 10 minutes of incubation, 80 μl of fixation reagent was added.

The final sample mixture was analyzed on a FC500 MPL cytometer by side scatter (SS) measurement and measurement of fluorescence at 525 nm (FL1) and at 675 nm (FL4). An analysis of a representative sample from a normal subject is shown in FIG. 1A. Total cellular hemoglobin was measured by side scatter. HbA1c was measured by determination of fluorescent label. The % HbA1c is calculated by dividing the fluorescent value by the side scatter value and multiplying by 100.
Results The sample list mode data as provided by the cytometer software were analysed further using an algorithm program that provides a parameter of fluorescence (FL4) divided by side scatter (SS). Regions A, B and C (FIG. 1A) were automatically gated and analyzed separately. Region A; control cells from a diabetic patient, Region B; Red blood cell reticulocytes, Region C; red blood mature cells.

The red cell population minus reticulocytes on the percentage HbA1c axis was fractionated into ten fractions containing approximately equal numbers of cells (FIGS. 1A and B). The mean values of each fraction were given for FL4 and side scatter by the cytometer-linked computer program. FL4 was compensated for overflow of fluorescence in each channel and the background of FL4 as determined as described above was adapted to each fraction by multiplying with the ratio of the SS of the fractions and the total mean SS (as determined by FL1), the background was taken as proportional to the side scatter values of the cells in the different fractions.

The side scatter of the red cells is a measure for the cellular hemoglobin content (MCH) of the cells. The MCH of a sample could therefore be derived from the mean side scatter values measured by the cytometer. The HbA1c content of the sample could be derived from the mean of the fluorescence of the cells at 675 nm (FL4) measured by the cytometer. A background value was subtracted. The background value was obtained by running the assay with samples in the absence of the anti-HbA1c$_{antibody}$ and presence of a nonspecific isotypic control monoclonal antibody (IgG1) covalently conjugated to fluorescence dye Fluor Alexa 647. A measure for the percentage of HbA1c in arbitrary units was obtained by dividing the HbA1c content by the hemoglobin content of red cells or of a sample. In a first instance such measure was obtained by the simple division; FL4/SS.

Figure 1C:
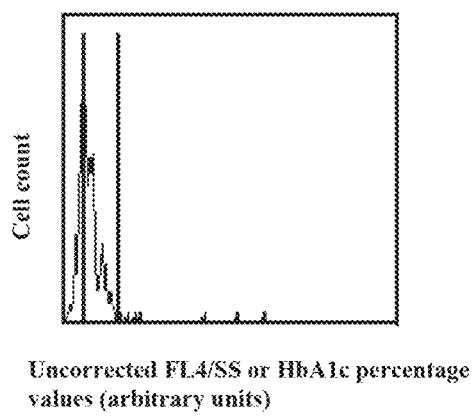

The reticulocytes were analyzed separately. As shown in FIG. 1C, the RNA containing cells (FIG. 1A, region B) having a low FL4 value were separated from contaminating cells having a high FL4 value. The fraction of pure reticulocytes was measured. The fraction limit and the mean value in FL4/SS units, the FL1 value in arbitrary units and the SS value in arbitrary units were determined.

Example 2

Comparison of Correlation Plots of HbA1c Percentage Data from a Reference Laboratory Using Three Different Determinations and of HbA1c Percentage Data Obtained with the Flow Cytometric Procedure.

The HbA1c percentage was determined by a reference laboratory on 120 samples using three different methods of HbA1c determination; (Primus Ultra2: affinity chromatography, Roche Unimate: immunoturbidimetry, and Tosoh G7 variant: cation-exchange chromatography). Cytometric HbA1c percentage values were determined in the presence of reference control cells having a known percentage of HbA1c. The conversion of arbitrary HbA1c percentage units into percentage HbA1c values is described herein.

Methods and Results

Figure 2A:
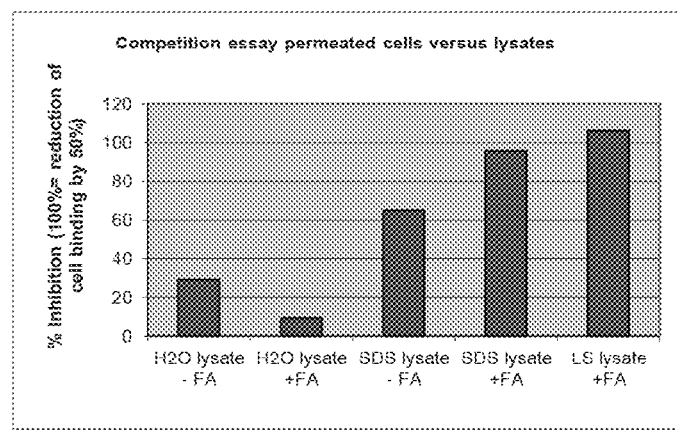
FIG. 2 (A) is a graphical representation of the percentage inhibition of anti-HbA1c antibody binding to permeated red cells by different blood lysates.
Figure 12A:
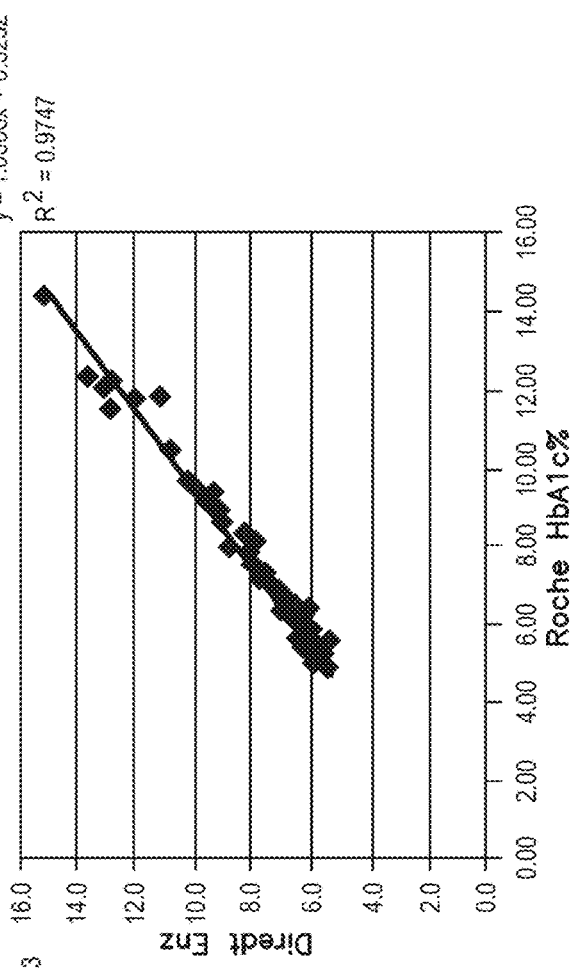
FIG. 12A shows a graph of cytometric % HbA1C values of 120 blood samples according to example 2 compared to % HbA1C reference lab values using Tosoh G7 cation-exchange chromatography test. The correlation factor $R^2=0.9604$.
Figure 12B:
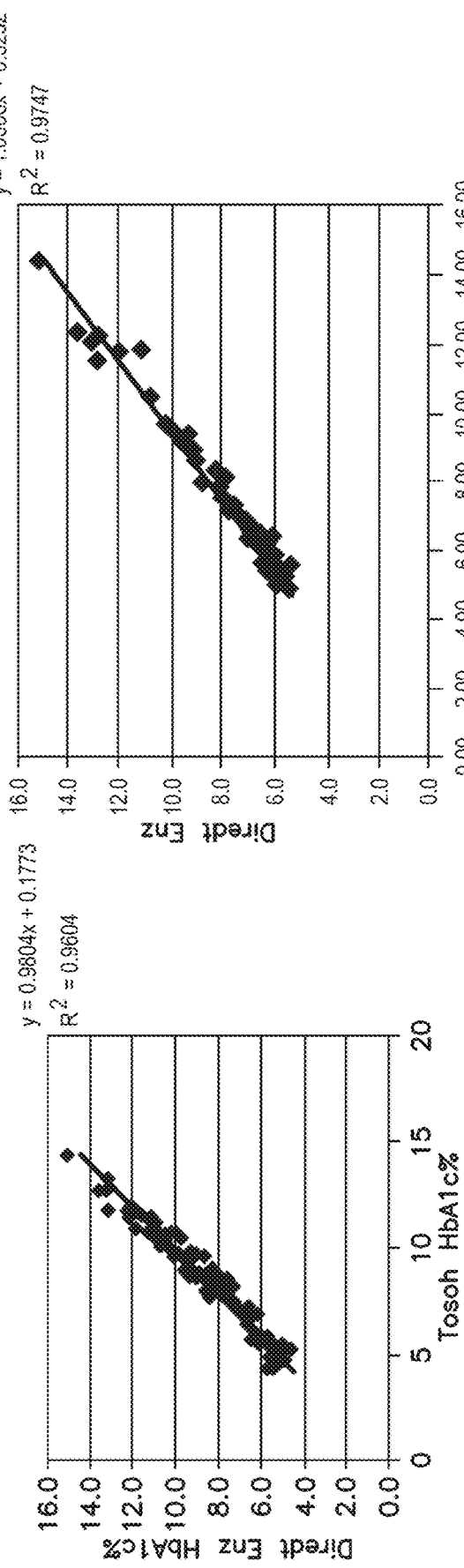
FIG. 12B shows a graph of cytometric % HbA1C values of 120 blood samples according to example 2 compared to % HbA1C reference lab values using Roche Unimate immunoturbidimetry test. The correlation factor $R^2=0.9747$
Figure 12C:
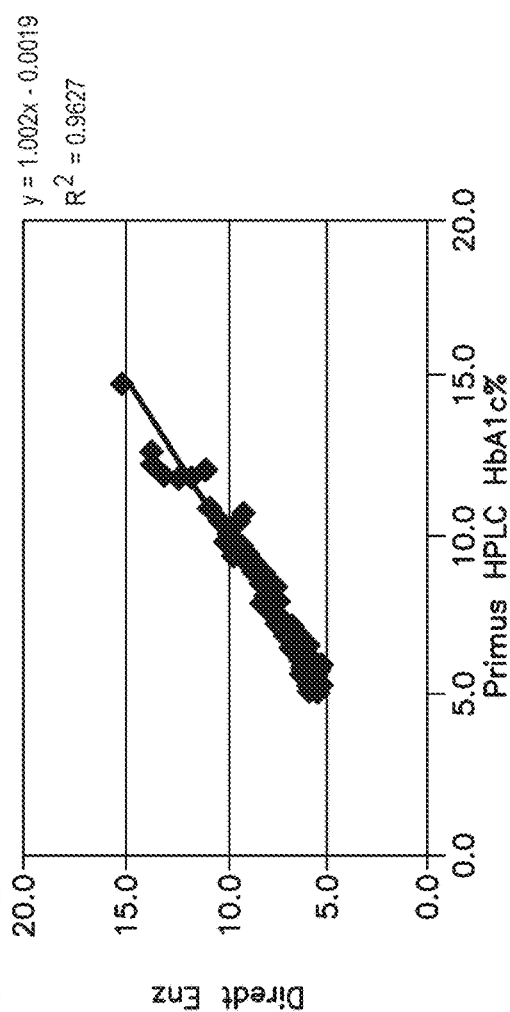
FIG. 12C shows a graph of cytometric % HbA1C values of 120 blood samples according to example 2 compared to the % HbA1C reference lab values using Primus HPLC test. The correlation factor $R^2=0.9627$.
Figure 13A:
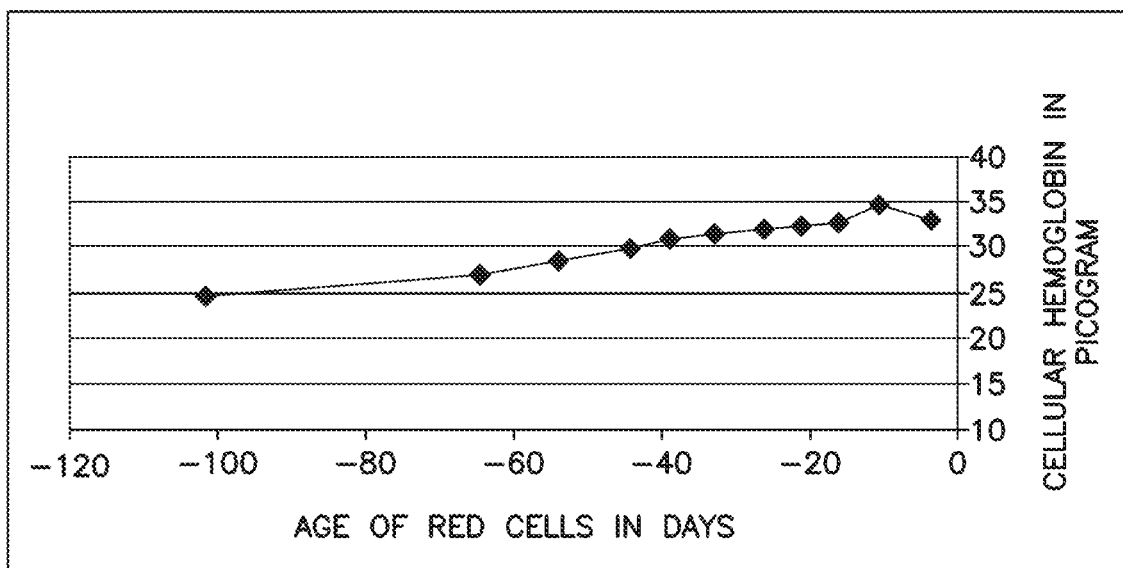
FIG. 13A shows a graph of mean cellular hemoglobin in picograms in each fraction per age of red blood cells in each fraction in days in a single blood sample.
Figure 13B:
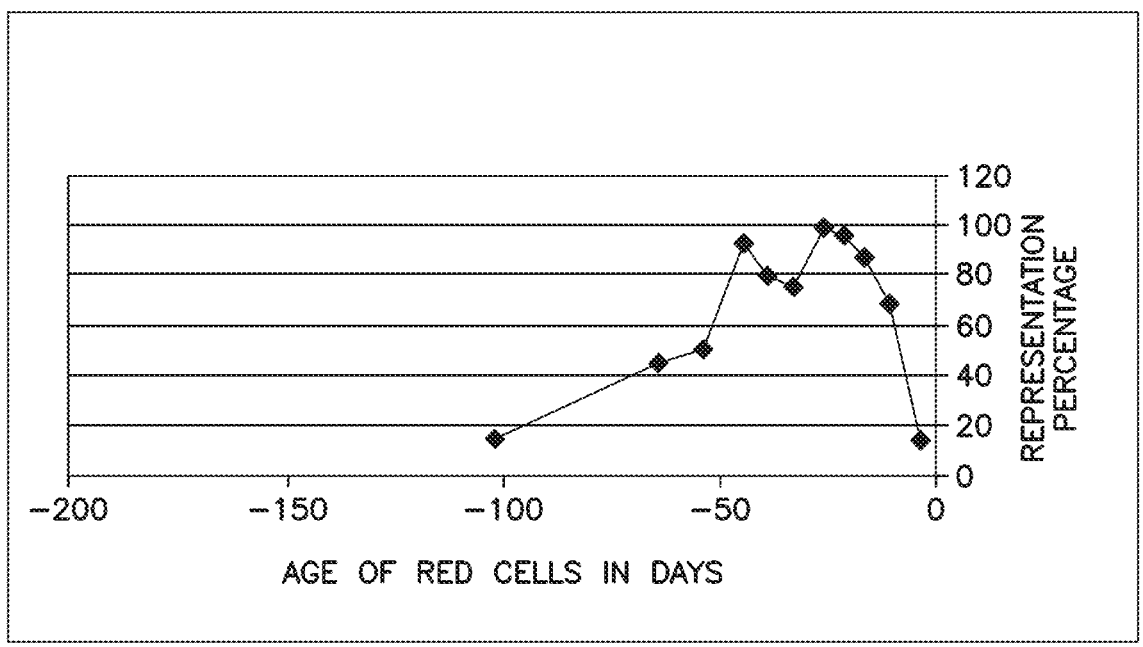
FIG. 13B shows a graph of percentage of represented cells in a fraction per the age of red blood cells in each fraction in days in a single blood sample.
Figure 13C:
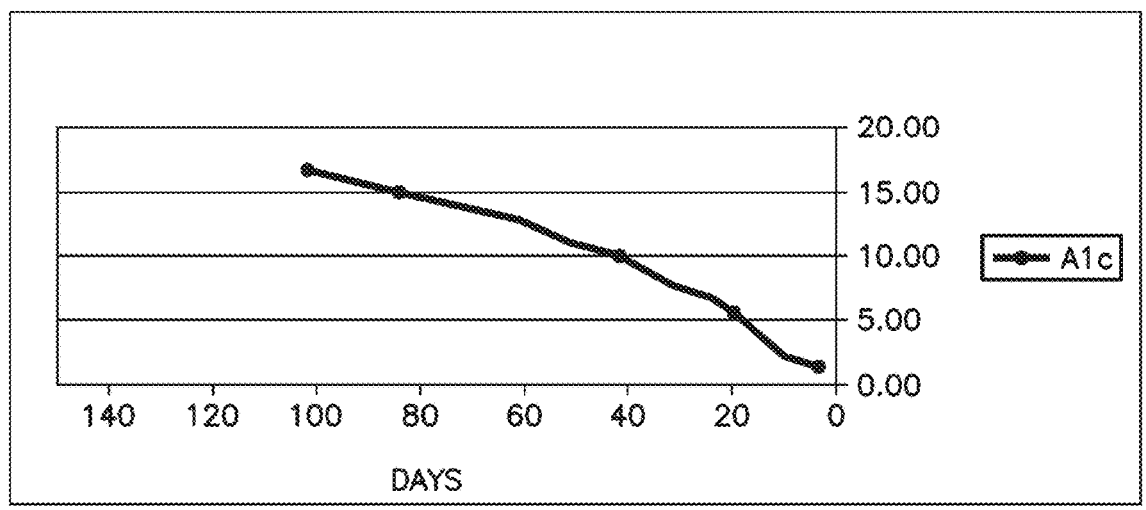
FIG. 13C shows a graph of HbA1c percentage in each fraction per age of red blood cells in each fraction in days in a single blood sample.
Figure 13D:
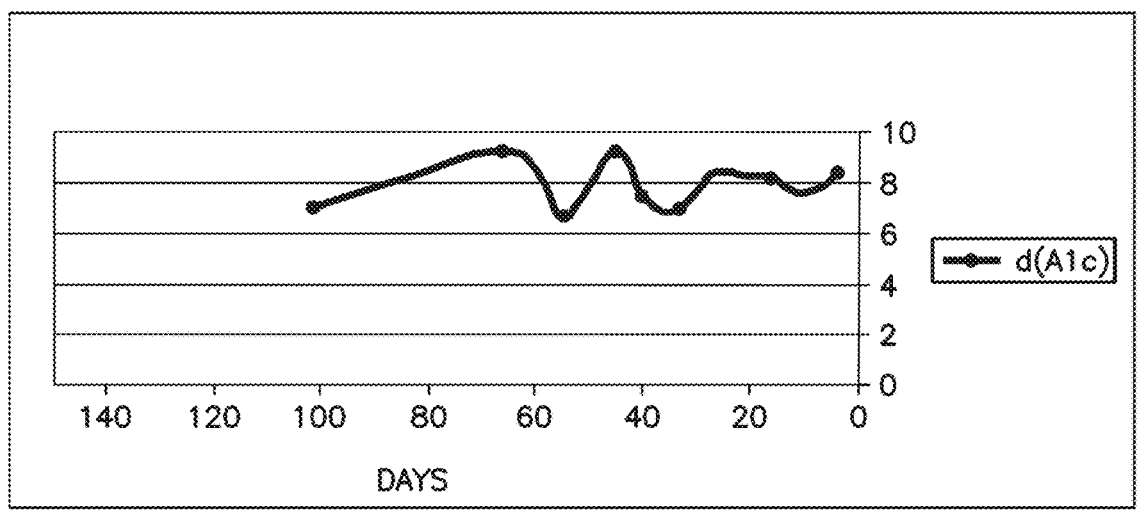
FIG. 13D shows a graph of derived HbA1C percentage in each fraction per age of red blood cells in each fraction in days in a single blood sample.
Figure 13E:
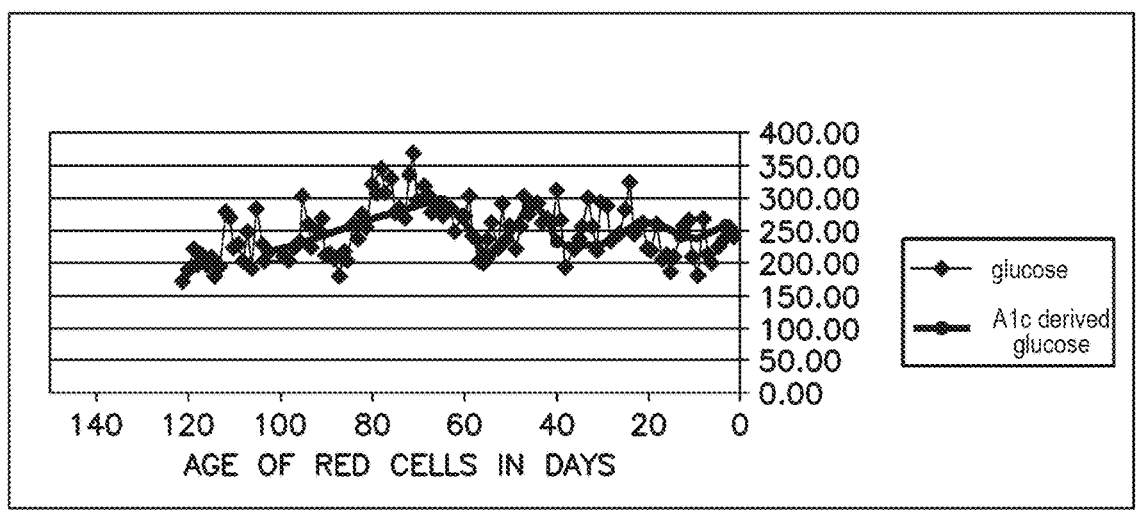
FIG. 13E shows a graph of blood glucose and adapted derived HbA1C compared to age of red blood cells in days in a single blood sample.

In a first instance, we showed that HbA1c molecules within the fixed red cells were freely accessible by the fluorescent labelled antibodies. Red cells were formaldehyde fixed and lysed in water and further disintegrated in the presence of detergents. The lysates were used in a competition experiment with equal amounts of HbA1c in the lysates and in the permeated red cells. Using antibody at non-saturating conditions, the lysates were inhibiting and the lysate that was formaldehyde fixed and treated with lauroyl sarcosine similarly as the HbA1c in the cells, was inhibiting antibody binding at 50%, showing that the anti-HbA1c antibody has free access to the HbA1c molecules in the cells (FIG. 2A). The percentage of HbA1c of a sample was calculated dividing the HbA1c content of the sample by the mean cellular hemoglobin content of the sample. By comparison to the known value of MCH and HbA1c percentage of reference control cells that were mixed with the sample, the MHC and HbA1c percentage could be determined. 120 samples were obtained from a reference laboratory. Of each sample the reference laboratory had measured the HbA1c percentage value using three different assays. (FIG. 12)

The HbA1c percentage values provided by the reference laboratory were expressed according to the NGSP standardization. Comparison of the NGSP HbA1c percentage values with mean glucose concentration values of patients and normal individuals shows an intercept of 2.15 percent with the origin of a correlation curve. Very low HbA1c percentage values are found in the younger fractions of cells. Therefore, the HbA1c percentage values according to the IFCC standardization were used, showing no intercept in an HbA1c percentage versus mean glucose concentration correlation curve and reflecting a more rational HbA1c percentage. A conversion formula:

$$\text{NGSP}=(0.915*\text{IFCC})+2.15 \quad \text{(Formula IX)}$$

is provided in the literature (David B. Sacks for the ADA/EASD/IDF working group of the HbA1c assay. Clinical Chemistry, 2005; 51: 681-683.)

Figure 2B:
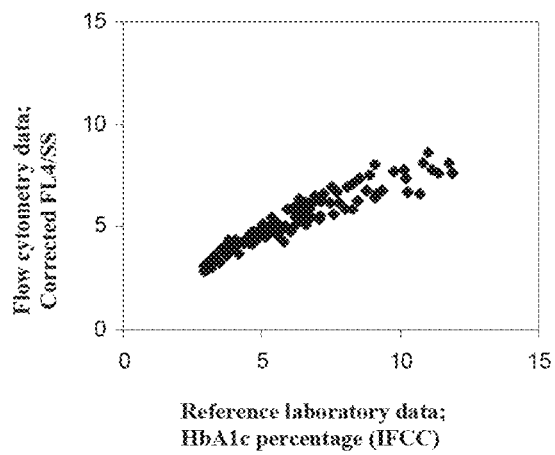

After conversion into IFCC HbA1c percentage values of the internal reference control cells and of the values provided by the reference laboratory, a correlation curve was constructed as presented in FIG. 2B. Analysis of the curve revealed a logarithmic function as expected for a first order reaction. Conversion of the cytometric arbitrary HbA1c percentage values using the following formula:

$$\text{IFCC HbA1c percentage}=4.54*(e^{0.157*\text{cytometric arbitrary HbA1c percentage}}-1) \quad \text{(Formula X)}$$

resulted in a linear correlation curve with a slope of 1, an $R^2$ of 0.9 and passing through the origin (FIG. 2B). For blood samples or for groups of cells this formula is used to calculate IFCC HbA1c percentage values.

The kinetics of the binding of an anti-HbA1c antibody as used in the assay was determined from the data of a previously published correlation experiment, for example as described in U.S. Pat. No. 7,968,279, in which 120 samples were analysed simultaneously by a reference laboratory and by cytometric analysis as described. The reference HbA1c percentage values from this experiment, provided by a reference laboratory, were converted from the current NGPS values into the new IFCC values according to published instructions (David B. Sacks for the ADA/EASD/IDF working group of the HbA1c assay; Clinical Chemistry. 2005; 51: 681-683.). The new IFCC values differ from the NGPS values by having no intercept with respect to a zero value and are therefore more suitable for our studies in which low values of the young cells are included. The resulting correlation is shown in FIG. 2B.

Figure 2C:
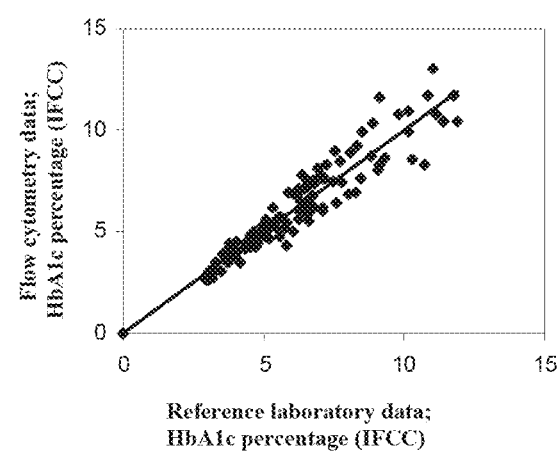

Considering the binding of the antibody as a first order reaction responding to a logarithmic function, the reverse, an exponential formula was applied to the cytometric data, resulting in a linear correlation with a regression line passing through the origin of the diagram (FIG. 2c).

Antibody Binding Kinetics:

$$x = \frac{\{\ln(y+c1) - \ln(c1)\}}{c2} \quad \text{(Formula VII)}$$

$$\text{reverse; } y = c_1 * (e^{x*c2} - 1)$$

In which y is the HbA1c percentage given by the reference laboratory in IFCC units, x is the cytometric HbA1c percentage determined in the presence of an internal reference control cells and $c_1$ and $c_2$ are constants. The binding kinetics of the anti-HbA1c antibody was calculated and was used throughout the study.

In FIG. 2C, the normalized FL4/SS data were transformed using the formula $$y = c * e^{0.157*x} \quad \text{(formula 1)}$$

in which y are the transformed data, x are the normalized FL4/SS data and c is a constant (2.74). The correlation factor $R^2=0.94$.

Example 3

Data from Six Normal Subjects; Representation of FL4/SS Values and Corrected FL4/SS Values in the Different Fractions and Transformation of Percentage of HbA1c in the Fractions into Time.

This example provides data from six normal subjects and conversion of fraction limit FL4/SS values into time. For reason of comparison with blood samples from diabetic individuals, in a first approach, blood samples were chosen representing normal non-diabetic individuals supposed to have undergone a constant blood glucose concentration. To further ascertain that the parameters obtained from the normal samples represent a constant blood glucose concentration, the mean of the parameters of 6 normal samples were taken.

As described in example 1, raw data, produced by the cytometer were used to fractionate mature cell populations into fractions containing equal amounts of cells. The organization of the cells on the HbA1c percentage axis (FIG. 1B) is depending on the augmentation of the HbA1c percentage of the cells. Whether this augmentation is fast, slow or irregular has no influence on the rank order of the cellular events on the axis. Only an augmentation that is zero or negative will profoundly disturb the organization. This is however impossible because of glucose being always present in the blood and of the irreversibility of the Amadori reaction leading to the HbA1c complex. As described below, the calculation of the sizes of the fractions on the FL4/SS axis will be based on data supplied by a reference sample. The calculated HbA1c percentage values of other samples can therefore be applied to the fractions without modification. The stability of the rank order of the cells makes the technique also feasible for the analysis of samples from diabetic subject or subjects with haematological abnormalities.

The HbA1c percentage value of these samples was determined by cytometric analysis. The derived HbA1c percentage value, supposed to be constant, was given the value of the HbA1c percentage.

Methods and Results

Blood samples from six normal subjects were processed and analyzed according to Example 1.

In an ideal model, red blood cells are in an environment of constant glucose concentration, HbA1c is formed at a constant rate, the cells are formed at a constant rate, all cells are destroyed after the same life-span of 120 days and no further mortality or hiding of cells outside of the blood circulation occurs. In such a sample, fractions analysed as shown in FIG. 1b, having equal amounts of cells in them, will show a constant raise of HbA1c percentage per fraction. In such a model, the segments on the FL4/SS or HbA1c percentage axis in FIG. 1b, should be of equal size. The sample of FIG. 1b is taken from normal subjects (example 3) in an effort to approach an ideal model. The reason that the segments in FIG. 1b are not of equal size can be imputed to differences between the properties of the sample used, and any of the properties of an ideal sample as outlined above. Using samples from haematologically normal subjects without diabetes, it was assumed that the segment distribution of FIG. 1b finds its origin in the different life spans of individual cells and the hiding of cells outside of the blood from which the sample was taken. With respect to the ideal model, missing cells by mortality or hiding, expressed as the percentage of cells represented in the blood stream, will increase the fraction size on the HbA1c percentage axis as in FIG. 1b. Taking into account the conditions in which FIG. 1b was constructed, the relationship is; (percentage of represented cells in a fraction)=1/(fraction size on the HbA1c percentage scale).

Figure 3A:
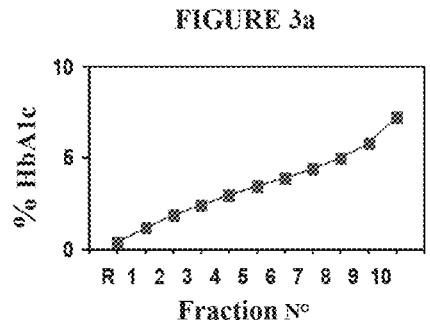
FIG. 3 (A) is a graphical representation of IFCC HbA1c percentage per fraction. FL4/SS fractions from normal human subjects were obtained as described in example 3 and analysed as shown in FIG. 1. The fractions are as shown in Table 1 and have been given a value from 1 to 10 and R for reticulocytes. For each fraction the mean FL4/SS values were transformed into IFCC HbA1c percentage values as shown in Table 1.
Figure 3B:
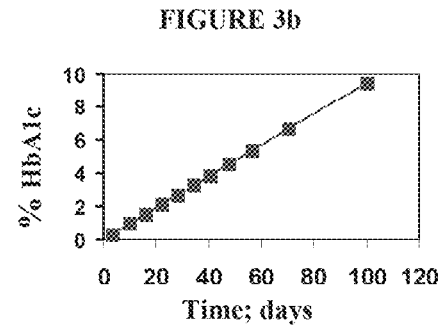
Figure 3C:
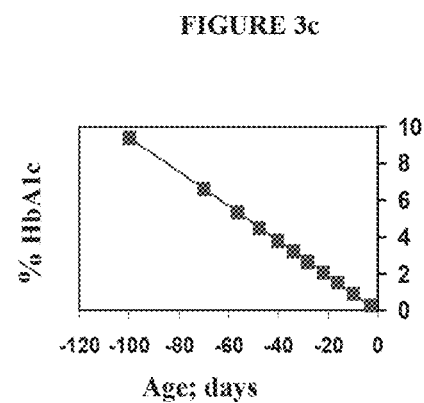

In the model that we are using, it is assumed that the HbA1c percentage of the red cells augments with time in the blood resulting in (percentage of represented cells in a fraction)=1/(time represented on the HbA1c percentage scale). In FIG. 3a, the uncorrected HbA1c percentage versus fraction number is shown. In FIGS. 3b and c, the HbA1c percentage was corrected and the fraction size was replaced by preliminary time and adapted to give a linear augmentation of the HbA1c percentage with the age of the cells. The fractions with a high HbA1c percentage having a low representation of cells are now assigned a greater amount of time. This is reasonable, because compared to the ideal model, the high HbA1c fractions in a real situation represent cells of which a part has not yet appeared or has disappeared.

To explain the difference in the older fractions between the reference sample from six normal subjects and the hypothetical model, it is assumed that the correction of the time axis in the older fractions is correcting mainly for the clearance of red cells by the reticuloendothelial system. The model also permits calculation of an age assigned to the immature cells. In this reference sample, the time was approximately 30 percent of the time assigned to the first fraction of the mature cells, the fraction in age directly following after the reticulocytes. Taking into account that there are 10 fractions, this implicates that the number of immature cells is approximately 3% of the total number of red blood cells. The percentage of reticulocytes of the total number of cells that we recovered in the assay was only 0.5%. Apparently, approximately 80% of the cells at the maturation stage between the formation of hemoglobin and the disappearance of RNA are not in the blood stream.

For the time calculation, the data of the fraction limit values of FL4/SS and the number of cells in each fraction were used in the example. The fraction limit values of the reticulocyte fractions were not used. In fact, the majority of immature red cells are absent from the blood circulation. As a consequence, the reticulocytes present in the circulation were considered as the most mature part of the immature red cells and therefore the mean FL4/SS value of the reticulocytes was also taken as the fraction limit of the immature cells.

FIG. 3A is a graphical representation of IFCC HbA1c percentage per fraction. FL4/SS fractions from normal human subjects were obtained as described in example 2 and analysed as shown in FIG. 1. The fractions are as shown in Table 1 and have been given a value from 1 to 10 and R for reticulocytes. For each fraction the mean FL4/SS values were transformed into IFCC HbA1c percentage values as shown in Table 1. The values from column (a) and (c) were used for FIG. 3A.

FIG. 3 (B) is a graphical representation of IFCC HbA1c percentage on a time axis.

FIG. 3 (C) is a graphical representation of IFCC HbA1c percentage on an age axis. The age is expressed in days in negative values. The values from columns (d) and (i) of Table 1 were used for FIGS. 3B and 3C.

FIG. 3 (D) is a graphical representation of the derived IFCC percentage HbA1c values versus age. The derivative of FIG. 3C yields a constant value (see Table 1). This value has been normalized to the measured mean IFCC HbA1c percentage of the reference samples. The values of column (i) and a constant value (d)/(i) normalized for the mean IFCC HbA1c percentage value of the samples (3.44) were used for FIG. 3D as the differential of FIG. 1C.

FIG. 3 (E) is a graphical representation of fraction size per fraction. The fraction sizes expressed in IFCC HbA1c percentage units were calculated as shown in Table 1.

FIG. 3 (F) is a graphical representation of the percentage of cells represented in the blood circulation on an age axis. The calculation of the percentages is presented in Table 1. The values of columns (a) and (e) were used for FIG. 3E and the values from column (h) and (i) were used for FIG. 3F.

The values represented in FIGS. 3A-3F are summarized in Table 1.

TABLE 1

Figure 3D:
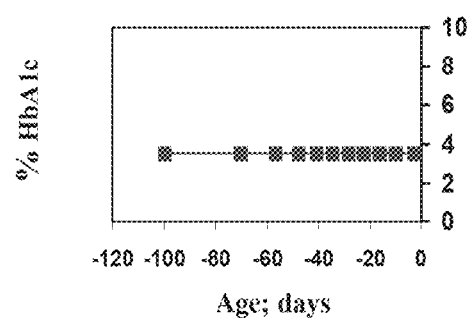
Figure 3E:
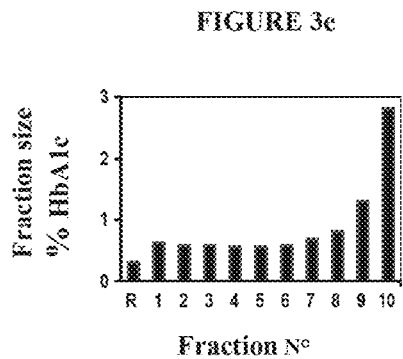
Figure 3F:
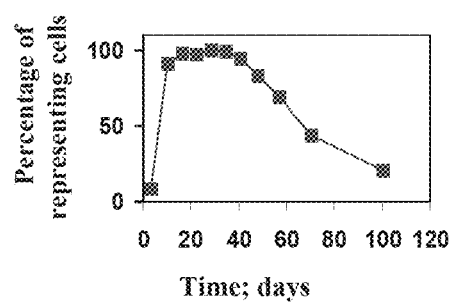

Calculation of the IFCC HbA1c percentage per fraction (FIG. 3A), of the IFCC HbA1c percentage per time in days (FIG. 3B), or per age in days (FIG. 3C); and the derivative of the IFCC HbA1c percentage per time in days (FIG. 3D). The fraction size per fraction (FIG. 3E) and a calculation of representing cells as a function of time in days (FIG. 3F).

| a | b | c | d | e | f | g | h | i |
|---|---|---|---|---|---|---|---|---|
| Reticulocytes (R) | 12.10 | 0.41 | 0.30 | 0.30 | 3.30 | 187 | 8.75 | 3.30 |
| Fraction 1 | 34.69 | 1.18 | 0.92 | 0.62 | 1.61 | 3964 | 90.74 | 10.05 |
| Fraction 2 | 53.43 | 1.82 | 1.50 | 0.58 | 1.74 | 3945 | 97.50 | 16.31 |
| Fraction 3 | 70.30 | 2.39 | 2.07 | 0.57 | 1.76 | 3906 | 97.50 | 22.51 |
| Fraction 4 | 85.51 | 2.91 | 2.63 | 0.56 | 1.79 | 3934 | 100 | 28.59 |
| Fraction 5 | 99.39 | 3.38 | 3.18 | 0.55 | 1.81 | 3854 | 99.36 | 34.59 |
| Fraction 6 | 112.97 | 3.84 | 3.76 | 0.58 | 1.72 | 3869 | 94.73 | 40.91 |
| Fraction 7 | 127.38 | 4.33 | 4.42 | 0.66 | 1.51 | 3917 | 83.84 | 48.14 |
| Fraction 8 | 143.33 | 4.88 | 5.22 | 0.80 | 1.25 | 3908 | 69.72 | 56.81 |
| Fraction 9 | 165.97 | 5.65 | 6.48 | 1.26 | 0.78 | 3898 | 44.15 | 70.47 |
| Fraction 10 | 207.21 | 7.05 | 9.19 | 2.71 | 0.37 | 4011 | 21.01 | 100.00 | a. Reticulocytes and fraction by number as presented in FIG. 1B.
b. HbA1c fluorescence values divided by side scatter values of the fraction limits as presented in FIG. 1B. The mean value of the reticulocytes present in the blood stream was taken as the fraction limit value. The fraction limit of the last fraction 10 was estimated to be the mean fluorescence value of the last fraction 10 plus half of the difference between the fraction limit values of fractions 8 and 9. The values were corrected for background and compensation of fluorescence.
c. Fraction limit values expressed in preliminary IFCC percentage HbA1c. Each fraction limit value in column b was divided by the mean value of column b. The resulting value was multiplied with the mean IFCC HbA1c percentage value of 3.44 of the samples.
d. Fraction limit values expressed in IFCC percentage HbA1c. The values of column d (d) were obtained from the values of column c, using Formula (VIII); (d) = 4.54*($e^{0.157*(c)}$ − 1)
e. Fraction size in HbA1c percentage = fraction (n) − fraction (n − 1) from column d.
f. The inverse value; 1/fraction (n) of the values of column e according to formula (II).
g. Number of cellular events of each fraction.
h. Values of column f multiplied with values of column g. The maximum value of column h was taken 100 percent. The other values were calculated accordingly.
i. The value of fraction 10 from column e was taken as 100 days. The other values of column j were calculated accordingly.

Using the formula VIII above, and maintaining the assumptions of constant glucose concentration and linear kinetics of HbA1c formation, the percentage of representing cells in a fraction can be calculated. The fractions in the beginning of the age axis, where cells are young, are large, presumably because cells are hiding in bone marrow or spleen before being released in the blood stream. At the end of the axis, the fractions are large presumably because the old cells are subjected to elimination. In (FIG. 3F), the percentages of represented cells are plotted on the age axis. The value of the smallest fraction was taken to be 100%. The pattern responds to the general expectation that at least during a considerable time the red cells are fully represented in the blood stream and not yet subjected to elimination.

In embodiments, the approach was taken to analyze the representation of cells in the blood samples. Using these conditions the fluctuation of cell numbers appeared to be as one that is generally accepted as normal in a normal individual, providing a strong indication that the chosen conditions are correct (FIG. 3F).

In the calculation of the time axis as described above, a constant glucose concentration undergone by the blood was a condition. In the case of a diabetic blood sample, variations of glucose concentration have to be taken into account. The division of the cellular events into ten fractions as described is not dependent on glucose concentration or cellular hemoglobin, so corresponding fractions from normal and diabetic samples can be compared.

The values of the fraction limits can change when changes in glucose concentration or changes in percentage of representing cells occur. Changes in glucose concentration can have a different effect on the HbA1c percentage versus time plot than changes in percentage of representing cells. The time axis is derived from the HbA1c percentage axis as described in, for example, Example 3.

Correction of the Time Axis with Respect to the HbA1c Reaction/Time Curve.

Using formula derived from the standard curve and the modification of the time/percentage axis according to example 3 provided a reasonable fit with glucose values, but gave improbable Figures for the recovery of cells of the different ages from the blood stream. Especially the younger age groups seemed underrepresented. Apparently, the reaction of glucose and hemoglobin follows a time curve that is not entirely straight, but has the appearance of a saturation curve. The first steps of the Amadori reaction are not irreversible and this might cause a saturation effect. Also, the glycated hemoglobin is subject to further reaction into advanced glycated end (AGE) products (c.f. Makita, Z. et al Science 1992, vol. 258, pp 651-653).

Application of a formula (XII): $y=x^{1.3}$ applied to the time axis gave a good fit with the percentages of recovery of cells of different ages from the blood stream (example 3, FIG. 3H). The resulting curve provides "real HbA1c values" as a function of time (FIG. 3E). The derivative of this curve than provides the real HbA1c percentage formation rate as a function of the time fractions (FIG. 3F). "The HbA1c rate" herein is defined as the mean HbA1c value of a sample, if the rate of the formation of HbA1c percentage in a given age fraction would have been the rate of formation throughout the life of the red cells.

Since the real HbA1c formation rate decreases with time, it is not feasible for comparison with glucose values. For this purpose, the derived HbA1c percentage values giving constant values over time as shown in FIG. 3D, were combined with the newly constructed time axis. Assuming that the application of the standard curve and the exclusion of the saturation effects provide an HbA1c formation rate that is only dependent on the glucose concentration, the modified HbA1c formation rate will be referred to as "glucose dependent HbA1c percentage rate".

The reference values from which the time axis were calculated were used as a template ("time template") to calculate the age of cells in the fractions from different samples. The HbA1c percentage limit values of the fractions were used as arbitrary age or time units and a reaction curve was constructed (Example 3, FIGS. 3A, B and C). The derivative of the reaction curve would be a horizontal line representing the constant rate of HbA1c formation as expected at a constant glucose concentration and under the assumptions described above (FIG. 3D). As can be observed from FIG. 3E, the sizes of the fractions on the time scale are irregular and differ substantially between each other. This is likely due to the fact that red cells of certain ages are absent from the circulation for different reasons.

Example 4

Figure 5A:
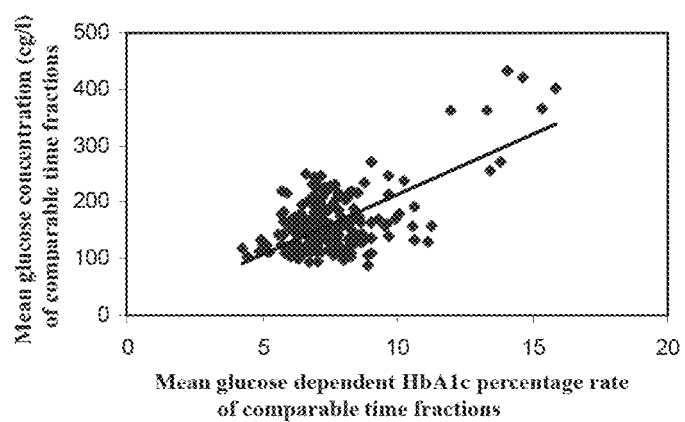
FIG. 5 (A) is a scatterplot representation of the relationship of the mean HbA1c percentage values and the mean glucose concentration over a period of 30 days preceding the sample collection. The data have been obtained as described in example 4.

This example describes analysis of hemoglobin in 26 diabetic patients.
Methods and Results A study including 26 diabetic patients was conducted with local ethical committee approval. The patients were chosen from those attending the diabetic clinic, irrespective of the type of diabetes or other pathological conditions. Patients who had measured and administrated their own capillary glucose values several times a day were selected and copies were made of their note books covering a certain period of glucose measurement. Blood was drawn on EDTA and analyzed as described in example 1. HbA1c was measured using the cytometric procedure. The mean glucose value of each patient was calculated over the period of 30 days before the drawing of the blood sample and the mean values were compared with the HbA1c values of the cytometric procedure showing a correlation having a $R^2$ value of 0.45 (FIG. 5A). This low correlation was expected and has been reported in the literature (McCarter et al. Diabetes Care. 2004; 27: 1259-1264, Hudson et al. Ann. Clin. Biochem. 1999; vol. 36, 451-459).

Tables 2A-2E show the calculation of the HbA1c percentage derivative or glucose concentration in the age fractions of Patient 8 with respect to a Reference.

TABLE 2A

| a<br>Reticulocytes (R) | b | c | d | e | f |
|---|---|---|---|---|---|
| Reference; Calculation of the position of the fractions with respect to the reference fractions. | | | | | |
| Fraction 1 | 39.00 | 1 | 0 | 1 | 0 |
| Fraction 2 | 57.67 | 1 | 0 | 1 | 0 |
| Fraction 3 | 74.50 | 1 | 0 | 1 | 0 |
| Fraction 4 | 89.67 | 1 | 0 | 1 | 0 |
| Fraction 5 | 103.50 | 1 | 0 | 1 | 0 |
| Fraction 6 | 117.00 | 1 | 0 | 1 | 0 |
| Fraction 7 | 131.33 | 1 | 0 | 1 | 0 |
| Fraction 8 | 147.17 | 1 | 0 | 1 | 0 |
| Fraction 9 | 169.67 | 1 | 0 | 1 | 0 |
| Fraction 10 | 210.70 | 1 | 0 | 1 | 0 |
| Patient 8; Calculation of the position of the fractions with respect to the reference fractions. | | | | | |
| Fraction 1 | 49.00 | 1.26 | 0 | 0.74 | 0.26 |
| Fraction 2 | 72.00 | 1.25 | 0 | 0.75 | 0.25 |
| Fraction 3 | 95.00 | 1.28 | 0 | 0.72 | 0.28 |
| Fraction 4 | 117.00 | 1.30 | 0 | 0.70 | 0.30 |
| Fraction 5 | 136.00 | 1.31 | 0 | 0.69 | 0.31 |
| Fraction 6 | 154.00 | 1.32 | 0 | 0.68 | 0.30 |
| Fraction 7 | 171.00 | 1.30 | 0 | 0.70 | 0.30 |
| Fraction 8 | 191.00 | 1.30 | 0 | 0.70 | 0.30 |
| Fraction 9 | 217.00 | 1.28 | 0 | 0.72 | 0.28 |
| Fraction 10 | 261.89 | 1.24 | 0 | 0.76 | 0.24 | a. Fraction by number as presented in FIG. 1B.
b. Fraction limit values on a FL4/SS scale as presented in FIG. 1B; The Fraction limit of the last fraction 10 was estimated to be the mean fluorescence value of the last fraction 10 plus 0.5x the difference between the fraction limit values of fractions 8 and 9. The values were not corrected for background and compensation of fluorescence.
c. Values of (b) of the sample divided by values of (b) of the reference, showing the position of a fraction limit with respect to the reference.
d, e and f. Parts of the sample fraction that are assigned to the previous (d), corresponding (e) and the following fraction (f) of the reference respectively.

TABLE 2B

Reference; Calculation of the position of the Mean HbA1c value within the fractions.

| a | g | h | i | j | k | l | m | n |
|---|---|---|---|---|---|---|---|---|
| Reticulocytes (R) | | 14.44 | 14.44 | | 40.66 | 0.69 | 1.80 | 0.38 |
| Fraction 1 | 23.06 | 23.06 | 33.40 | 34.69 | 34.69 | 1.59 | 1.54 | 1.03 |
| Fraction 2 | 43.74 | 20.68 | 19.25 | 53.43 | 18.74 | 0.91 | 0.83 | 1.10 |
| Fraction 3 | 61.56 | 17.82 | 16.92 | 70.30 | 16.87 | 0.80 | 0.75 | 1.07 |
| Fraction 4 | 77.59 | 16.03 | 15.25 | 85.51 | 15.21 | 0.72 | 0.67 | 1.07 |
| Fraction 5 | 92.07 | 14.48 | 14.06 | 99.39 | 13.88 | 0.67 | 0.62 | 1.08 |
| Fraction 6 | 105.71 | 13.64 | 13.79 | 112.97 | 13.58 | 0.65 | 0.60 | 1.09 |
| Fraction 7 | 119.64 | 13.94 | 14.46 | 127.38 | 14.41 | 0.69 | 0.64 | 1.07 |
| Fraction 8 | 134.63 | 14.98 | 16.82 | 143.33 | 15.94 | 0.80 | 0.71 | 1.13 |
| Fraction 9 | 153.29 | 18.66 | 30.67 | 165.97 | 22.65 | 1.46 | 1.01 | 1.45 |
| Fraction 10 | 195.96 | 42.68 | 42.68 | 207.21 | 41.24 | 2.03 | 1.83 | 1.11 |

TABLE 2B

Patient 8; Calculation of the position of the Mean HbA1c value within the fractions.

| a | g | h | i | j | k | l | m | n |
|---|---|---|---|---|---|---|---|---|
| Reticulocytes (R) |  | 15.26 | 15.26 | 15.26 | 50.16 | 0.59 | 1.79 | 0.33 |
| Fraction 1 | 30.37 | 30.37 | 43.13 | 44.79 | 44.79 | 1.67 | 1.60 | 1.05 |
| Fraction 2 | 55.90 | 25.54 | 24.31 | 67.71 | 22.93 | 0.94 | 0.82 | 1.15 |
| Fraction 3 | 78.99 | 23.09 | 22.78 | 90.76 | 23.05 | 0.88 | 0.82 | 1.07 |
| Fraction 4 | 101.47 | 22.48 | 21.57 | 112.79 | 22.03 | 0.84 | 0.79 | 1.06 |
| Fraction 5 | 122.124 | 20.65 | 19.48 | 131.84 | 19.05 | 0.75 | 0.68 | 1.11 |
| Fraction 6 | 140.44 | 18.32 | 17.96 | 149.94 | 18.10 | 0.70 | 0.65 | 1.08 |
| Fraction 7 | 158.04 | 17.59 | 17.91 | 167.05 | 17.10 | 0.69 | 0.61 | 1.14 |
| Fraction 8 | 176.27 | 18.23 | 20.56 | 187.20 | 20.15 | 0.80 | 0.72 | 1.11 |
| Fraction 9 | 199.15 | 22.88 | 34.61 | 213.36 | 26.16 | 1.34 | 0.93 | 1.44 |
| Fraction 10 | 245.48 | 46.33 | 46.33 | 258.48 | 45.12 | 1.80 | 1.61 | 1.12 | g. Fraction mean values on a FL4/SS scale as presented in FIG. 1B. The values were corrected for background and compensation of fluorescence.
h. Difference between the fraction mean values; $h_n = g_n - g_{n-1}$. The reticulocyte value was added separately.
i. Synchronization of the fraction mean values differences (h) with the fraction limits (see FIG. 1B); $i_n = (h_n + h_{n+1})/2$. In fraction 1, $h_1$, being half as long, was multiplied with 2. The reticulocyte fraction was not synchronized.
j. Fraction limit values of (b), but corrected for background and compensation of fluorescence. As the fraction limit value of the reticulocytes, the mean value is taken.
k. Difference between the fraction limit values (fraction size); $k_n = j_n - j_{n-1}$. The fraction size of the reticulocytes was determined separately.
l. Synchronized fraction mean value differences (i), divided by the mean of the (i) values, resulting in values with a mean of 1.
m. Fraction limit values (k), divided by the mean of the (k) values, resulting in values with a mean of 1.
n. Position of the mean value within a fraction; 1/m.

TABLE 2C

Reference; Calculation of the derived NGSP HbA1c percentage per fraction and comparison with the glucose concentration values.

| a | o | p | q | r | s | t |
|---|---|---|---|---|---|---|
| Reticulocytes (R) | 1 | 0 | 0 | 1 | 5.30 | 106 |
| Fraction 1 | 1 | 0 | 0 | 1 | 5.30 | 106 |
| Fraction 2 | 1 | 0 | 0 | 1 | 5.30 | 106 |
| Fraction 3 | 1 | 0 | 0 | 1 | 5.30 | 106 |
| Fraction 4 | 1 | 0 | 0 | 1 | 5.30 | 106 |
| Fraction 5 | 1 | 0 | 0 | 1 | 5.30 | 106 |
| Fraction 6 | 1 | 0 | 0 | 1 | 5.30 | 106 |
| Fraction 7 | 1 | 0 | 0 | 1 | 5.30 | 106 |
| Fraction 8 | 1 | 0 | 0 | 1 | 5.30 | 106 |
| Fraction 9 | 1 | 0 | 0 | 1 | 5.30 | 106 |
| Fraction 10 | 1 | 0 | 0 | 1 | 5.30 | 106 |

TABLE 2C

Patient 8; Calculation of the derived NGSP HbA1c percentage per fraction and comparison with the glucose concentration values.

| a | o | p | q | r | s | t |
|---|---|---|---|---|---|---|
| Reticulocytes (R) | 0.87 | −0.13 | −0.14 | 0.856 | 5.63 | 133.26 |
| Fraction 1 | 1.00 | −0.00 | −0.01 | 0.992 | 6.52 | 154.36 |
| Fraction 2 | 1.06 | 0.06 | 0.09 | 1.094 | 7.20 | 170.33 |
| Fraction 3 | 1.00 | 0.00 | 0.02 | 1.017 | 6.69 | 158.35 |
| Fraction 4 | 0.99 | −0.01 | −0.04 | 0.958 | 6.30 | 149.09 |
| Fraction 5 | 1.03 | 0.03 | 0.06 | 1.064 | 6.99 | 165.55 |
| Fraction 6 | 1.00 | −0.00 | −0.02 | 0.978 | 6.43 | 152.25 |
| Fraction 7 | 1.04 | 0.04 | 0.08 | 1.085 | 7.13 | 168.83 |
| Fraction 8 | 0.91 | −0.09 | −0.12 | 0.878 | 5.77 | 136.60 |
| Fraction 9 | 1.06 | 0.06 | 0.10 | 1.100 | 7.24 | 171.26 |
| Fraction 10 | 1.01 | 0.01 | 0.04 | 0.037 | 6.82 | 161.41 | o. Calculation of the position of the reference mean values with respect to sample fractions; (d), (e) and (f) are multiplied with (n) of the reference and the sum is taken.
p. (o) − 1.
q. Transformation of the position of the mean value within a fraction with respect to the corrected position of the reference; The square root of the absolute value of (q) was multiplied with 1 or −1 depending on the sign of (q). The result was multiplied with a constant; 0.4.
r. (r) + 1
s. Derived NGPS HbA1c percentage value per fraction, obtained by multiplying (s) with the NGPS HbA1c percentage value of the sample.
t. The mean of the glucose concentration of the fractions as determined by self-monitoring and expressed in mg/100 ml was divided by the mean of the derived HbA1c percentage value of the fractions (t). The resulting factor was multiplied with each fraction value of (t), to obtain relative derived HbA1c percentage values comparable with glucose concentration values.

TABLE 2D

Reference; Calculation of the age of the fractions.

| a | u | v | w | x | y | z | aa | ab | ac | ad |
|---|---|---|---|---|---|---|----|----|----|----|
| Reticulocytes (R) | 0.14 | 0.49 | 0.08 | 0.08 | 0.08 | 187 |  | 0.08 | 2.83 | 2.83 |
| Fraction 1 | 0.34 | 1.18 | 0.20 | 0.12 | 0.12 | 3964 | 1.01 | 0.12 | 4.40 | 7.22 |
| Fraction 2 | 0.53 | 1.81 | 0.33 | 0.13 | 0.13 | 3945 | 1.01 | 0.13 | 4.49 | 11.72 |
| Fraction 3 | 0.70 | 2.39 | 0.45 | 0.13 | 0.13 | 3906 | 1.00 | 0.12 | 4.40 | 16.12 |
| Fraction 4 | 0.84 | 2.90 | 0.58 | 0.12 | 0.12 | 3934 | 1.00 | 0.12 | 4.35 | 20.47 |
| Fraction 5 | 0.98 | 3.37 | 0.70 | 0.12 | 0.12 | 3854 | 0.98 | 0.12 | 4.20 | 24.68 |
| Fraction 6 | 1.11 | 3.84 | 0.83 | 0.13 | 0.13 | 3869 | 0.99 | 0.13 | 4.45 | 29.12 |
| Fraction 7 | 1.26 | 4.32 | 0.97 | 0.15 | 0.15 | 3917 | 1.00 | 0.15 | 5.15 | 34.27 |
| Fraction 8 | 1.41 | 4.87 | 1.15 | 0.17 | 0.17 | 3908 | 1.00 | 0.17 | 6.16 | 40.43 |

TABLE 2D-continued

Reference; Calculation of the age of the fractions.

| a | u | v | w | x | y | z | aa | ab | ac | ad |
|---|---|---|---|---|---|---|----|----|----|-----|
| Fraction 9  | 1.64 | 5.63 | 1.42 | 0.28 | 0.28 | 3898 | 0.99 | 0.27 | 9.67  | 50.10 |
| Fraction 10 | 2.04 | 7.03 | 2.02 | 0.60 | 0.60 | 4011 | 1.02 | 0.61 | 21.52 | 71.62 |

TABLE 2D

Patient 8; Calculation of the age of the fractions.

| a | u | v | w | x | y | z | aa | ab | ac | ad |
|---|---|---|---|---|---|---|----|----|----|-----|
| Reticulocytes (R) | 0.12 | 0.40 | 0.07 | 0.07 | 0.08 | 233  |      | 0.08 | 3.51  | 3.51  |
| Fraction 1  | 0.34 | 1.18 | 0.20 | 0.14 | 0.14 | 3575 | 1.00 | 0.14 | 6.41  | 9.92  |
| Fraction 2  | 0.52 | 1.78 | 0.32 | 0.12 | 0.11 | 3625 | 1.01 | 0.11 | 5.10  | 15.01 |
| Fraction 3  | 0.69 | 2.39 | 0.45 | 0.13 | 0.13 | 3501 | 0.98 | 0.13 | 5.85  | 20.87 |
| Fraction 4  | 0.86 | 2.97 | 0.59 | 0.14 | 0.14 | 3666 | 1.02 | 0.15 | 6.82  | 27.69 |
| Fraction 5  | 1.01 | 3.47 | 0.72 | 0.13 | 0.12 | 3557 | 0.99 | 0.12 | 5.61  | 33.31 |
| Fraction 6  | 1.15 | 3.94 | 0.86 | 0.13 | 0.14 | 3592 | 1.00 | 0.14 | 6.32  | 39.63 |
| Fraction 7  | 1.28 | 4.39 | 0.99 | 0.14 | 0.13 | 3501 | 0.98 | 0.12 | 6.65  | 45.28 |
| Fraction 8  | 1.43 | 4.92 | 1.17 | 0.17 | 0.20 | 3623 | 1.01 | 0.20 | 9.19  | 54.47 |
| Fraction 9  | 1.63 | 5.61 | 1.41 | 0.25 | 0.22 | 3543 | 0.99 | 0.22 | 10.24 | 64.71 |
| Fraction 10 | 1.98 | 6.80 | 1.91 | 0.49 | 0.48 | 3723 | 1.04 | 0.49 | 22.84 | 87.55 | u. Fraction limit values as in column (j) with the exception of the reticulocyte fraction. Of this fraction the mean value was taken. The value (j) of each fraction was divided by the mean of the fractions.
v. Values of (u) multiplied with the IFCC HbA1c percentage of the reference sample (3.44%)
w. Application of formula XI to the values of (v); $w = e^{0.157*(v)} - 1$
x. Differences between the values of w; $x = w_n - w_{n-1}$.
y. Values of (x) divided by the position of the mean of a fraction, relative to the position of the mean of a corresponding fraction of the reference as in column (s).
z. Total number of cellular events in each fraction.
aa. (z) divided by the number of cellular events of the ten fractions and multiplied with 10.
ab. (y)*(aa).
ac. (ab) multiplied with the life-span factor as determined by best fit or calculated as presented in Table E. In the table a life-span factor as determined by best fit was used.
ad. Cumulative values of (ac); $ac_n + ac_{n-1}$, representing the age of the fractions in days.

TABLE 2E

Reference; Calculation of the life-span factor.

| a | ae | af | ag | ah | ai | aj | ak | al | am |
|---|----|----|----|----|----|----|----|----|-----|
| Reticulocytes (R) | 6.43 | 5.38 |      | 6.12 | 10.55 | 40.92 | 1.00 | 1.00 | 64.64 |
| Total sample      | 1.05 |      | 0.88 |      |       | 40.80 |      |      |       |

TABLE 2E

Patient 8; Calculation of the life-span factor.

| a | ae | af | ag | ah | ai | aj | ak | al | am |
|---|----|----|----|----|----|----|----|----|-----|
| Reticulocytes (R) | 8.39 | 7.30 |      | 7.93 | 18.17 | 37.60 | 0.94 | 0.90 | 81.10 |
| Total sample      | 1.09 |      | 0.92 |      |       | 40.00 |      |      |       | ae. Acridine orange RNA staining; FL1 (488 nm) fluorescence values.
af. Reticulocytes (ae) minus Total cells (ae).
ag. Total cells (ae) minus FL1 background value (0.17).
ah. Reticulocytes (af) divided by Total cells (ag).
ai. (ah) to the power of 1.3.
aj. Cellular hemoglobin content; Side Scatter values.
ak. Reticulocytes (aj) divided by Total cells (aj).
al. (ak) to the power of 1.7.
am. (ai)*(al) multiplied with a constant value (6.10). (am) is representing the life-span factor.

Use of the Reference Values of the Time Axis to Calculate the Time Axis of the Different Samples.

The time axis of the reference sample was determined on the basis of the levels of the glucose HbA1c percentage rate, assumed to be constant and on the life span of approximately 120 days. The time axis of the patient samples as described in example 4, however cannot be calculated directly, since the glucose dependent HbA1c percentage rate will not be constant in these patients. To calculate the time axis from the patient samples, the differential of the HbA1c values of the reference (time template) was used as it was used for the calculation of the preliminary time axis of the reference.

Variables inherent to the patient samples were applied to modify the x-axis of the samples. The choice of these variables is important, since they do not only influence the time on the x-axis, but also indirectly the glucose dependent HbA1c percentage values of the patient samples, since the x values make part of the formula for glucose dependent HbA1c values; d(y)/d(x). Deriving the d(x) from the d(y) as has been done in the case of the reference sample would result in a flat line what has been the purpose in the case of the reference sample, but is not the purpose in case of the patient samples. The variables that affect the time on the x-axis are: 1) The number of cells in each fraction as being given by the computer, 2) The number of cells represented in the patient sample with respect to an ideal model, or the reverse of the length of the fractions on the original FL4/SS scale as presented in FIG. 1 B (formula 1), also being given by the computer.

Applying these corrections does not lead to the flat line as mentioned above. The position of the mean within a fraction has been left out expressly, since this position reflects exactly the differences of the HbA1c rate levels between the fractions. For a demonstration; see example 6. The operation can also be done in the reverse way, not correcting a sample time template for the reverse of the length of the fractions, but for the position of the mean within the fractions, which can be calculated using geometric means as shown in example 6. The application of the corrective factors 1 and 2 is demonstrated in example 5 and table 2. To ascertain that the newly constructed time axis were optimally comparable to the time axis of the reference sample, the total of the time fractions on the axis was brought back to the total of the reference time axis of 115 days.

As shown in example 7, the differential of the HbA1c percentage values of the patient samples d(y) was now divided by the newly calculated time values of the fractions d(x). Graphic presentations were made plotting the d(x)/d(y) or glucose dependent HbA1c percentage values against the integral (x) of the time values of the fractions d(x).

Example 5

This example describes analysis of blood samples from diabetic patients and the position of the mean HbA1c values within the fractions.
Methods and Results Non-diabetic and diabetic whole blood samples were prepared and analyzed as shown in Example 1 and FIG. 1. The FL4/SS fraction limit values as well as the FL4/SS mean value of each mature red cell fraction were collected. As a non-diabetic reference, the data of six normal subjects were used as described in Example 3. The derived HbA1c percentages of the fractions of the reference as a function of age were intended to be flat and were given the constant value of the mean NGSP HbA1c percentage.

The conversion of the FL4/SS axis into a time axis as demonstrated in Example 3 can only be applied to a blood sample of which the derived HbA1c percentage value is supposed to be constant. In diabetic patients, undergoing variation of blood glucose concentration over time, such an assumption cannot be made. In the case of a diabetic patient, the size of a fraction as measured on the FL4/SS axis is not only a function of the age segment represented by the fraction, but also of the possible variations in HbA1c percentage.

In a fraction, a variation of the HbA1c percentage, expressed as the derived HbA1c percentage, has a relationship with the position of the mean FL4/SS value within the fraction as calculated by the algorithm.

The position of the mean value within a fraction in a plot as shown in FIG. 1B, is defined by the product of the numbers of cells and their FL4/SS value. The position of the mean is where these products are below the mean position and above the mean position are equal. This means that the surface of a fraction as shown in FIG. 1B is divided in two equal parts. A change, higher or lower, in the derived HbA1c value undergone by the cells of a diabetic patient will lead to the reposition of the mean FL4/SS value within a fraction, higher or lower respectively. By dividing the value of the mean by the size of the fraction, each shift of the position of the mean value within a fraction is independent of the age of the cells and can therefore be used to calculate the derived HbA1c percentage value of a fraction of a diabetic patient.

The derived HbA1c percentage of the patient samples was directly calculated from the position of the mean values within the fractions of the sample in comparison with the position of the mean values within the fractions of the reference. For correct calculation, it has to be taken into account that the patient fractions are not of similar size as the reference fractions. Since the mean value of a fraction depends on the position of the fraction limits on the FL4/SS axis, in a first step, the overlap of sample fractions with respect to reference fractions was determined. The calculation of these overlaps of corresponding, preceding and following fractions is shown in Table 2A. Superimposed fractions were represented by a value of 1 (Column d, e and f). Taking in account the overlaps as shown in Table 2A, the relative position of the mean of the fractions of a sample was calculated. The quotient of the sample position and the reference position after correction for overlap was calculated as shown in Table 2B column n. The value of 1 represents identity of two positions (Table 2C, Column o).

To compare the relative position of the mean values in corresponding fractions between patients and reference, the deviation of the mean of the patient fraction was obtained by subtracting 1 (Table 2C column p). To obtain a linear relationship with the differential HbA1c percentage or the glucose concentration associated to a fraction, two further corrections had to be applied; first, as mentioned above, a mean value as depicted in FIG. 1B divides a fraction into two parts with equal surface. The position of the mean value therefore depends on the surface and on the integral of the function that determines the increase of the HbA1c percentage. The function of this increase is not known, but it is assumed that this function should be linear or close to linear. In this case the deviation of the mean is a function of the square of the derived HbA1c percentage or glucose concentration. Reversely, the deviation of the position of the mean value with respect to a reference relates to the square root of the differential HbA1c value or the glucose concentration (Table 2C, column q). The above described calculation provides a relationship between a deviation of the mean value and a change in the derived HbA1c percentage value, comparing between the reference sample, which supposedly has undergone a constant concentration of glucose and a diabetic patient sample. After careful comparison of the variations in glucose concentration as administrated by the patient and the calculated variation in the derived HbA1c percentage, a constant (Table 2C, column q) is multiplied with the end result of the calculation to ascertain a best fit with the glucose concentrations.

The factor thus obtained, shows the increase or decrease of the derivative of the HbA1c percentage relative to the reference. Multiplication with the HbA1c percentage of the sample results in the derived HbA1c percentage values of the fractions (Table 2C column r).

Figure 6:
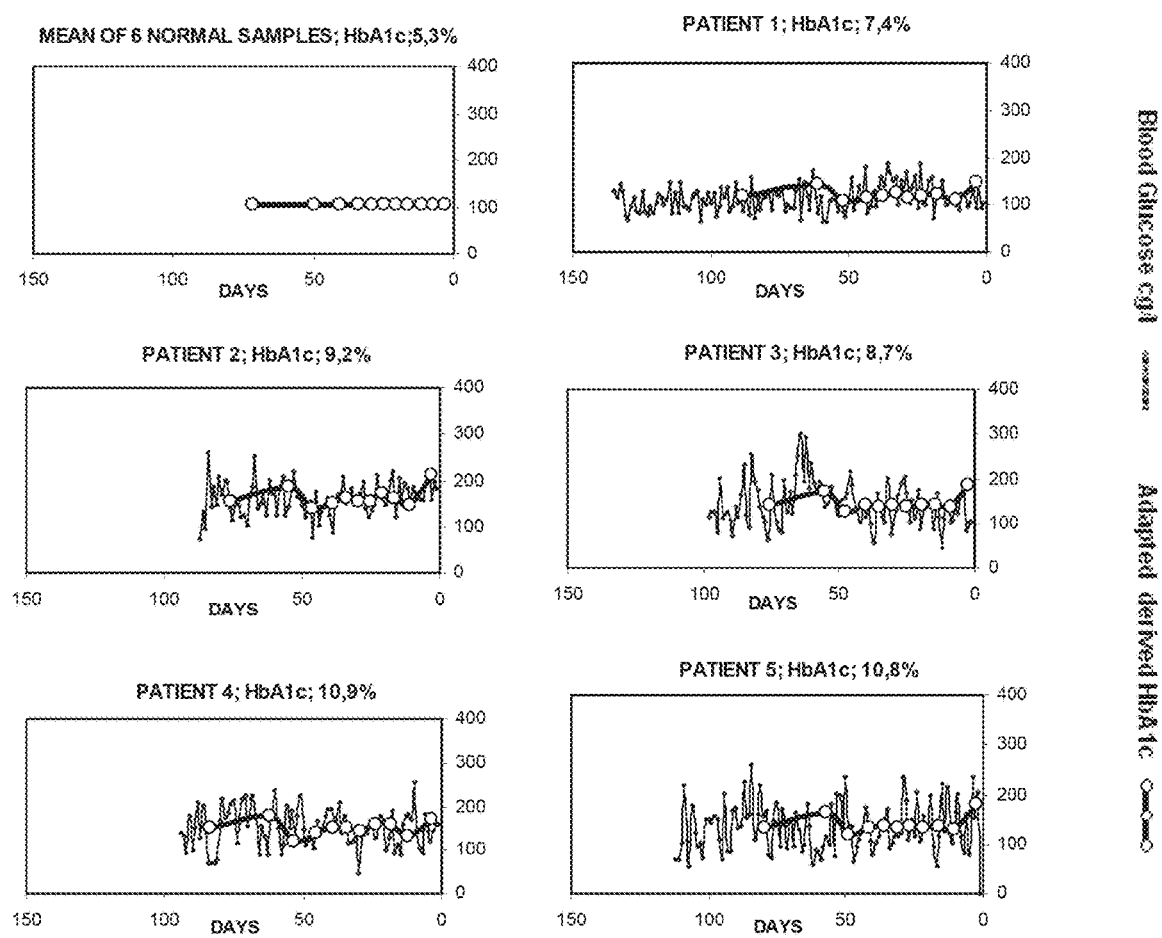
FIG. 6 shows graphical representations of 26 different time/age diagrams from 26 subjects having diabetes containing mean daily glucose concentration values obtained by self-monitering and the determined HbA1c percentage. The mean daily glucose concentration values on the ordinate were obtained as described in example 4. The time data on the abscissa were derived from the calendar of the self-monitering data. The derived HbA1c percentage values on the ordinate were calculated as shown in example 5 and table 2C (column t) and normalized as described in example 7. The age data on the abscissa were calculated as shown in example 6 and in table 2D column ad.
Figure 6:
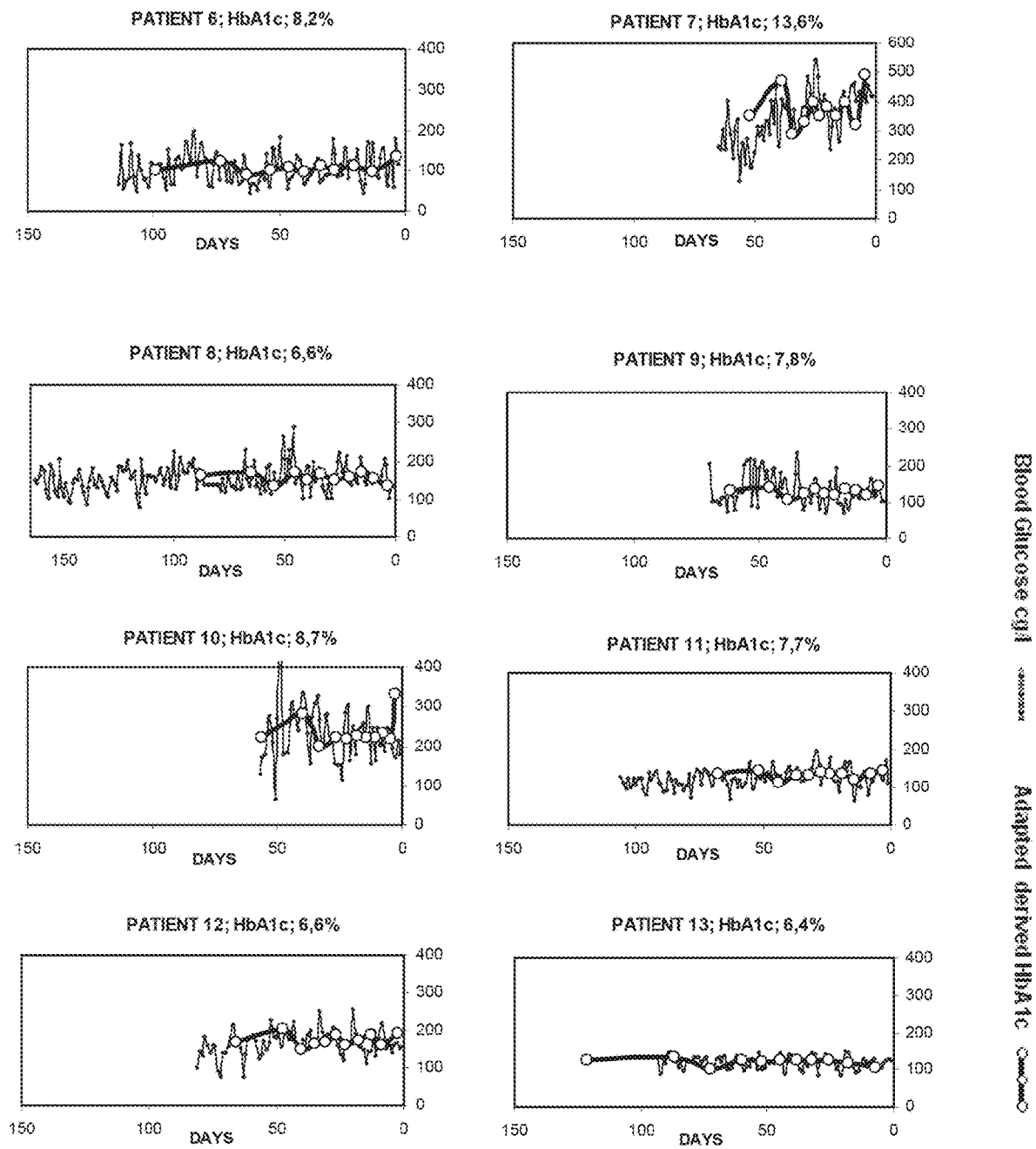
Figure 6:
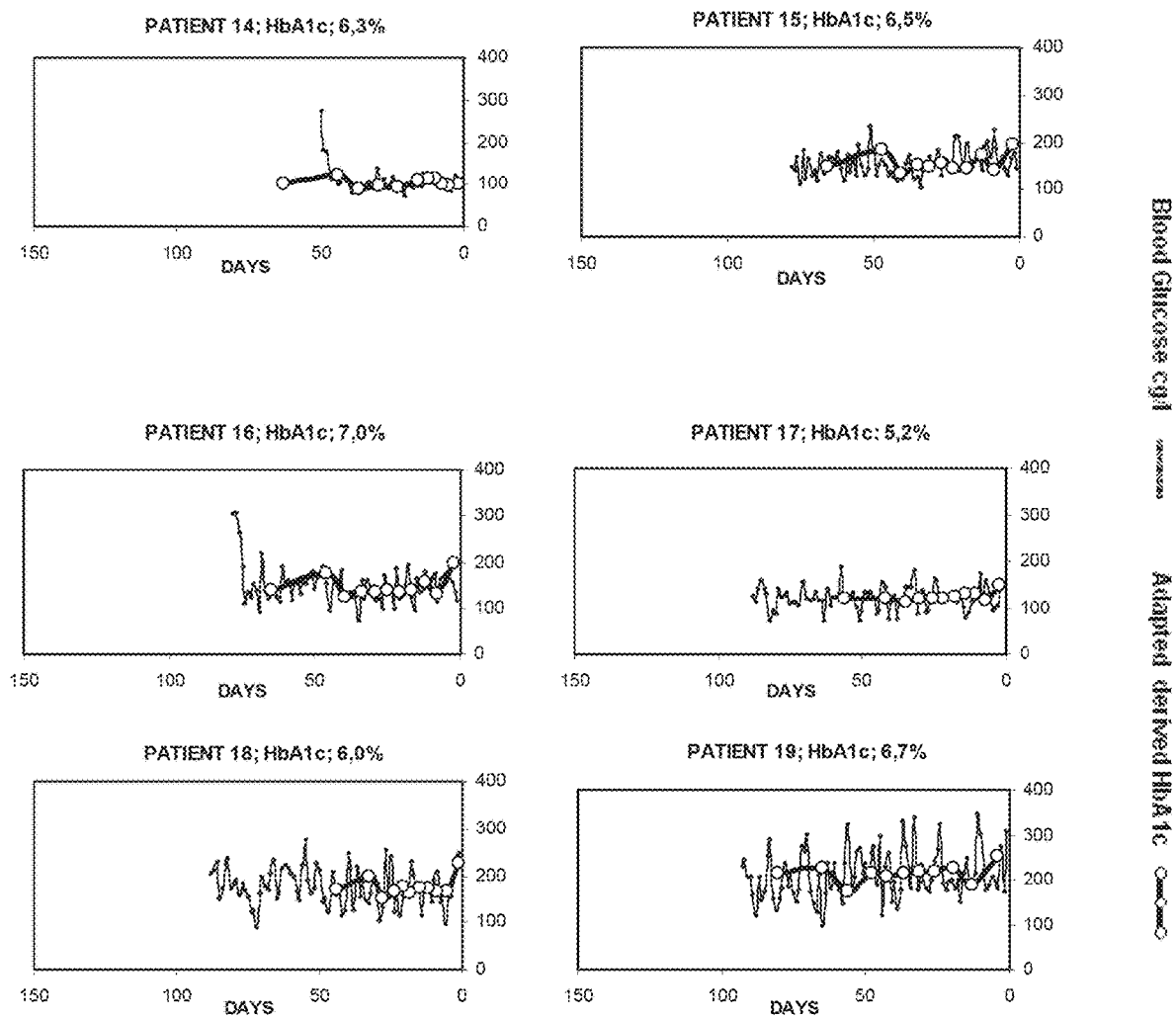
Figure 6:
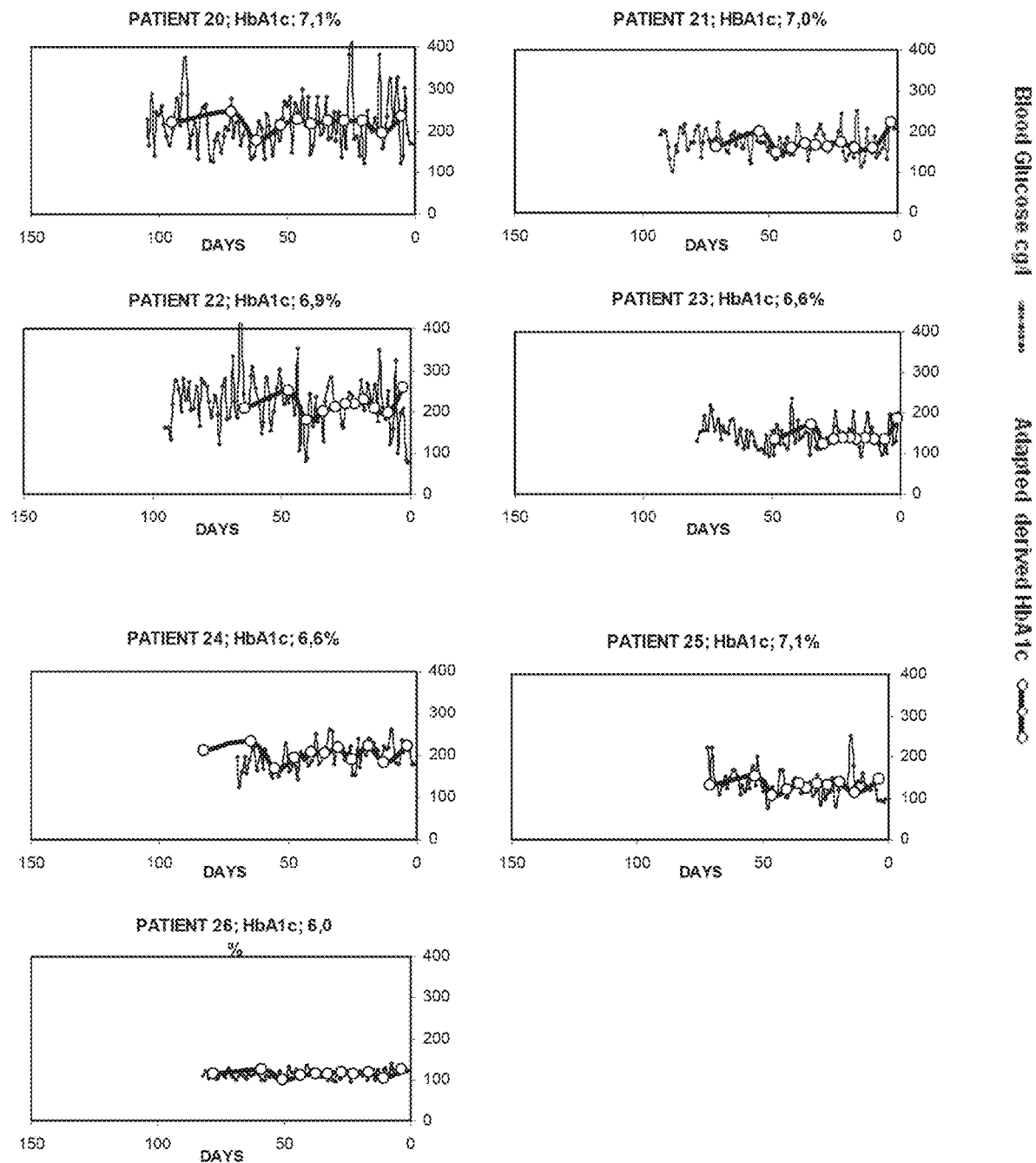

As shown in Table 2D and after correction for the exact number of cells in each fraction, the time segments were not multiplied with a factor giving a life-span of 120 days, as in Example 3, but were multiplied with a life-span factor as outlined in Example 7 and Table 2E, the calculated time provides the age of the fractions. A time curve of the derived HbA1c percentage of the fractions could now be constructed and compared with the monitored glucose concentration in the plasma of the patients (FIG. 6).

The following considerations were taken into account for the calculation of the derived HbA1c age curve. With respect to the fraction limits the following modifications were used. In the region of the last fraction No 10, the cellular events were very dispersed and also contaminating events were suspected. Therefore this fraction limit was estimated from its mean value and the differential of the before going fraction limits as shown in table 2B.

The reticulocyte fraction, distinct from the mature red cells by RNA staining, was analyzed separately. Only a small part of the most mature reticulocytes circulate in the blood. Therefore the mean value of the reticulocyte fraction will practically fall together with the fraction limit. For the calculation of the time axis, the mean value was used as the fraction limit. For the calculation of the derived HbA1c percentage however, this would not allow the measurement of the variation of the mean within the fraction. Choosing the fraction limit at the value of those reticulocytes being the highest in HbA1c gave relatively high values, since the highest HbA1c reticulocytes are stretching out far. The choice of this fraction limit however appeared useful for the measurement of variation of the relative position of HbA1c mean value (Table 2b, column k).

The relative position of the mean value within a fraction was the mean value divided by the fraction size. Since the fraction limit value is half a fraction ahead compared to the mean value of the fraction, the mean values of the fractions were shifted half a fraction ahead in order to synchronize on the time scale fraction limit values and fraction mean values (Table 2B, column i).

Example 6

This example shows a construction of a preliminary time scale applied to diabetic patient samples.
Methods and Results The FL4/SS fraction limit values were obtained and calculated as described in Example 1, and Examples 3 and 5. Instead of the reticulocyte fraction limit value, the reticulocytes mean values were used. As outlined in Examples 3 and 5, the reticulocytes fraction limit values were artificially high and should be at or near the fraction value. The fraction limit values were corrected for FL1 compensation and background.

A preliminary time scale for the reference compilation of 6 normal subjects is shown in FIGS. 3 c and d and is calculated as shown in table 1. This preliminary time scale was used as a template to determine the time scales of the diabetic patients of which fraction were derived and calculated similarly as the fractions of the reference sample. The computer data used to construct FIG. 1b were compared between the reference sample and the diabetic patient samples. Compared were; A, the exact number of cells in each fraction of the patient sample with the exact number of cells in the respective fractions of the reference sample. Patient values were divided by reference values and the template time values were divided by the resulting factor according to the principal that the percentage of cells is inversely correlated to time (see table 2 A for the calculation). The fraction lengths on the FL4/SS axis of the respective fractions were compared between the patient sample and the reference sample. To this end the distance between adjacent cut-off values as shown in FIG. 1b was measured by subtraction (see table 2 B). For the respective fractions, the patient values were divided by the reference values and the template time values were multiplied with the resulting factor (see table 2 C for the calculation).

The corrective factors as described above could not be applied to the reticulocytes fraction, being analyzed separately. In experiments comparing the glucose concentration and the FL4/SS values of the reticulocytes, it was however observed that is a correlation between the time attributed to the reticulocytes and the time of the first fraction of the mature cells. The ratio of the time of the reticulocytes of the reference sample and the time of the first fraction of the reference sample was applied to the patient samples. A second correction was made depending on the hemoglobin content of the reticulocytes. Low levels of hemoglobin correlated with a slow maturation of the reticulocytes and therefore extra time had to be added by division of the following factor; (reticulocytes cellular hemoglobin of the reference sample/reticulocytes cellular hemoglobin of the patient sample)$^{0.3}$ (see table 2 D for the calculation).

To calculate the age of the fractions, a time calculation was applied similar to the calculation presented in Example 3. How a variation of the HbA1c percentage derivative would affect the calculation of time is presented in FIG. 4. The above calculation provides the factor of variation of the HbA1c derivative (Table 2C, column r) and the time segments were divided by this factor. The corrected FL4/SS values of the patient samples were normalized using the mean HbA1c of the reference and subjected to Formula (I) as shown in (Table 2D column w).

As outlined in FIG. 4 the values obtained were corrected for the variations of the differential of HbA1c percentage values. FIG. 4 provides graphical representations of simulation of the effect of a temporary rise in blood glucose concentration of an otherwise normal subject; (A); HbA1c curve of a normal subject as presented in FIG. 3B and determined as in example 3 and Table 1; (B); as in (A), but with a temporary rise in blood glucose concentration; (C); as in (B), but determined as described in example 5 and Table 3. Since the time axis is derived from the HbA1c percentage values, in a plot as shown below 4(a), a temporary increase of % HbA1c would affect the % HbA1c axis as well as the time axis 4(b). An independent parameter for % HbA1c is needed, so time can be corrected and % HbA1c can be determined separately to give the correct representation 4(c).

The time scale obtained was given a length of 100 days producing a life-span of approximately 120 days as shown in Example 3, FIG. 3F.

Example 7

The example illustrates the alignment of glucose values and glucose dependent HbA1c percentage rate.
Methods and Results After the construction of the time axis of the patient samples and the calculation of the glucose dependent HbA1c percentage rate values, statistical data to test the validity of the procedure was obtained. The time points of the cytometric procedure of a patient sample were projected on the calendar of the self-monitoring glucose readings of the respective patient.

In FIG. 5 the behaviour of the mean value of a fraction on the FL4/SS axis and on the "count" axis is shown. In FIG. 5 A, the surface of the area A is equal to the surface area B, since the "count" values are cumulative. If the middle of the FL4/SS axis of the fraction is given a value of 1, the placement of the mean value (m) is given by $$\frac{2}{(a-b)*(0.5+a2+0.5*b2)^{0.5}};$$

in which a and b are the respective cut-off values as shown in the Figure. In FIG. 5 B the FL4/SS values are not cumulative. The mean value (m) on the "count" axis will only displace if the curve is raising or lowering exponentially as shown in the Figure. If the middle of the "count" axis of the fraction is given a value of 1, the placement of the mean value (m) is given by; 1+(arc tangents (second derivative of the mean FL4/SS values of the fractions))/3.14.

This example shows that the position of the mean value within a fraction in every case moves up and down concordantly with the glucose dependent HbA1c percentage rate. The computer calculates the mean values numerically and will place the mean values in the fraction in a similar way as calculated above with the geometric means. Correcting the basic template for the length of the FL4/SS fraction of the patient samples will leave the position of the mean value within the fraction intact, and will generate values that correlate with the glucose dependent HbA1c rate. Since the differences between the reference and the patient samples are relatively small, the calculation has been simplified by assuming a linear relationship between the respective positions of the mean values within a certain fraction of the reference and a patient sample.

In FIG. 3d, a graphic representation is shown of the glucose dependent HbA1c percentage rate on a preliminary time scale. The calculation of the values is shown in table 2A and B and is presented in table 2 B column k and l. The preliminary time scale (table 1; column k) was calculated from table 1; column j. Table 1; column j and k are presented in table 2 as "time template" and preliminary time scale. For each sample as described in Example 5 a preliminary time scale was constructed after correction for the exact number of cells in each fraction and the amount of time represented by each fraction as described in example 5. The total amount of time of the fractions of each sample was kept at 115 days as for the reference sample.

Table 1; column i presents the differential of the HbA1c percentage values of the fractions of the reference sample (time template). Similarly to the reference sample, these differentials were calculated for each patient sample. As shown in table 2 E for one patient sample, the division of the differential of the HbA1c percentage values by the differential of the corrected preliminary time scale and the correction for the total HbA1c percentage value of the sample yields the glucose dependent HbA1c percentage rate on a preliminary time scale. To present the glucose dependent HbA1c percentage rate on a time scale as presented in FIG. 3 e, the time values of the fractions were transformed using the formula described in example 3 (for the calculation see table 2 F). The term "real time scale" cannot be used for the patient samples yet, since it appeared that the patient samples showed important variations of the life span, necessitating further corrective actions.

Figure 5B:
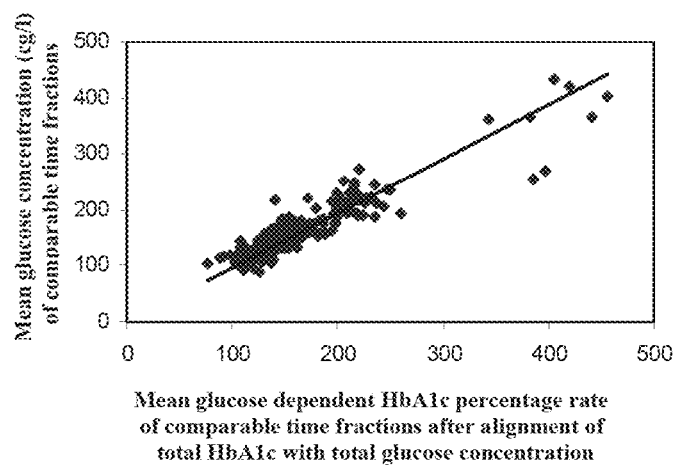

A direct comparison of glucose and glucose dependent HbA1c rate values of all the patients, however suffered from the low correlation between glucose and HbA1c as shown in Example 4 and FIG. 5A. For a better comparison the total mean glucose value of a patient was divided by the total HbA1c value as found by the cytometric assay (Table 2C column t). Also, a correction was needed with respect to the 120 days life-span attributed to the samples. A life-span factor as applied in Table 2D column ad was determined based on an optimal fit between the derived HbA1c percentage profile and the glucose monitoring profile. The resulting individual life-spans showed variations between the patients. After applying these two adaptations, a comparison could be made between the mean glucose value around each time point and the derived HbA1c percentage of the corresponding time points The resulting correlation had an $R^2$ of 0.8 (FIG. 5B). The individual comparisons are shown in FIG. 6.
Statistical Analysis of the Result As can be seen in FIG. 6, there is good concordance over time between the glucose dependent HbA1c percentage rate and the glucose values of the self-monitoring of the patients. After a long search, the life span factor as found by comparison appeared to correlate with parameters owing to the reticulocytes, suggesting a feed-back mechanism between red cell destruction and red cell formation. The life span factor is the product of the hemoglobin content and the RNA content of the reticulocytes.

As shown in example 9, however it was only possible to analyze the data statistically after alignment of the two types of data. The disparity of glucose levels and HbA1c formation is still a subject of debate (Hudson et al. Ann. Clin. Biochem. 1999; vol. 36, 451-459). The data shown in FIG. 5 clearly show the expected correlation between the patterns in time of the glucose levels and the HbA1c formation. Only the absolute levels correlate poorly. A reason could be that the HbA1c reaction/time curve differs substantially between individuals. Oxidative conditions in the blood could give rise to varying rates of formation of advanced glycation end products as described in Makita, Z. et al Science 1992, vol. 258, pp 651-653.

In the calculations above, a fixed formula of $$y=x^{1.2}$$

applied to the time axis was used. In individual cases, changes in the value of the exponent generated further improvement in the comparison of the patterns of the glucose levels with the patterns of glucose dependent HbA1c percentage rate over time. A pattern fitting with a higher value of the exponent would indicate that the HbA1c percentage value would be low compared the mean glucose level.
Mean Cellular Hemoglobin Time Curve.

The determination of the age of the cells in the fractions of the analysis provides for application of a time axis to red blood cell parameters of choice. In the above analysis, mean cellular hemoglobin of the cellular age fractions was determined. In FIG. 9, these mean cellular hemoglobin curves are shown. Typically, hemoglobin reaches a maximum level in cells of 5 or 6 days of age. Aging further, the cells loose hemoglobin as reported (Gifford et al., Br. J. Haematol. 2006 November; 135(3): 395-404). In the patient samples some aberrant patterns have been found (patient 7 and patient 10). Apparently these aberrant patterns are associated with high levels of HbA1c.

Percentage of Represented Cells in the Blood.

Figure 8:
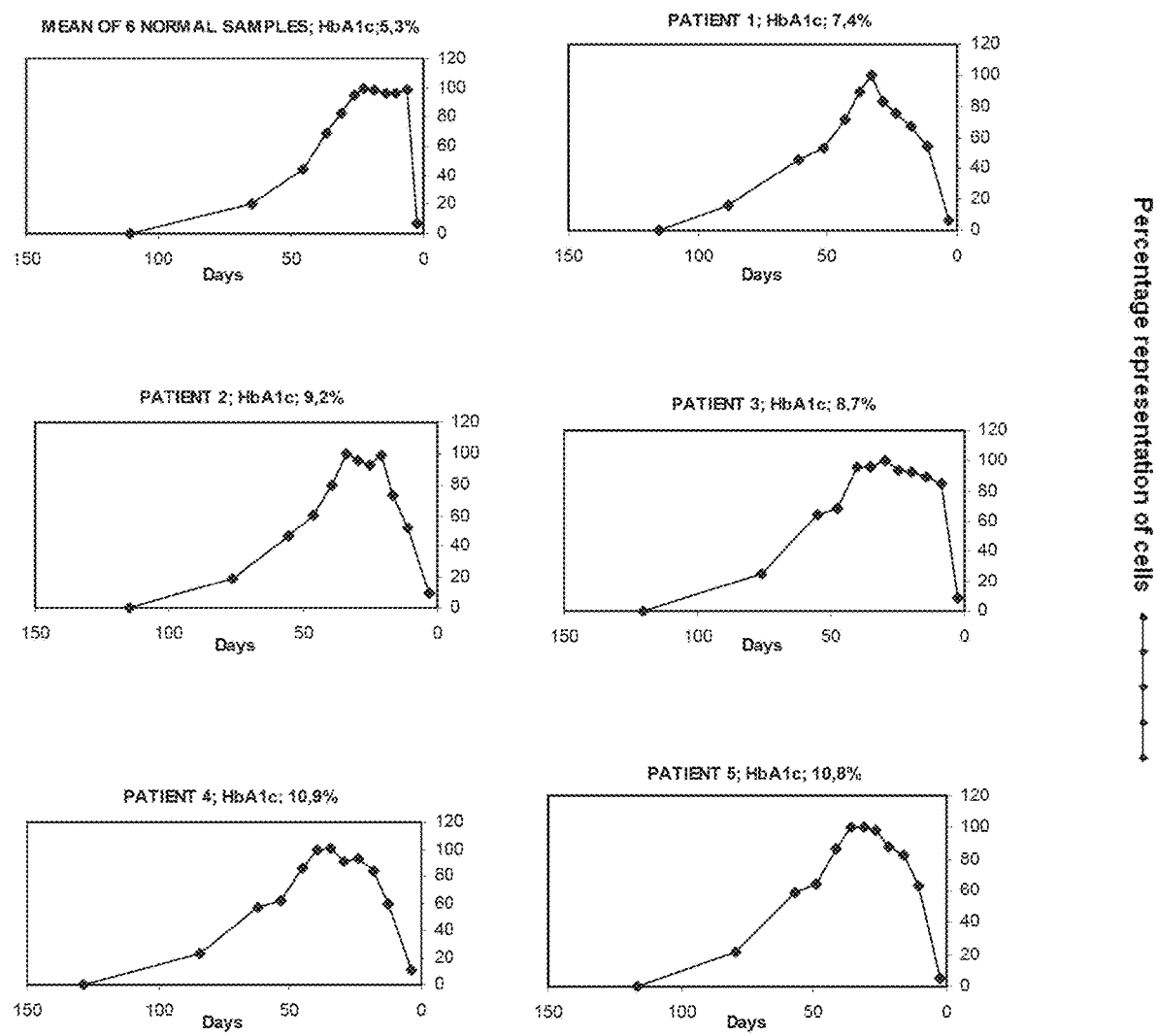
FIG. 8 shows graphical representations of time diagrams containing the percentage of represented cells in the age fractions of the blood in 26 different subjects having diabetes and 6 normal subjects. The percentage values were calculated as described in example 9. The zero percent point has been determination by extrapolation as described in example 10.
Figure 8:
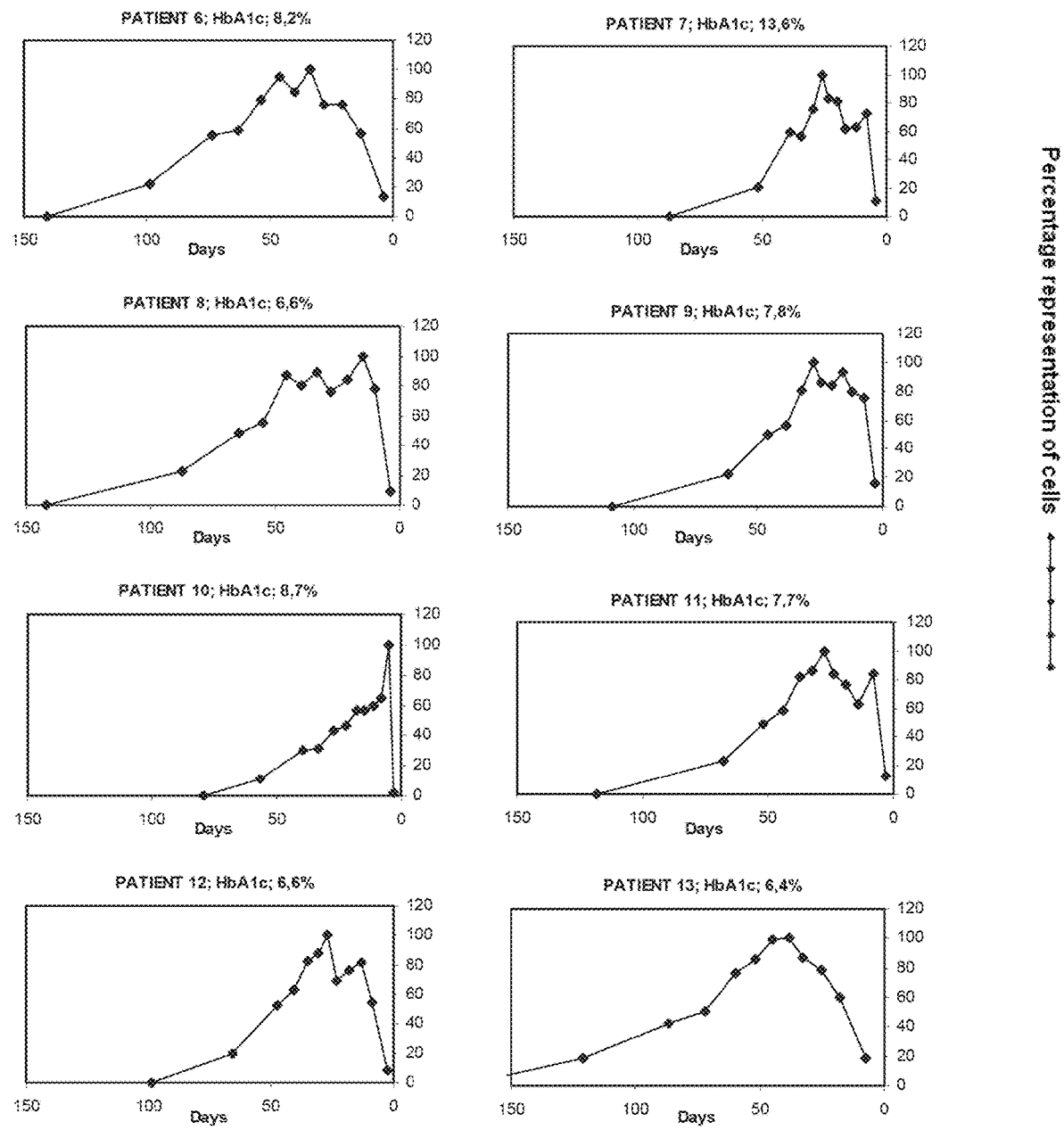
Figure 8:
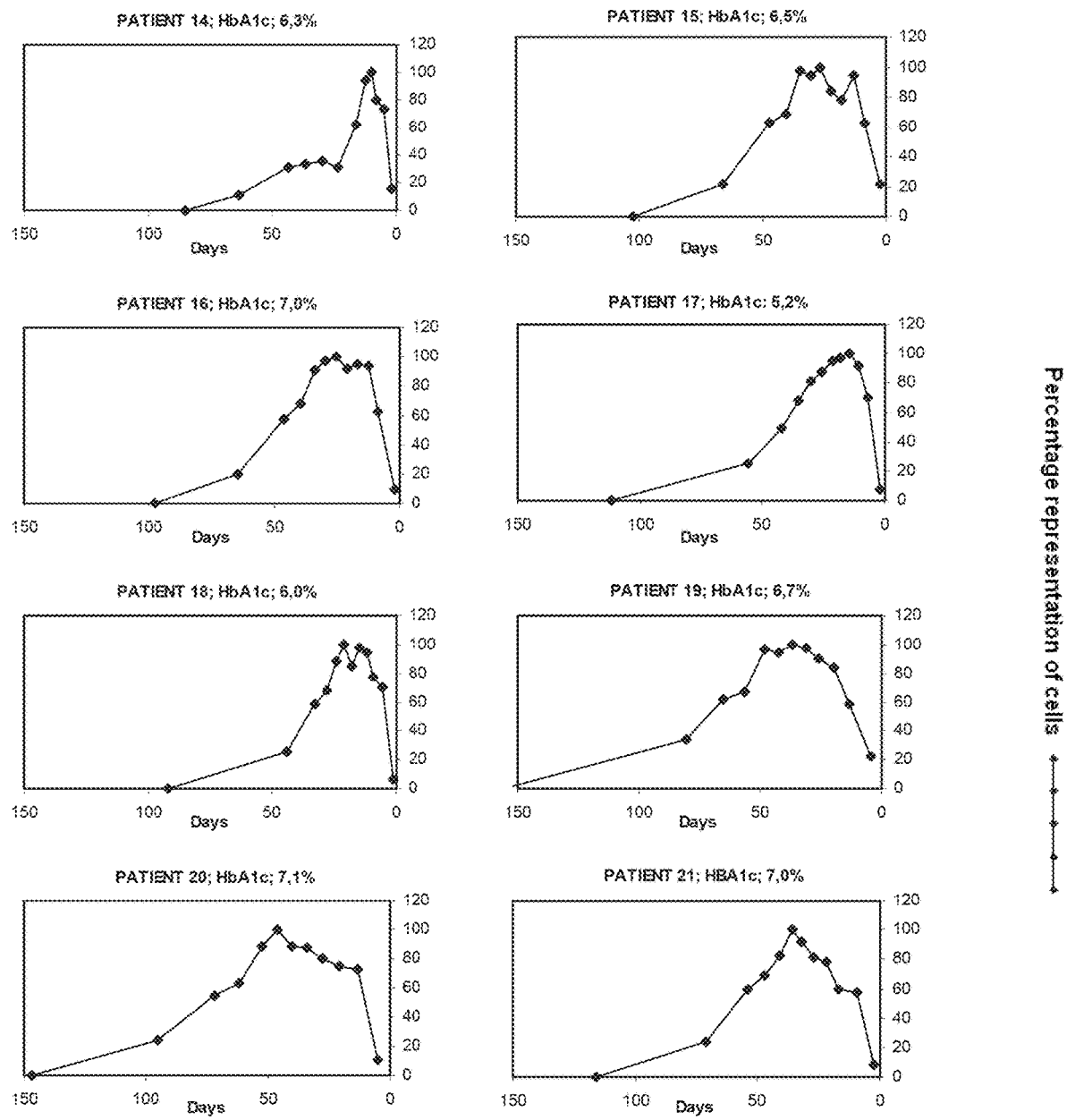
Figure 8:
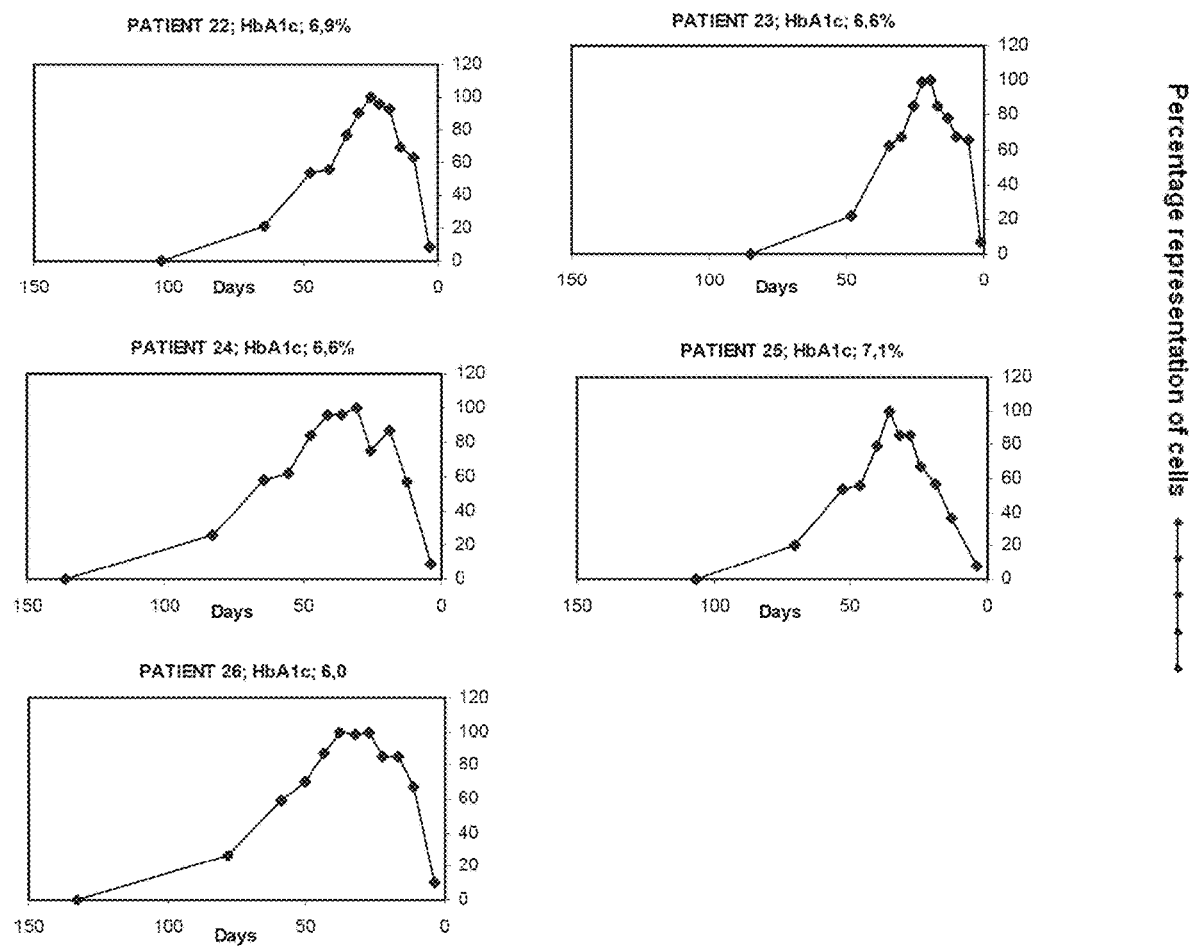

The patterns shown in FIG. 8 give an impression of how much cells that have been originally formed are represented in the blood. This type of diagram is a consequence of the relationship of the amount of time that is represented by a fraction and is the reverse of the percentage of represented cells. For this type of curve there is no reference that defines the 100% value of represented cells. Therefore the highest point of the curve was arbitrarily assigned a value of 100%.

The shape of the curves is highly dependent on the values of the time points on the time axis. These time axes were constructed using the HbA1c reaction/time formula:

$$y = x^{1.3}$$

which had been applied to the time axis. Since the exponent might be subject to variations between the patients as described above, the patterns of these curves might be slightly different in accordance with such variations of the exponent.

In all cases, the curves describe cell death in the last part of the curve and in the first part of the curve a slow appearance of newly formed red cells in the blood. It is generally known that during maturation red cells pass from the bone marrow to the spleen, before release in the blood. There is no information however how much time this takes. From our analysis and from FIG. 8, there seems to be a high degree of variation in the release of red cells in the blood between individuals.

Example 8

This example illustrates a calculation of the life span factors of the patient samples.

Methods and Results

Graphic representations of the glucose dependent HbA1c percentage rate and the time scale as described in Example 6 and calculated in table 2, were compared to the graphic representations of the registered glucose values as measured by the self-monitoring of the patients of Example 4. The time scale of the self-monitored glucose values was made using the calendar associated to the glucose values. By inspecting the glucose profiles on the time scale and the glucose dependent HbA1c values on the calculated time scale it was clear that a great amount of concordance between the two types of measurements existed. Variations between the two types of patterns were apparently due to variations in the life-span of the patient samples. As shown in Example 7, for each patient the values of the calculated time scale were multiplied with a factor that was varied until an optimal fit between the two types of patterns was obtained. For each patient a different factor was obtained and a correlation was sought between these factors and the different parameters, as far as known, of the patients.

A best correlation (FIG. 7; $R^2=0.9$) was found with the product of a function of the FL1 values (RNA content) and of the side scatter values (hemoglobin content) of the reticulocytes (see table 2E).

Calculation of the Life-Span of the Red Blood Cells in the Patients

Simulation experiments as described in example 8 showed a correlation between the life-span of the red blood cells and parameters owing to the reticulocytes. Initially these parameters were sought in the older fractions of the samples, but none could be found. During the maturation of the reticulocytes, the RNA content gradually disappears, while the hemoglobin content rises to obtain to a maximum. In a function of the product of RNA content and hemoglobin content as presented in example 8, the lowering RNA and the rising hemoglobin will equilibrate each other and the value of the function will remain constant during the maturation of the reticulocytes. If both RNA and hemoglobin are low however, it means that the reticulocytes cannot reach a normal hemoglobin level at the time that the blood sample has been drawn. From the observations in example 8, it might be concluded that there is a link between the breakdown of red cells in the reticuloendothelial system and the synthesis of hemoglobin in the reticulocytes. The recycling of iron could play a major role in such a feedback mechanism.

Example 9

This example illustrates the time curve of represented cells in the blood.

Methods and Results

After the construction of the time axis of the patient samples, the calculation of the glucose dependent HbA1c percentage rate values, and the application of the red cell life-span values of the patients, statistical data was obtained to test the validity of the procedure. The time points of the cytometric procedure of a patient sample were projected on the calendar of the self-monitoring glucose readings of the respective patient. For a time point, the glucose reading values of half of the time to the previous time point and half of the time to the next time point were collected and the mean value was calculated. In this way, for each time point of each patient found with the cytometric assay, a comparison could be made between the glucose dependent HbA1c percentage rate and the blood glucose concentration. Except however for those time points that exceeded the time of the patient calendar and for which no counter values were available. A direct comparison of glucose and glucose dependent HbA1c rate values of all the patients (FIG. 5 A), however suffered from the low correlation between glucose and HbA1c as shown in example 4 and FIG. 4. For a better comparison the total mean glucose value of a patient was divided by the total HbA1c value as found by the cytometric assay. The resulting factor was multiplied with the glucose dependent HbA1c percentage rates of each time point of the analysis, which allowed a better comparison. The resulting correlation had an $R^2$ of 0.8 (FIG. 5 B). The individual comparisons are shown in FIG. 6.

From Formula VIII, it can be derived by taking the reverse of the size of the age fractions (Table 2D column ac) multiplied with the number of cells in each fraction (Table 2D column z), how many cells can be recovered in the blood compared with the number of cells in an ideal model, in which cells appear immediately in the blood and die all at exactly the same time. Diagrams of each patient showing the percentage of cells over time are presented in FIG. 8. The highest value in each series had been taken as a 100% reference point.

Example 10

This example illustrates an estimation of the life-span and the mean age.

Methods and Results

The representation of cells in the circulation as shown in FIG. 8 allows making an extrapolation of the curve to the zero value. The point on the time axis of this zero value would reflect the age of the oldest cells in the blood and of the life-span of the red blood cells. The extrapolation as shown in FIG. 8 is a prolongation of the curve after the value of the fraction 10. The angle that the prolongation makes with the time axis is taken half of the angle that the segment between the 9$^{th}$ and the 10$^{th}$ fraction makes with the time axis. The mean age is calculated by multiplying the number of cells in each fraction with the age of the fraction. The sum of these multiplications is divided by the total number of red cells of the analysis. Table 3 summarizes the estimated life-span and mean age of the reference samples and patient samples described in FIGS. 8 and 9.

TABLE 3

| SAMPLE | | LIFE-SPAN (days) | MEAN AGE (days) |
|---|---|---|---|
| REFERENCE | | 111 | 28 |
| PATIENT | 1 | 115 | 40 |
| | 2 | 115 | 35 |
| | 3 | 120 | 35 |
| | 4 | 128 | 40 |
| | 5 | 117 | 37 |
| | 6 | 141 | 47 |
| | 7 | 87 | 26 |
| | 8 | 142 | 40 |
| | 9 | 108 | 29 |
| | 10 | 79 | 23 |
| | 11 | 118 | 32 |
| | 12 | 99 | 31 |
| | 13 | 170 | 55 |
| | 14 | 84 | 25 |
| | 15 | 103 | 31 |
| | 16 | 98 | 29 |
| | 17 | 112 | 26 |
| | 18 | 92 | 21 |
| | 19 | 156 | 42 |
| | 20 | 147 | 46 |
| | 21 | 116 | 36 |
| | 22 | 103 | 30 |
| | 23 | 85 | 23 |
| | 24 | 136 | 41 |
| | 25 | 107 | 36 |
| | 26 | 132 | 38 |

Example 11

This example illustrates a time curve of mean cellular hemoglobin content.

Methods and Results

Using the time points of the age curves of the patient blood and after confirmation of these time points in the glucose dependent HbA1c rate assay, it was possible to construct mean cellular hemoglobin time curves. The time curves of the patients of the study are presented in FIG. 9.

The foregoing is illustrative of the present disclosure, and is not to be construed as limiting thereof. The disclosure is defined by the following claims, with equivalents of the claims to be included therein. All references and documents referred to herein are hereby incorporated by reference.

What is claimed is:

1. A method for determining age profile of a population of red blood cells in a blood sample, the method comprising:
   measuring by flow cytometry the cellular hemoglobin content, glycated hemoglobin (HbA1c) content, and RNA content of each of the individual red blood cells in the red blood cell population;
   determining the percentage of HbA1c in each of the individual red blood cells from the HbA1c content and the hemoglobin content of each of the individual red blood cells in the population;
   fractionating the data for the red blood cell population into reticulocytes, based on the RNA content, and a plurality of sample fractions of mature red blood cells based on percentage of HbA1c in each individual red blood cell, Wherein each fraction comprises a substantially equal number of red blood cells;
   determining the mean percentage of HbA1c in each sample fraction;
   calculating a life span factor for the population of red blood cells in the blood sample; and
   identifying the age of the red blood cells in each fraction by comparing the mean percentage of HbA1c in each sample fraction to a mean percentage of HbA1c for a red blood cell reference control fraction of a normal red blood cell control sample as corrected by the life span factor, each RBC reference control fraction having a reference time template in days.

2. The method of claim 1, further comprising determining the density of the red blood cells in each red blood cell sample fraction of selected HbA1c percentage as compared to the corresponding RBC reference control fraction, each RBC reference control fraction having a known density.

3. The method of claim 2, wherein the reference control cells have a mean age of at least 28 days.

4. The method of claim 1, wherein the cellular hemoglobin of each individual red blood cell is measured by side scatter.

5. The method of claim 4, wherein HbA1c is measured using a detectably labelled antibody specific for HbA1c or variant thereof.

6. The method of claim 1, wherein the RNA content in the red blood cells is measured by binding to a dye.

7. The method of claim 6, wherein the dye is acridine orange.

8. The method of claim 1, wherein each reference cell fraction comprises red blood cells with a known percentage of HbA1c.

9. The method of claim 8, further comprising
   collecting data from each fraction, the data comprising exact number of red blood cells in each fraction,
   mean HbA1c of the reticulocyte fraction, and
   a fluorescence value and side scatter units for each individual red blood each sample fraction.

10. The method of claim 1, wherein the percentage of HbA1c for each individual red blood cell is determined by dividing the HbA1c content by the cellular hemoglobin content.

11. The method of claim 10, further comprising determining the mean cellular hemoglobin content for each sample fraction having a certain age, and determining whether there is a difference in the mean cellular hemoglobin content in sample fractions of different ages.

12. The method of claim 1, wherein the life span factor is derived from reticulocyte hemoglobin content and the RNA content.

13. The method of claim 1, wherein the life span factor is derived by dividing the percentage of HbA1c of 10% of the oldest red blood cells by a mean percentage of the HcA1c of the total red blood cells.

14. The method of claim 1, wherein the identifying the age of the red blood cells in each sample fraction comprises comparing the mean percentage of HbA1c to the mean percentage of HbA1c for the corresponding reference control fraction as corrected by the life span factor.

15. The method of claim 1, wherein each red blood cell reference control fraction has known percentage of HbA1C.

16. The method of claim 1, wherein the red blood cell reference control sample is a labelled red blood cell reference control sample.

17. The method of claim 1, wherein prior to the flow cytometry the red blood cells in the sample are exposed to
- a dye that specifically binds to RNA;
- a sphering reagent;
- a permeation reagent;
- a labelled red blood cell reference internal control sample;
- a neutralization reagent comprising an anti-Hb1Ac antibody covalently conjugated to a fluorescent dye; and
- a fixation reagent.

18. The method of claim 1, further comprising calculating the mean age of the red blood cells in the sample by multiplying the number of red blood cells in each fraction with the age of the fraction and dividing the sum of the multiplications by the total number of red cells of the analysis.

19. The method of claim 1, wherein the reference time template is based on the differential of the HbA1c percentage values of each red blood cell reference control fraction of the reference control sample per time in days.

20. The method of claim 19, wherein the differential of the HbA1c percentage values for each reference cell fraction is calculated by fraction size in HbA1c percentage=fraction (n)−fraction (n−1).

* * * * *